United States Patent
Luengo et al.

(10) Patent No.: US 6,858,630 B2
(45) Date of Patent: Feb. 22, 2005

(54) NAPHTHIMIDAZOLE DERIVATIVES AND THEIR USE AS THROMBOPOIETIN MIMETICS

(75) Inventors: Juan I. Luengo, Audubon, PA (US); Kevin J. Duffy, Norristown, PA (US); Alan T. Price, Phoenixville, PA (US); Lihua Zhang, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/148,945

(22) PCT Filed: Dec. 6, 2000

(86) PCT No.: PCT/US00/33432

§ 371 (c)(1),
(2), (4) Date: Sep. 12, 2002

(87) PCT Pub. No.: WO01/39773

PCT Pub. Date: Jun. 7, 2001

(65) Prior Publication Data

US 2003/0083361 A1 May 1, 2003

Related U.S. Application Data

(60) Provisional application No. 60/169,130, filed on Dec. 6, 1999.

(51) Int. Cl.$^7$ .................. A61K 31/4184; C07D 235/02
(52) U.S. Cl. .................. 514/322; 514/338; 514/393; 514/394; 546/199; 546/273.1; 548/302.1
(58) Field of Search .................. 548/302.1; 546/199, 546/273.1; 514/393, 394, 322, 338

(56) References Cited

U.S. PATENT DOCUMENTS

| 851,444 A | 4/1907 | Schulthess | |
|---|---|---|---|
| 4,411,907 A | * 10/1983 | Toia | 514/396 |
| 4,435,417 A | * 3/1984 | Toja et al. | 514/394 |

FOREIGN PATENT DOCUMENTS

| DE | 193350 | 12/1907 |
| DE | 248383 | * 6/1912 |
| WO | WO 92/03423 | 5/1992 |

OTHER PUBLICATIONS

Beilsteins Handbuch Der Organischen Chemie, Edwards Brothers, Inc., Ann Arbor, Michigan, 1936, p. 528 (Beilstein Citatio 0–25–00–00528).*

* cited by examiner

*Primary Examiner*—Laura L. Stockton
(74) *Attorney, Agent, or Firm*—Wayne I. Dustman; Stephen Venetianer; Charles M. Kinzig

(57) ABSTRACT

Invented are non-peptide TPO mimetics. Also invented is a method of treating thrombocytopenia, in a mammal, including a human, in need thereof which comprises administering to such mammal an effective amount of a selected substituted naphthimidazole derivative.

12 Claims, No Drawings

NAPHTHIMIDAZOLE DERIVATIVES AND THEIR USE AS THROMBOPOIETIN MIMETICS

This application is a 371 of PCT/US00/33432 filed Dec. 6, 2000 which, claims the benefit of U.S. Provisional Application No. 60/169,130, filed Dec. 6, 1999.

FIELD OF THE INVENTION

This invention relates to thrombopoietin (TPO) mimetics and their use as promoters of thrombopoiesis and megakaryocytopoiesis.

BACKGROUND OF THE INVENTION

Megakaryocytes are bone marrow-derived cells, which are responsible for producing circulating blood platelets. Although comprising <0.25% of the bone marrow cells in most species, they have >10 times the volume of typical marrow cells. See Kuter et al. *Proc. Natl. Acad. Aci. USA* 91: 11104–11108 (1994). Megakaryocytes undergo a process known as endomitosis whereby they replicate their nuclei but fail to undergo cell division and thereby give rise to polypoid cells. In response to a decreased platelet count, the endomitotic rate increases, higher ploidy megakaryocytes are formed, and the number of megakaryocytes may increase up to 3-fold. See Harker *J. Clin. Invest.* 47: 458–465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf Nature 369:519–520 (1994). TPO has been shown in several studies to increase platelet counts, increase platelet size, and increase isotope incorporation into platelets of recipient animals. Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at risk of death from catastrophic hemorrhage, TPO has potential useful application in both the diagnosis and the treatment of various hematological disorders, for example, diseases primarily due to platelet defects. Ongoing clinical trials with TPO have indicated that TPO can be administered safely to patients. In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See e.g., McDonald (1992) *Am. J. Ped. Hematology/Oncology* 14: 8–21 (1992).

The gene encoding TPO has been cloned and characterized. See Kuter et al., *Proc. Natl. Acad. Sci. USA* 91: 11104–11108 (1994); Barley et al., *Cell* 77: 1117–1124 (1994); Kaushansky et al., *Nature* 369:568–571 (1994); Wendling et al., *Nature* 369: 571–574 (1994); and Sauvage et al., *Nature* 369: 533–538 (1994). Thrombopoietin is a glycoprotein with two distinct regions separated by a potential Arg—Arg cleavage site. The amino-terminal region is highly conserved in man and mouse, and has some homology with erythropoietin and interferon-alpha and interferon-beta. The carboxy-terminal region shows wide species divergence.

The DNA sequences and encoded peptide sequences for human TPO receptor (TPO-R; also known as c-mpl) have been described. See, Vigon et al. *Proc. Natl. Acad. Sci. USA* 89: 5640–5644 (1992). TPO-R is a member of the haematopoietin growth factor receptor family, a family characterized by a common structural design of the extracellular domain, including for conserved C residues in the N-terminal portion and a WSXWS motif close to the transmembrane region. See Bazan *Proc. Natl. Acad. Sci. USA* 87: 6934–6938 (1990). Evidence that this receptor plays a functional role in hematopoiesis includes observations that its expression if restricted to spleen, bone marrow, or fetal liver in mice (see Souyri et al. *Cell* 63: 1137–1147 (1990)) and to megakaryocytes, platelets, and CD34$^+$ cells in humans (see Methia et al. *Blood* 82: 1395–1401 (1993)). Further evidence for TPO-R as a key regulator of megakaryopoiesis is the fact that exposure of CD34$^+$ cells to synthetic oligonucleotides antisense to TPO-R RNA significantly inhibits the appearance of megakaryocyte colonies without affecting erythroid or myeloid colony formation. Some workers postulate that the receptor functions as a homodimer, similar to the situation with the receptors for G-CSF and erythropoietin.

The slow recovery of platelet levels in patients suffering from thrombocytopenia is a serious problem, and has lent urgency to the search for a blood growth factor agonist able to accelerate platelet regeneration.

It would be desirable to provide compounds which allow for the treatment of thrombocytopenia by acting as a TPO mimetic.

As disclosed herein it has unexpectedly been discovered that certain substituted naphthimidazole derivatives are effective as agonists of the TPO receptor, they are potent TPO mimetics.

SUMMARY OF THE INVENTION

This invention relates to compounds of Formula (I):

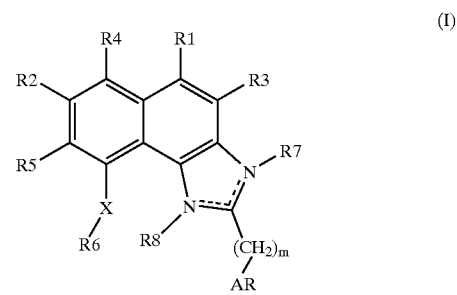

wherein:
the C ring has one double bond where indicated by the broken lines, provided that R$^8$ is absent when the nitrogen attached thereto has a double bond and provided that R$^7$ is absent when the nitrogen attached thereto has a double bond;
R$^1$, R$^2$, R$^3$, R$^4$ and R$^5$ are each independently selected from the group consisting of: hydrogen, —C(O)OR$^{11}$, —CONR$^9$R$^{10}$, —SO$_2$NR$^9$R$^{10}$, phosphonic acid, phosphinic acid, C$_{1-6}$alkyl, C$_{1-6}$alkoxy, —(CH$_2$)$_p$OR$^{11}$, nitro, cyano, halogen, —NR$^9$R$^{10}$, N-acylamino, N-sulfonylamino, —S(O)$_n$R$^{11}$, aryl, substituted aryl, alkyl, cycloalkyl, substituted cycloalkyl, protected —OH, and alkyl substituted with one or more substituents selected from the group consisting of: alkoxy, acyloxy, aryl, substituted aryl, —NR$^9$R$^{10}$, N-acylamino, oxo, hydroxy, cycloalkyl, substituted cycloalkyl, —C(O)OR$^{11}$, —C(O)NR$^9$R$^{10}$, —S(O)$_2$NR$^9$R$^{10}$, —S(O)$_n$R$^{11}$, aryloxy, nitro, cyano, halogen, and protected —OH;

where n is 0 to 3;

p is 0 to 6;

R$^{11}$ is selected from the group consisting of: hydrogen, alkyl, cycloalkyl, C$_1$–C$_{12}$aryl, substituted alkyl, substituted cycloalkyl and substituted C$_1$–C$_{12}$aryl; and R$^9$ and R$^{10}$ are independently selected from hydrogen, cycloalkyl, C$_1$–C$_{12}$aryl, substituted cycloalkyl, substituted C$_1$–C$_{12}$aryl, alkyl or alkyl substituted with one or more substituents selected from the group consisting of: alkoxy, acyloxy, aryloxy, —NR$^{11}$R$^{11}$, N-acylamino, oxo, hydroxy, —C(O)OR$^{11}$, —S(O)$_n$R$^{11}$, —C(O)NR$^{11}$R$^{11}$, —S(O)$_2$NR$^{11}$R$^{11}$, nitro, cyano, halogen, cycloalkyl, substituted cycloalkyl, aryl, substituted aryl and protected —OH where n and R$^{11}$ are as described above; or R$^9$ and R$^{10}$ taken together with the nitrogen to which they are attached represent a 5 to 6 member saturated ring containing up to one other heteroatom selected from oxygen and nitrogen;

R$^6$ is selected from the group consisting of: hydrogen, alkyl, cycloalkyl, C$_1$–C$_{12}$aryl, substituted alkyl, substituted cycloalkyl and substituted C$_1$–C$_{12}$aryl;

R$^7$ is absent when the nitrogen attached thereto has a double bond or selected from the group consisting of: hydrogen, alkyl, cycloalkyl, C$_1$–C$_{12}$aryl, substituted alkyl, substituted cycloalkyl and substituted C$_1$–C$_{12}$aryl;

R$^8$ is absent when the nitrogen attached thereto has a double bond or selected from the group consisting of: hydrogen, alkyl, cycloalkyl, C$_1$–C$_{12}$aryl, substituted alkyl, substituted cycloalkyl and substituted C$_1$–C$_{12}$aryl;

m is 0–6;

X is selected from the group consisting of sulfur, sulfonamido, oxygen and an amino group which may be substituted by C$_1$–C$_{10}$alkyl or benzyl;

AR is a cyclic or polycyclic aromatic ring containing from 3 to 16 carbon atoms, optionally containing one or more heteroatoms, provided that when the number of carbon atoms is 3 the aromatic ring contains at least two heteroatoms and when the number of carbon atoms is 4 the aromatic ring contains at least one heteroatom, optionally substituted with one or more substituents selected from the group consisting of: alkyl, substituted alkyl, cycloalkyl, substituted cycloalkyl, aryl, substituted aryl, aryloxy, hydroxy, alkoxy, acyloxy, —NR$^{12}$R$^{13}$, N-acylamino, N-sulfonylamino, nitro, cyano, halogen, —C(O)OR$^{11}$, —C(O)NR$^{12}$R$^{13}$, —S(O)$_2$NR$^{12}$R$^{13}$, —S(O)$_n$R$^{11}$, protected —OH, and alkyl substituted with one or more substituents selected from the group consisting of: alkoxy, acyloxy, aryl, substituted aryl, amino, N-acylamino, oxo, hydroxy, cycloalkyl, substituted cycloalkyl, —C(O)OR$^{11}$, —S(O)$_2$NR$^{12}$R$^{13}$, —S(O)$_n$R$^{11}$, aryloxy, nitro, cyano, halogen, and protected —OH, where n is 0 to 3;

R$^{11}$ is selected from the group consisting of: hydrogen, alkyl, cycloalkyl, C$_1$–C$_{12}$aryl, substituted alkyl, substituted cycloalkyl and substituted C$_1$–C$_{12}$aryl, and R$^{12}$ and R$^{13}$ are independently selected from the group consisting of: hydrogen, cycloalkyl, C$_1$–C$_{12}$aryl, substituted cycloalkyl, substituted C$_1$–C$_{12}$aryl, alkyl or alkyl substituted with one or more substituents selected from the group consisting of: alkoxy, acyloxy, aryloxy, —NR$^{11}$R$^{11}$, N-acylamino, oxo, hydroxy, —C(O)OR$^{11}$, —S(O)$_n$R$^{11}$, —C(O)NR$^{11}$R$^{11}$, —S(O)$_2$NR$^{11}$R$^{11}$, nitro, cyano, cycloalkyl, substituted cycloalkyl, halogen, C$_1$–C$_{12}$aryl, substituted C$_1$–C$_{12}$aryl, and protected —OH, where n and R$^{11}$ are as described above; and pharmaceutically acceptable salts, hydrates, solvates and esters thereof.

This invention relates to a method of treating thrombocytopenia, which comprises administering to a subject in need thereof an effective amount of a TPO mimetic compound of Formula (I).

The present invention also relates to the discovery that the compounds of Formula (I) are active as agonists of the TPO receptor.

In a further aspect of the invention there is provided novel processes and novel intermediates useful in preparing the presently invented TPO mimetic compounds.

Included in the present invention are pharmaceutical compositions comprising a pharmaceutical carrier and compounds useful in the methods of the invention.

Also included in the present invention are methods of co-administering the presently invented TPO mimetic compounds with further active ingredients.

DETAILED DESCRIPTION OF THE INVENTION

This invention relates to compounds of Formula (I) as described above.

Preferred among the presently invented compounds are those having Formula (II):

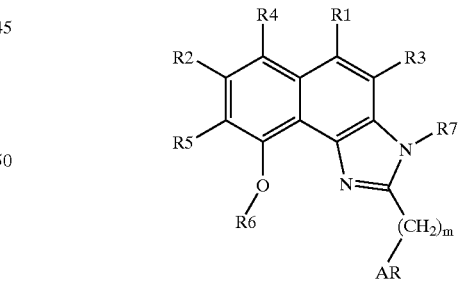

in which

R$^1$, R$^2$, R$^3$, R$^4$ and R$^5$ are each independently selected from the group consisting of: carboxylic acid, sulfonic acid, hydrogen, C$_{1-6}$alkoxy, C$_{1-6}$alkyl and halogen;

R$^6$ is selected form the group consisting of: hydrogen, alkyl, cycloalkyl, C$_1$–C$_{12}$aryl and substituted alkyl;

R$^7$ is selected form the group consisting of: hydrogen, alkyl, cycloalkyl, C$_1$–C$_{12}$aryl and substituted alkyl;

m is 0–3; and

AR is cyclic or polycyclic aromatic C$_3$–C$_{14}$, optionally containing from one to three heteroatoms, provided that when C is 3 the aromatic ring contains at least two heteroatoms and when C is 4 the aromatic ring contains at least one heteroatom, and optionally substituted with one or more substituents selected from the group consisting of: alkyl, substituted alkyl, $C_1$–$C_{12}$aryl, substituted cycloalkyl, substituted $C_1$–$C_{12}$aryl, aryloxy, —$NR^{11}R^{11}$, hydroxy, alkoxy, cycloalkyl, amino, nitro, cyano, halogen and protected —OH, where $R^{11}$ is selected from the group consisting of: hydrogen, alkyl, cycloalkyl, $C_1$–$C_{12}$aryl, substituted alkyl, substituted cycloalkyl and substituted $C_1$–$C_{12}$aryl; and pharmaceutically acceptable salts, hydrates, solvates and esters thereof.

Particularly preferred among the presently invented Formula II compounds are those in which $R^1$, $R^2$, $R^3$, $R^4$ and $R^5$ are each independently selected from carboxylic acid, sulfonic acid, hydrogen, $C_{1-3}$alkoxy, $C_{1-3}$alkyl and halogen; $R^6$ is selected form hydrogen, alkyl and substituted alkyl; $R^7$ is selected form hydrogen, alkyl and substituted alkyl; m is 0; and AR is selected from naphthalene, phenyl, pyridine and pyrazole, and optionally substituted with from one to three substituents selected from the group consisting of: alkyl, substituted alkyl, $C_1$–$C_{12}$aryl, substituted $C_1$–$C_{12}$aryl, hydroxy, amino, —$NR^{11}R^{11}$, alkoxy and halogen, where $R^{11}$ is selected from the group consisting of: hydrogen, alkyl, cycloalkyl, $C_1$–$C_{12}$aryl, substituted alkyl, substituted cycloalkyl and substituted $C_1$–$C_{12}$aryl; and pharmaceutically acceptable salts, hydrates, solvates and esters thereof. Preferred among the presently invented compounds are:

2-(3-[2'-Methylphenyl]-2-methoxyphenyl)-9-hydroxy-naphth[1,2-d]imidazole-5-sulfonic acid hydrochloride;
2-(3-[4'-Methylphenyl]-2-methoxyphenyl)-9-hydroxy-naphth[1,2-d]imidazole-5-sulfonic acid hydrochloride;
2-(3-[3',4'-Dimethylphenyl]-2-methoxyphenyl)-9-hydroxy-naphth[1,2-d]imidazole-5-sulfonic acid hydrochloride;
2-(3-[3'-Methoxyphenyl]-2-methoxyphenyl)-9-hydroxy-naphth[1,2-d]imidazole-5-sulfonic acid hydrochloride;
2-(3-[3'-Trifluoromethylphenyl]-2-methoxyphenyl)-9-hydroxy-naphth[1,2-d]imidazole-5-sulfonic acid hydrochloride;
2-(3-[4'-Fluorophenyl]-2-methoxyphenyl)-9-hydroxy-naphth[1,2-d]imidazole-5-sulfonic acid hydrochloride;
2-(3-[4'-Chlorophenyl]-2-methoxyphenyl)-9-hydroxy-naphth[1,2-d]imidazole-5-sulfonic acid hydrochloride;
2-(3-[1'-Dibenzofuranyl]-2-methoxyphenyl)-9-hydroxy-naphth[1,2-d]imidazole-5-sulfonic acid hydrochloride;
2-(3-[1'-Naphthalenyl]-2-methoxyphenyl)-9-hydroxy-naphth[1,2-d]imidazole-5-sulfonic acid hydrochloride;
2-(3-[3'-Chlorophenyl]-2-methoxyphenyl)-9-hydroxy-naphth[1,2-d]imidazole-5-sulfonic acid hydrochloride;
2-(3-[3'-Nitrophenyl]-2-methoxyphenyl)-9-hydroxy-naphth[1,2-d]imidazole-5-sulfonic acid hydrochloride;
2-(3-phenyl-2-methoxyphenyl)-9-hydroxy-naphth[1,2-d]imidazole-5-sulfonic acid hydrochloride;
2-(3-[2'-Methylphenyl]-2-methoxyphenyl)-9-hydroxy-naphth[1,2-d]imidazole-7-sulfonic acid hydrochloride;
2-(3-[4'-Methylphenyl]-2-methoxyphenyl)-9-hydroxy-naphth[1,2-d]imidazole-7-sulfonic acid hydrochloride;
2-(3-[3',4'-Dimethylphenyl]-2-methoxyphenyl)-9-hydroxy-naphth[1,2-d]imidazole-5-sulfonic acid hydrochloride;
2-(3-[3'-Methoxyphenyl]-2-methoxyphenyl)-9-hydroxy-naphth[1,2-d]imidazole-7-sulfonic acid hydrochloride;
2-(3-[3'-Trifluoromethylphenyl]-2-methoxyphenyl)-9-hydroxy-naphth[1,2-d]imidazole-7-sulfonic acid hydrochloride;
2-(3-[4'-Fluorophenyl]-2-methoxyphenyl)-9-hydroxy-naphth[1,2-d]imidazole-7-sulfonic acid hydrochloride;
2-(3-[4'-Chlorophenyl]-2-methoxyphenyl)-9-hydroxy-naphth[1,2-d]imidazole-7-sulfonic acid hydrochloride;
2-(3-[1'-Dibenzofuranyl]-2-methoxyphenyl)-9-hydroxy-naphth[1,2-d]imidazole-7-sulfonic acid hydrochloride;
2-(3-[1'-Naphthalenyl]-2-methoxyphenyl)-9-hydroxy-naphth[1,2-d]imidazole-7-sulfonic acid hydrochloride;
2-(3-[3'-Chlorophenyl]-2-methoxyphenyl)-9-hydroxy-naphth[1,2-d]imidazole-7-sulfonic acid hydrochloride;
2-(3-[3'-Nitrophenyl]-2-methoxyphenyl)-9-hydroxy-naphth[1,2-d]imidazole-7-sulfonic acid hydrochloride;
2-(3-phenyl-2-methoxyphenyl)-9-hydroxy-naphth[1,2-d]imidazole-7-sulfonic acid hydrochloride;
2-(4-[2'-Methylphenyl]-2-methoxyphenyl)-9-hydroxy-naphth[1,2-d]imidazole-5-sulfonic acid hydrochloride;
2-(4-[4'-Methylphenyl]-2-methoxyphenyl)-9-hydroxy-naphth[1,2-d]imidazole-5-sulfonic acid hydrochloride;
2-(4-[3',4'-Dimethylphenyl]-2-methoxyphenyl)-9-hydroxy-naphth[1,2-d]imidazole-5-sulfonic acid hydrochloride;
2-(4-[3'-Methoxyphenyl]-2-methoxyphenyl)-9-hydroxy-naphth[1,2-d]imidazole-5-sulfonic acid hydrochloride;
2-(4-[3'-Trifluoromethylphenyl]-2-methoxyphenyl)-9-hydroxy-naphth[1,2-d]imidazole-5-sulfonic acid hydrochloride;
2-(4-[4'-Fluorophenyl]-2-methoxyphenyl)-9-hydroxy-naphth[1,2-d]imidazole-5-sulfonic acid hydrochloride;
2-(4-[4'-Chlorophenyl]-2-methoxyphenyl)-9-hydroxy-naphth[1,2-d]imidazole-5-sulfonic acid hydrochloride;
2-(4-[1'-Dibenzofuranyl]-2-methoxyphenyl)-9-hydroxy-naphth[1,2-d]imidazole-5-sulfonic acid hydrochloride;
2-(4-[1'-Naphthalenyl]-2-methoxyphenyl)-9-hydroxy-naphth[1,2-d]imidazole-5-sulfonic acid hydrochloride;
2-(4-[3'-Chlorophenyl]-2-methoxyphenyl)-9-hydroxy-naphth[1,2-d]imidazole-5-sulfonic acid hydrochloride;
2-(4-[3'-Nitrophenyl]-2-methoxyphenyl)-9-hydroxy-naphth[1,2-d]imidazole-5-sulfonic acid hydrochloride;
2-(4-phenyl-2-methoxyphenyl)-9-hydroxy-naphth[1,2-d]imidazole-5-sulfonic acid hydrochloride;
2-(4-[2'-Methylphenyl]-2-methoxyphenyl)-9-hydroxy-naphth[1,2-d]imidazole-7-sulfonic acid hydrochloride;
2-(4-[4'-Methylphenyl]-2-methoxyphenyl)-9-hydroxy-naphth[1,2-d]imidazole-7-sulfonic acid hydrochloride;
2-(4-[3',4'-Dimethylphenyl]-2-methoxyphenyl)-9-hydroxy-naphth[1,2-d]imidazole-7-sulfonic acid hydrochloride;
2-(4-[3'-Methoxyphenyl]-2-methoxyphenyl)-9-hydroxy-naphth[1,2-d]imidazole-7-sulfonic acid hydrochloride;
2-(4-[3'-Trifluoromethylphenyl]-2-methoxyphenyl)-9-hydroxy-naphth[1,2-d]imidazole-7-sulfonic acid hydrochloride;
2-(4-[4'-Fluorophenyl]-2-methoxyphenyl)-9-hydroxy-naphth[1,2-d]imidazole-7-sulfonic acid hydrochloride;
2-(4-[4'-Chlorophenyl]-2-methoxyphenyl)-9-hydroxy-naphth[1,2-d]imidazole-7-sulfonic acid hydrochloride;
2-(4-[1'-Dibenzofuranyl]-2-methoxyphenyl)-9-hydroxy-naphth[1,2-d]imidazole-7-sulfonic acid hydrochloride;
2-(4-[1'-Naphthalenyl]-2-methoxyphenyl)-9-hydroxy-naphth[1,2-d]imidazole-7-sulfonic acid hydrochloride;
2-(4-[3'-Chlorophenyl]-2-methoxyphenyl)-9-hydroxy-naphth[1,2-d]imidazole-7-sulfonic acid hydrochloride;
2-(4-[3'-Nitrophenyl]-2-methoxyphenyl)-9-hydroxy-naphth[1,2-d]imidazole-7-sulfonic acid hydrochloride;
2-(4-phenyl-2-methoxyphenyl)-9-hydroxy-naphth[1,2-d]imidazole-7-sulfonic acid hydrochloride;
2-(3-[2'-Methylphenyl]-2-hydroxyphenyl)-9-hydroxy-naphth[1,2-d]imidazole-5-sulfonic acid hydrochloride;
2-(3-[4'-Methylphenyl]-2-hydroxyphenyl)-9-hydroxy-naphth[1,2-d]imidazole-5-sulfonic acid hydrochloride;

2-(3-[3',4'-Dimethylphenyl]-2-hydroxyphenyl)-9-hydroxy-naphth[1,2-d]imidazole-5-sulfonic acid hydrochloride;
2-(3-[3'-Trifluoromethylphenyl]-2-hydroxyphenyl)-9-hydroxy-naphth[1,2-d]imidazole-5-sulfonic acid hydrochloride;
2-(3-[4'-Fluorophenyl]-2-hydroxyphenyl)-9-hydroxy-naphth[1,2-d]imidazole-5-sulfonic acid hydrochloride;
2-(3-[4'-Chlorophenyl]-2-hydroxyphenyl)-9-hydroxy-naphth[1,2-d]imidazole-5-sulfonic acid hydrochloride;
2-(3-[1'-Dibenzofuranyl]-2-hydroxyphenyl)-9-hydroxy-naphth[1,2-d]imidazole-5-sulfonic acid hydrochloride;
2-(3-[1'-Naphthalenyl]-2-hydroxyphenyl)-9-hydroxy-naphth[1,2-d]imidazole-5-sulfonic acid hydrochloride;
2-(3-[3'-Chlorophenyl]-2-hydroxyphenyl)-9-hydroxy-naphth[1,2-d]imidazole-5-sulfonic acid hydrochloride;
2-(3-[3'-Nitrophenyl]-2-hydroxyphenyl)-9-hydroxy-naphth[1,2-d]imidazole-5-sulfonic acid hydrochloride;
2-(3-phenyl-2-hydroxyphenyl)-9-hydroxy-naphth[1,2-d]imidazole-5-sulfonic acid hydrochloride;
2-(3-[2'-Methylphenyl]-2-hydroxyphenyl)-9-hydroxy-naphth[1,2-d]imidazole-7-sulfonic acid hydrochloride;
2-(3-[4'-Methylphenyl]-2-hydroxyphenyl)-9-hydroxy-naphth[1,2-d]imidazole-7-sulfonic acid hydrochloride;
2-(3-[3',4'-Dimethylphenyl]-2-hydroxyphenyl)-9-hydroxy-naphth[1,2-d]imidazole-7-sulfonic acid hydrochloride;
2-(3-[3'-Trifluoromethylphenyl]-2-hydroxyphenyl)-9-hydroxy-naphth[1,2-d]imidazole-7-sulfonic acid hydrochloride;
2-(3-[4'-Fluorophenyl]-2-hydroxyphenyl)-9-hydroxy-naphth[1,2-d]imidazole-7-sulfonic acid hydrochloride;
2-(3-[4'-Chlorophenyl]-2-hydroxyphenyl)-9-hydroxy-naphth[1,2-d]imidazole-7-sulfonic acid hydrochloride;
2-(3-[1'-Dibenzofuranyl]-2-hydroxyphenyl)-9-hydroxy-naphth[1,2-d]imidazole-7-sulfonic acid hydrochloride;
2-(3-[1'-Naphthalenyl]-2-hydroxyphenyl)-9-hydroxy-naphth[1,2-d]imidazole-7-sulfonic acid hydrochloride;
2-(3-[3'-Chlorophenyl]-2-hydroxyphenyl)-9-hydroxy-naphth[1,2-d]imidazole-7-sulfonic acid hydrochloride;
2-(3-[3'-Nitrophenyl]-2-hydroxyphenyl)-9-hydroxy-naphth[1,2-d]imidazole-7-sulfonic acid hydrochloride;
2-(3-phenyl-2-hydroxyphenyl)-9-hydroxy-naphth[1,2-d]imidazole-7-sulfonic acid hydrochloride;
2-(4-[2'-Methylphenyl]-2-hydroxyphenyl)-9-hydroxy-naphth[1,2-d]imidazole-5-sulfonic acid hydrochloride;
2-(4-[4'-Methylphenyl]-2-hydroxyphenyl)-9-hydroxy-naphth[1,2-d]imidazole-5-sulfonic acid hydrochloride;
2-(4-[3'-Hydroxyphenyl]-2-hydroxyphenyl)-9-hydroxy-naphth[1,2-d]imidazole-5-sulfonic acid hydrochloride;
2-(4-[4'-Fluorophenyl]-2-hydroxyphenyl)-9-hydroxy-naphth[1,2-d]imidazole-5-sulfonic acid hydrochloride;
2-(4-[4'-Chlorophenyl]-2-hydroxyphenyl)-9-hydroxy-naphth[1,2-d]imidazole-5-sulfonic acid hydrochloride;
2-(4-[1'-Dibenzofuranyl]-2-hydroxyphenyl)-9-hydroxy-naphth[1,2-d]imidazole-5-sulfonic acid hydrochloride;
2-(4-[1'-Naphthalenyl]-2-hydroxyphenyl)-9-hydroxy-naphth[1,2-d]imidazole-5-sulfonic acid hydrochloride;
2-(4-[3'-Chlorophenyl]-2-hydroxyphenyl)-9-hydroxy-naphth[1,2-d]imidazole-5-sulfonic acid hydrochloride;
2-(4-[3'-Nitrophenyl]-2-hydroxyphenyl)-9-hydroxy-naphth[1,2-d]imidazole-5-sulfonic acid hydrochloride;
2-(4-phenyl-2-hydroxyphenyl)-9-hydroxy-naphth[1,2-d]imidazole-5-sulfonic acid hydrochloride;
2-(4-[2'-Methylphenyl]-2-hydroxyphenyl)-9-hydroxy-naphth[1,2-d]imidazole-7-sulfonic acid hydrochloride;
2-(4-[4'-Methylphenyl]-2-hydroxyphenyl)-9-hydroxy-naphth[1,2-d]imidazole-7-sulfonic acid hydrochloride;
2-(4-[3'-Hydroxyphenyl]-2-hydroxyphenyl)-9-hydroxy-naphth[1,2-d]imidazole-7-sulfonic acid hydrochloride;
2-(4-[4'-Fluorophenyl]-2-hydroxyphenyl)-9-hydroxy-naphth[1,2-d]imidazole-7-sulfonic acid hydrochloride;
2-(4-[4'-Chlorophenyl]-2-hydroxyphenyl)-9-hydroxy-naphth[1,2-d]imidazole-7-sulfonic acid hydrochloride;
2-(4-[1'-Dibenzofuranyl]-2-hydroxyphenyl)-9-hydroxy-naphth[1,2-d]imidazole-7-sulfonic acid hydrochloride;
2-(4-[1'-Naphthalenyl]-2-hydroxyphenyl)-9-hydroxy-naphth[1,2-d]imidazole-7-sulfonic acid hydrochloride;
2-(4-[3'-Chlorophenyl]-2-hydroxyphenyl)-9-hydroxy-naphth[1,2-d]imidazole-7-sulfonic acid hydrochloride;
2-(4-[3'-Nitrophenyl]-2-hydroxyphenyl)-9-hydroxy-naphth[1,2-d]imidazole-7-sulfonic acid hydrochloride;
2-(4-phenyl-2-hydroxyphenyl)-9-hydroxy-naphth[1,2-d]imidazole-7-sulfonic acid hydrochloride;
2-(3-phenyl-2-methoxyphenyl)-9-hydroxy-naphth[1,2-d]imidazole-7-carboxylic acid hydrochloride;
2-(3-[3',4'-dimethylphenyl]-2-methoxyphenyl)-9-hydroxy-naphth[1,2-d]imidazole-7-carboxylic acid trifluoroacetate;
2-(3-[3',4'-dimethylphenyl]-2-hydroxyphenyl)-9-hydroxy-naphth[1,2-d]imidazole-7-carboxylic acid trifluoroacetate;
2-(1-[3,4-dimethylphenyl]-3-methyl-5-hydroxy-1H-pyrrazole-4-yl)-9-hydroxy-3H-naphth[1,2-d]imidazole-7-carboxylic acid trifluoroacetate;
2-(1-hydroxy-2-naphthalenyl)-9-hydroxy-naphth[1,2-d]imidazole-7-carboxylic acid trifluoroacetate;
2-(2-pyridinyl)-9-hydroxy-naphth[1,2-d]imidazole-7-carboxylic acid trifluoroacetate;
2-(3',4'-dimethylbiphenyl-3-yl)-9-hydroxy-3H-naphtho[1,2-d]imidazole-7-sulfonic acid hydrochloride;
2-biphenyl-4-yl-9-hydroxy-3H-naphtho[1,2-d]imidazole-7-sulfonic acid hydrochloride;
2-(3',4'-dimethylbiphenyl-4-yl)-9-hydroxy-3H-naphtho[1,2-d]imidazole-7-sulfonic acid trifluoroacetate;
2-(4'-tert-butylbiphenyl-3-yl)-9-hydroxy-3H-naphtho[1,2-d]imidizole-7-sulfonic acid trifluoroacetate;
2-[3-(4-tert-butylbenzyloxy)-phenyl]-9-hydroxy-3H-naphtho[1,2-d]imidizole-7-sulfonic acid hydrochloride;
2-[3-(3-trifluoromethylbenzyloxy)-phenyl]-9-hydroxy-3H-naphtho[1,2-d]imidizole-7-sulfonic acid hydrochloride;
2-[3-(3,4-dimethylbenzyloxy)-phenyl]-9-hydroxy-3H-naphtho[1,2-d]imidizole-7-sulfonic acid hydrochloride;
2-(3',4'-dimethylbiphenyl-3-yl)-9-hydroxy-3H-naphtho[1,2-d]imidazole-7-carboxylic acid hydrochloride;
2-(3',4'-dimethylbiphenyl-4-yl)-9-hydroxy-3H-naphtho[1,2-d]imidazole-7-carboxylic acid trifluoroacetate;
2-(4'-tert-butylbiphenyl-3-yl)-9-hydroxy-3H-naphtho[1,2-d]imidazole-7-carboxylic acid trifluoroacetate;
9-hydroxy-2-(3-phenoxyphenyl)-3H-naphtho[1,2-d]imidazole-7-carboxylic acid trifluoroacetate;
3-[2-(3',4'-dimethylbiphenyl-3-yl)-9-hydroxy-3H-naphtho[1,2-d]imidazole-7-sulfonylamino]-benzoic acid;
1-[2-(3',4'-dimethylbiphenyl-3-yl)-9-hydroxy-3H-naphtho[1,2-d]imidazole-7-sulfonyl]-piperidine-3-carboxylic acid;
(S)-1-[2-(3',4'-dimethyl-biphenyl-3-yl)-9-hydroxy-3H-naphtho[1,2-d]imidazole-7-sulfonyl]-pyrrolidine-2-carboxylic acid;
({1-[2-(3',4'-dimethylbiphenyl-3-yl)-9-hydroxy-3H-naphtho[1,2-d]imidazol-7-yl]-methanoyl}-amino)-acetic acid;
(S)-2-({1-[2-(3',4'-dimethylbiphenyl-3-yl)-9-hydroxyl-3H-naphtho[1,2-d]imidazol-7-yl]-methanoyl}-amino)-propionic acid;
({1-[2-(3',4'-dimethylbiphenyl-3-yl)-9-hydroxyl-3H-naphtho[1,2-d]imidazol-7-yl]-methanoyl}-methylamino)-acetic acid;

(S)-1-{1-[2-(3',4'-dimethylbiphenyl-3-yl)-9-hydroxyl-3H-naphtho[1,2-d]imidazol-7-yl]-methanoyl}-pyrrolidine-2-carboxylic acid;
(S)-2-({1-[2-(4'tert-butyllbiphenyl-3-yl)-9-hydroxy-3H-naphtho[1,2-d]imidazol-7-yl]-methanoyl}-amino)-pentanedioic acid;
2-[6-(4-tert-butylphenyl)-pyridin-2-yl]-9-hydroxy-3H-naphtho[1,2-d]imidazole-7-carboxylic acid;
2-[5-(3,4-dichlorophenyl)furan-2-yl]-9-hydroxy-3H-naphtho[1,2-d]imidazole-7-carboxylic acid;
2-[5-benzo[b]thiophen-2-yl-furan-2-yl]-9-hydroxy-3H-naphtho[1,2-d]imidazole-7-carboxylic acid;
9-Hydroxy-2-[5-(4-tert-butylphenyl)-furan-2-yl]-3H-naphtho[1,2-d]imidazole-7-carboxylic acid;
9-Hydroxy-2-[4-(4-tert-butylphenyl)-furan-2-yl]-3H-naphtho[1,2-d]imidazole-7-carboxylic acid;
2-[5-(3,4-dimethylphenyl)-furan-2-yl]-9-hydroxy-3H-naphtho[1,2-d]imidazole-7-carboxylic acid;
2-[4-(3,4-dimethylphenyl)-furan-2-yl]-9-hydroxy-3H-naphtho[1,2-d]imidazole-7-carboxylic acid;
2-[5-(4-tert-butylphenyl)-thiophen-2-yl]-9-hydroxy-3H-naphtho[1,2-d]imidazole-7-carboxylic acid;
2-[4-(4-tert-butylphenyl)-thiophen-2-yl]-9-hydroxy-3H-naphtho[1,2-d]imidazole-7-carboxylic acid;
2-[5-(3,4-dimethylphenyl)-thiophen-2-yl]-9-hydroxy-3H-naphtho[1,2-d]imidazole-7-carboxylic acid;
2-[4-(3,4-dimethylphenyl)-thiophen-2-yl]-9-hydroxy-3H-naphtho[1,2-d]imidazole-7-carboxylic acid;
2-[4'-tert-butyl-6-methoxybiphenyl-3-yl]-9-hydroxy-3H-naphtho[1,2-d]imidazole-7-carboxylic acid;
2-[4'-tert-butyl-6-fluoro-biphenyl-3-yl]-9-hydroxy-3H-naphtho[1,2-d]imidazole-7-carboxylic acid;
2-[4'-tert-butyl-4-fluorobiphenyl-3-yl]-9-hydroxy-3H-naphtho[1,2-d]imidazole-7-carboxylic acid;
2-[6-fluoro-3',4'-dimethylbiphenyl-3-yl]-9-hydroxy-3H-naphtho[1,2-d]imidazole-7-carboxylic acid;
2-[4-fluoro-3',4'-dimethylbiphenyl-3-yl]-9-hydroxy-3H-naphtho[1,2-d]imidazole-7-carboxylic acid;
2-[4'-trifluoromethylbiphenyl-3-yl]-9-hydroxy-3H-naphtho[1,2-d]imidazole-7-carboxylic acid;
9-Hydroxy-2-[5-(3-isopropylphenyl)-furan-2-yl]-3H-naphtho[1,2-d]imidazole-7-carboxylic acid;
9-Hydroxy-2-[4-(4-tert-butylphenyl)-furan-2-yl]-3H-naphtho[1,2-d]imidazole-7-carboxylic acid;
9-Hydroxy-2-[5-(4-tert-butylphenyl)-furan-2-yl]-3H-naphtho[1,2-d]imidazole-7-carboxylic acid;
2-[5-(3,4-dimethylphenyl)-thiophen-2-yl]-9-hydroxy-3H-naphtho[1,2-d]imidazole-7-carboxylic acid;
2-[4-(3,4-dimethylphenyl)-thiophen-2-yl]-9-hydroxy-3H-naphtho[1,2-d]imidazole-7-carboxylic acid;
2-[4-(4-tert-butylphenyl)-thiophen-2-yl]-9-hydroxy-3H-naphtho[1,2-d]imidazole-7-carboxylic acid;
2-[5-(4-tert-butylphenyl)-thiophen-2-yl]-9-hydroxy-3H-naphtho[1,2-d]imidazole-7-carboxylic acid;
2-[5-(3,4-dichlorophenyl)furan-2-yl]-9-hydroxy-3H-naphtho[1,2-d]imidazole-7-carboxylic acid;
2-[5-benzo[b]thiophen-2-yl-furan-2-yl]-9-hydroxy-3H-naphtho[1,2-d]imidazole-7-carboxylic acid;
2-[41tert-butyl-6-methoxybiphenyl-3-yl]-9-hydroxy-3H-naphtho[1,2-d]imidazole-7-carboxylic acid;
2-[6-fluoro-3',4'-dimethylbiphenyl-3-yl]-9-hydroxy-3H-naphtho[1,2-d]imidazole-7-carboxylic acid;
2-[4-fluoro-3',4'-dimethylbiphenyl-3-yl]-9-hydroxy-3H-naphtho[1,2-d]imidazole-7-carboxylic acid;
2-[4'-tert-butyl-4-fluorobiphenyl-3-yl]-9-hydroxy-3H-naphtho[1,2-d]imidazole-7-carboxylic acid;
2-[4'-trifluoromethylbiphenyl-3-yl]-9-hydroxy-3H-naphtho[1,2-d]imidazole-7-carboxylic acid;
2-[4'-tert-butyl-6-fluoro-biphenyl-3-yl]-9-hydroxy-3H-naphtho[1,2-d]imidazole-7-carboxylic acid;
2-[5-(4-tert-butylphenyl)-pyridin-3-yl]-9-hydroxy-1H-naphtho[1,2-d]imidazole-7-carboxylic acid;
2-[(2-fluoro-4-trifluoromethylbiphenyl)-3-yl]-9-hydroxy-1H-naphtho[1,2-d]imidazole-7-carboxylic acid;
2-[(2,5-difluoro-4-trifluoromethylbiphenyl)-3-yl]-9-hydroxy-1H-naphtho[1,2-d]imidazole-7-carboxylic acid;
2-[(4-fluoro-4'-trifluoromethylbiphenyl)-3-yl]-9-hydroxy-1H-naphtho[1,2-d]imidazole-7-carboxylic acid;
2-[5-(4-trifluoromethylphenyl)-furan-2-yl]-9-hydroxy-3H-naphtho[1,2-d]imidazole-7-carboxylic acid;
2-[4-(4-trifluoromethylphenyl)-thiophen-2-yl]-9-hydroxy-3H-naphtho[1,2-d]imidazole-7-carboxylic acid;
2-(4'-ethylbiphenyl-3-yl)-9-hydroxy-3H-naphtho[1,2-d]imidazole-7-carboxylic acid;
2-(4'-propylbiphenyl-3-yl)-9-hydroxy-3H-naphtho[1,2-d]imidazole-7-carboxylic acid;
2-(4'-butylbiphenyl-3-yl)-9-hydroxy-3H-naphtho[1,2-d]imidazole-7-carboxylic acid;
2-(4'-carboxy-3'-methylbiphenyl-3-yl)-9-hydroxy-3H-naphtho[1,2-d]imidazole-7-carboxylic acid;
2-(4'-cyano-3'-methylbiphenyl-3-yl)-9-hydroxy-3H-naphtho[1,2-d]imidazole-7-carboxylic acid;
2-(4'-fluoro-3'-methylbiphenyl-3-y)-9-hydroxy-3H-naphtho[1,2-d]imidazole-7-carboxylic acid;
2-[1-(4-tert-butylphenyl)-1H-pyrazol-4-yl]-9-hydroxy-3H-naphtho[1,2-d]imidazole-7-carboxylic acid;
2-(3',4'-difluorobiphenyl-3-yl)-9-hydroxy-3H-naphtho[1,2-d]imidazole-7-carboxylic acid; and
2-[3-(9H-fluoren-2-yl)-phenyl]-9-hydroxy-3H-naphtho[1,2-d]imidazole-7-carboxylic acid, and
pharmaceutically acceptable salts, hydrates, solvates and esters thereof.

By the term "protected hydroxy" or "protected —OH" as used herein, is meant the alcoholic or carboxylic-OH groups which can be protected by conventional blocking groups in the art as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbons is 3 the aromatic ring contains at least two heteroatoms and when the number of carbon atoms is 4 the aromatic ring contains at least one heteroatom.

By the term "$C_1$–$C_{12}$aryl" as used herein, unless otherwise defined, is meant phenyl, naphthalene, 3,4-methylenedioxyphenyl, pyridine, biphenyl, quinoline, pyrimidine, quinazoline, thiophene, furan, pyrrole, pyrazole, imidazole and tetrazole.

By the term "substituted" as used herein, unless otherwise defined, is meant that the subject chemical moiety has one or more substituents selected from the group consisting of: hydroxyalkyl, alkoxy, acyloxy, alkyl, amino, N-acylamino, hydroxy, —$(CH_2)_gC(O)OR^6$, —$S(O)_nR^7$, nitro, cyano, halogen, trifluoromethyl and protected —OH, where g is 0–6, $R^6$ is hydrogen or alkyl, n is 0–2, and $R^7$ is hydrogen or alkyl.

By the term "alkoxy" as used herein is meant -Oalkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$–$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O)alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "N-acylamino" as used herein is meant —N(H)C(O)alkyl, where alkyl is as described herein. Examples of N-acylamino substituents as used herein include: —$N(H)C(O)CH_3$, —$N(H)C(O)CH(CH_3)_2$ and —$N(H)C(O)(CH_2)_3CH_3$.

By the term "aryloxy" as used herein is meant —$OC_6$–$C_{12}$aryl where $C_6$–$C_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifuloromethyl, acyloxy, amino, N-acylamino, hydroxy, —$(CH_2)_gC(O)OR^6$, —$S(O)_nR^7$, nitro, cyano, halogen and protected —OH, where g is 0–6, $R^6$ is hydrogen or alkyl, n is 0–2 and $R^7$ is hydrogen or alkyl. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain having $C_1$–$C_{12}$ carbon atoms. Examples of alkyl substituents as used herein include: —$CH_3$, —$CH_2$—$CH_3$, —$CH_2$—$CH_2$—$CH_3$, —$CH(CH_3)_2$, —$C(CH_3)_3$, —$(CH_2)_3$—$CH_3$, —$CH_2$—$CH(CH_3)_2$ and —$CH(CH_3)$—$CH_2$—$CH_3$, —$CH=CH_2$.

By the term "treating" and derivatives thereof as used herein, is meant prophylatic or therapeutic therapy.

All publications, including but not limited to patents and patent applications, cited in this specification are herein incorporated by reference as though fully set forth.

Compounds of Formula (II) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

As used above and throughout the remainder of the specification and claims the rings of the naphthimidazole derivatives are lettered as follows:

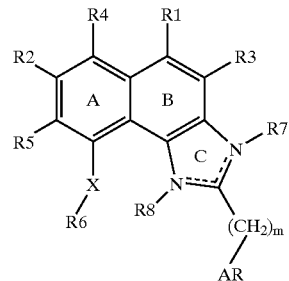

The novel compounds of Formula I are prepared analogously to the processes shown in Schemes I to III below wherein $R^1$, $R^2$, $R^3$, $R^4$, $R^5$, $R^6$, $R^7$, $R^8$, m and AR are as defined in Formula I and provided that the 'R', m or AR substituents do not include any such substituents that render inoperative the Schemes I to III processes. All of the starting materials are commercially available or are readily made from commercially available starting materials by those of skill in the art.

Scheme 1

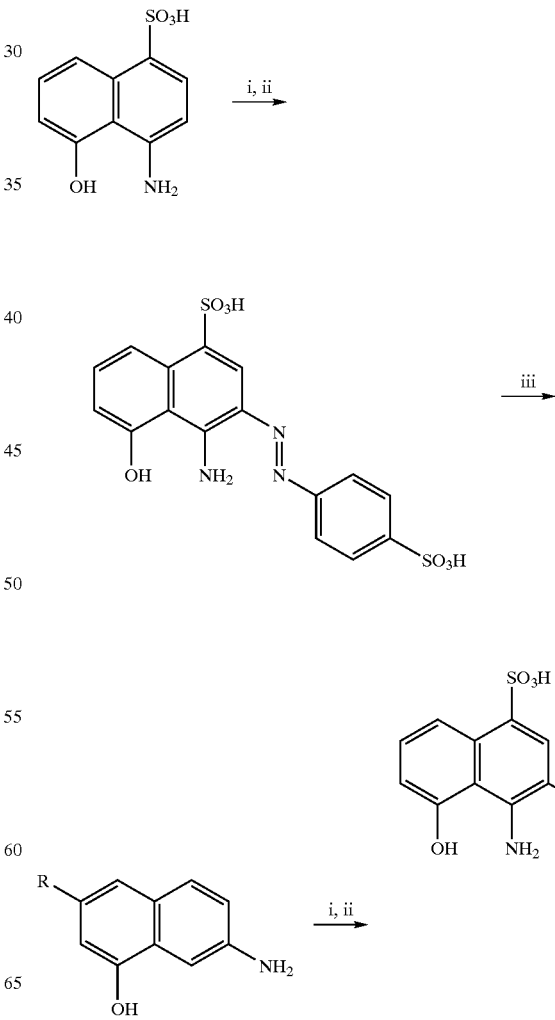

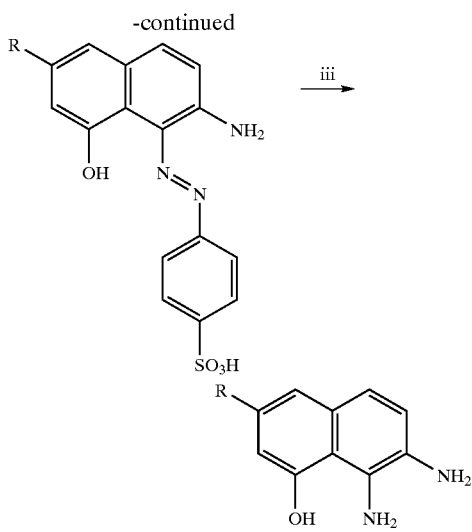

When R=SO3H i) 4-amino-1-benzenesulfonic acid, NaNO$_2$, NaHCO$_3$, water; ii) HCl, ice; iii) Na$_2$S$_2$O$_4$, heat.
When R=CO$_2$H i) 4-amino-1-benzenesulfonic acid, NaNO$_2$, NaHCO$_3$, water; ii) HCl, ice; iii) SnCl$_2$, Aq. HCl, heat.

Scheme I outlines the preparation of the diamines used in the formation of Formula I compounds as shown in scheme 3. The diamino compounds are prepared by diazo coupling of 4-benzenediazonium sulfate with the appropriate aminohydroxy naphthalene sulfonic acid under aqueous acidic conditions. The resulting diazo compounds are then reduced by sodium hydrogen sulfite in water to yield the corresponding diamines as their dihydrochloride salts.

Scheme 2

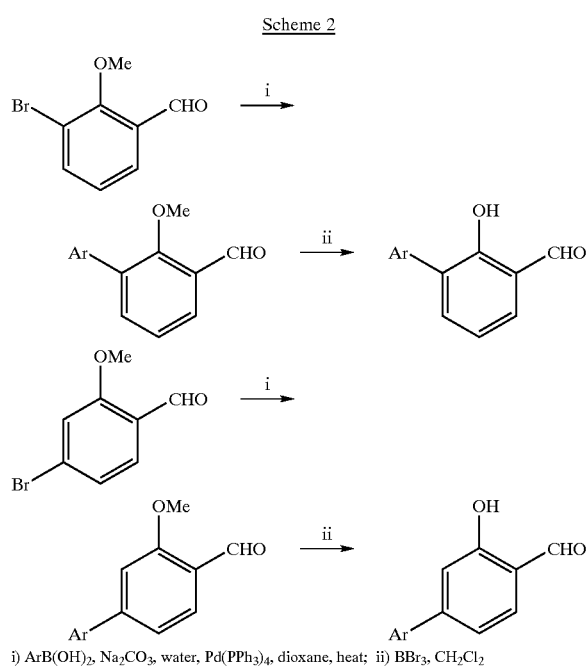

i) ArB(OH)$_2$, Na$_2$CO$_3$, water, Pd(PPh$_3$)$_4$, dioxane, heat; ii) BBr$_3$, CH$_2$Cl$_2$ Scheme II outlines the formation of biaryl methoxy (or hydroxy) aldehydes for use in the preparation of Formula I compounds as shown in scheme 3. A bromo methoxy aldehyde is subjected to Suzuki coupling conditions using an appropriate boronic acid such as 4-methylphenylboronic acid, in an appropriate solvent system such as dioxane and 1N aqueous sodium carbonate. Palladium tetrakis triphenyl phosphine was used as the catalyst in the coupling reaction. A portion of the biaryl methoxy aldehyde is then subjected to demethylation conditions using boron tribromide in methylene chloride at room temperature.

As used in Scheme II, the above benzene moiety can be replaced by another moiety such as: furan, thiophene, pyridine, pyrazole and thiazole.

Scheme 3

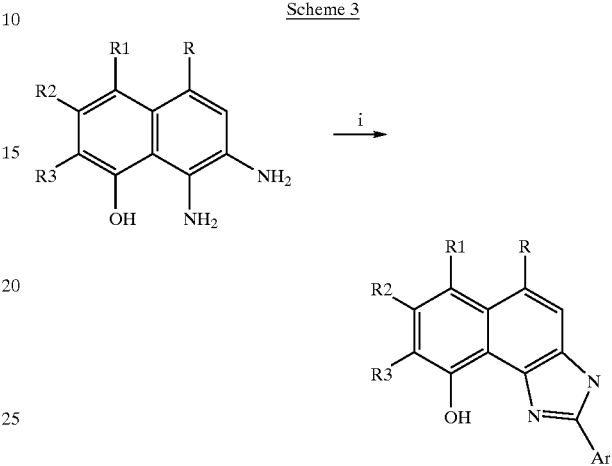

i) ArCHO, EtOH, HaHSO$_3$, water

Scheme III outlines a preparation of compounds of Formula I. A diamino-hydroxy naphthalene sulfonic acid prepared by the method of Scheme I is treated with 1.1 Eq. of a biaryl methoxy or hydroxy aldehyde prepared by the method of Scheme 2. The reaction is run in the presence of a dehydrogenation reagent such as sodium pyrosulfite in a suitable solvent such as aqueous ethanol at 50° C. overnight to afford the desired naphthimidazole. Typically the precipitated naphthimidazole can then be filtered off and successive washings with water (to remove unwanted sodium salts) followed by ethyl eacetate (to remove unreacted aldehyde) provide compounds of formula I in >80% purity.

The treatment of thrombocytopenia, as described herein, is accomplished by enhancing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. Preferably, if the administration is not simultaneous, the compounds are administered in a close time proximity to each other. Furthermore, it does not matter if the compounds are administered in the same dosage form, e.g. one compound may be administered topically and another compound may be administered orally.

Because the pharmaceutically active compounds of the present invention are active as TPO mimetics they exhibit therapeutic utility in treating thrombocytopenia and other conditions with depressed platelet production.

In determining potency as TPO mimetics, the following assays were employed:

Luciferase Assay

Compounds of the present invention were tested for potency as mimetics of the TPO receptor in a Luciferase assay such as described in Lamb, et al., *Nucleic Acids Research* 23; 3283–3289 (1995) and Seidel, et al., *Proc.*

Natl. Acad. Sci., USA 92: 3041–3045 (1995) by substituting a TPO-responsive BaF3 cell line (Vigon et al. Proc. Natl. Acad. Sci. USA 1992, 89, 5640–5644) for the HepG2 cells utilized therein. The murine BaF3 cells express TPO receptors and closely match the pattern of STAT (signal transducers and activators of transcription) activation observed in primary murine and human bone marrow cells.

Some of the most preferred compounds of this invention were also active in an in vitro proliferation assay using the murine 32D-mpl cell line (Bartley, T. D. et al., Cell, 1994, 77, 1117–1124). 32D-mpl cells express Tpo-R and their survival is dependent on the presence of TPO. Likewise, some of the most preferred compounds of this invention were also positive in stimulating the maturation of megakaryocytes from human bone marrow cells. In this assay, purified human CD34+ progenitor cells were incubated in liquid culture with test compounds for 10 days and the number of cells expressing the transmembrane glycoprotein CD41 (gpIIb), a megakaryocytic marker, was then measured by flow cytometry (see Cwirla, S. E. et al Science, 1997, 276, 1696–1699).

The pharmaceutically active compounds within the scope of this invention are useful as TPO mimetics in mammals, including humans, in need thereof.

Some of the preferred compounds within the scope of the invention showed activation from about 4% to 130% control at a concentration of 0.01–10 uM in the luciferase assay. The preferred compounds of the invention also promoted the proliferation of 32D-mpl cells at a concentration of 0.01 to 100 uM. The preferred compounds of the invention also showed activity in the CD41 megakaryocytic assay at a concentration of 0.01 to 30 uM.

Within the scope of the invention Compound 14 showed activation of about 25% of control (control is the maximal response to TPO) at a concentration of 2 uM in the luciferase assay.

The present invention therefor provides a method of treating thrombocytopenia and other conditions with depressed platelet production, which comprises administering a compound of Formula (I)), as described above, in a quantity effective to enhance platelet production. The compounds of Formula (I) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a TPO mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (I) in the manufacture of a medicament for use as a TPO mimetic.

The invention also provides for the use of a compound of Formula (I) in the manufacture of a medicament for use in therapy.

The invention also provides for the use of a compound of Formula (I) in the manufacture of a medicament for use in enhancing platelet production.

The invention also provides for the use of a compound of Formula (I) in the manufacture of a medicament for use in treating thrombocytopenia.

The invention also provides for a pharmaceutical composition for use as a TPO mimetic which comprises a compound of Formula (I) and a pharmaceutically acceptable carrier.

The invention also provides for a pharmaceutical composition for use in the treatment of thrombocytopenia which comprises a compound of Formula (I) and a pharmaceutically acceptable carrier.

The invention also provides for a pharmaceutical composition for use in enhancing platelet production which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Without further elaboration, it is believed that one skilled in the art can, using the preceding description, utilize the present invention to its fullest extent. The following Examples are, therefore, to be construed as merely illustrative and not a limitation of the scope of the present invention in any way.

Experimental Details

EXAMPLE 1

Preparation of 2-(3-[2'-Methylphenyl]-2-methoxyphenyl)-9-hydroxy-naphth[1,2-d]imidazole-5-sulfonic acid hydrochloride (Compound 1)

a) 2-methoxy-3-(2'-methylphenyl)benzaldehyde:

A solution of 3-bromo-2-methoxybenzaldehyde (0.43 g, 2 mmol), 2-methylphenylboronic acid (0.326 g, 2.4 mmol), 2M aqu. sodium carbonate (2 mL, 4 mmol) and tetrakistriphenylphosphinopalladium(0) (0.025 g) in 1,4-dioxane (30 mL) was stirred and heated under reflux under a nitrogen atmosphere for 24 h.

The reaction mixture was cooled and suspended between ethyl acetate and 3M aqu. hydrochloric acid (30 mL). The phases were separated and the aqueous phase was further extracted with ethyl acetate (3 times). The combined organic layers were dried over anhydrous $MgSO_4$ and concentrated under reduced pressure to give the title product. (0.42 g, 80%). MS(ES) m/z 227 [M+H].

Follow the procedure of example 1a), except substituting
4-methylphenylboronic acid
3,4-dimethylphenylboronic acid
3-methoxyphenylboronic acid
3-trifluoromethylphenylboronic acid
4-fluorophenylboronic acid
4-chlorophenylboronic acid
1-dibenzofuranylboronic acid
1-naphthalenylboronic acid
3-chlorophenylboronic acid
3-nitrophenylboronic acid
3-phenylboronic acid for 4-methylphenylboronic acid, the following compounds were generated:
2-methoxy-3-(4'-methylphenyl)benzaldehyde, MS(ES) m/z 227 [M+H].
2-methoxy-3-(3',4'-dimethylphenyl)benzaldehyde, MS(ES) m/z 241 [M+H].
2-methoxy-3-(3'-methoxyphenyl)benzaldehyde, MS(ES) m/z 243 [M+H].
2-methoxy-3-(3'-trifluoromethylphenyl)benzaldehyde, MS(ES) m/z 281 [M+H].
2-methoxy-3-(4'-fluorophenyl)benzaldehyde, MS(ES) m/z 231 [M+H].
2-methoxy-3-(4'-chlorophenyl)benzaldehyde, MS(ES) m/z 247 [M+H].
2-methoxy-3-(1'-dibenzofuranyl)benzaldehyde, MS(ES) m/z 303 [M+H], 605 [2M+H]
2-methoxy-3-(1'-naphthalenyl)benzaldehyde, MS(ES) m/z 263 [M+H].
2-methoxy-3-(3'-chlorophenyl)benzaldehyde, MS(ES) m/z 247 [M+H].
2-methoxy-3-(3'-nitrophenyl)benzaldehyde, MS(ES) m/z 258 [M+H].
2-methoxy-3-phenylbenzaldehyde, MS(ES) m/z 213 [M+H].

b) 3,4-Diamino-5-hydroxy-1-naphthalene sulfonic acid dihydrochloride:

A stirred solution of p-benzenediazonium sulfonic acid, was prepared by the addition of sodium sulfanilate (1.10 g, 5.2 mmole) to sodium nitrite (0.40 g, 5.7 mmole) in water (10 mL) followed by addition of ice (6.0 g) and concentrated HCl (1.1 mL, 37%). After 30 min. of standing at 0° C. 4-amino-5-hydroxy-1-naphthalene sulfonic acid (1.2 g, 5.2 mmole) was added in water (10 mL) and the reaction was stirred at room temperature over 18 hours. The reaction mixture was warmed to 50° C. and sodium hydrosulfite (3.0 g, 15.6 mmole) was added and the reaction was stirred for 4 hours. The reaction was filtered and the precipitate was washed with water, methanol, and ether to give the title compound (0.64 g; 53%) as a red solid. MS(ES) m/z 255 [M+H].

c) 2-(3-[2'-Methylphenyl]-2-methoxyphenyl)-9-hydroxy-naphth[1,2-d]imidazole-5-sulfonic acid hydrochloride:

To an agitated solution of 2-methoxy-3-(2'-methylphenyl) benzaldehyde (0.030 g, 0.14 mmol) in EtOH (0.80 mL) was added 3,4-diamino-5-hydroxy-1-naphthalene sulfonic acid dihydrochloride (0.033 g, 0.10 mmol) and sodium bisulfite (30 mg) in water (0.20 mL). The solution was heated to 60° C. and agitated overnight. The solution was cooled to room temperature, the tan precipitate was isolated by filtration and washed with water and ethyl acetate to provide the title compound (0.039 g, 78%) MS(ES) m/z 459 [M−H].

Following the same procedure of Example 1b), except substituting:
2-methoxy-3-(4'-methylphenyl)benzaldehyde
2-methoxy-3-(3',4'-dimethylphenyl)benzaldehyde
2-methoxy-3-(3'-methoxyphenyl)benzaldehyde
2-methoxy-3-(3'-trifluoromethylphenyl)benzaldehyde
2-methoxy-3-(4'-fluorophenyl)benzaldehyde
2-methoxy-3-(4'-chlorophenyl)benzaldehyde
2-methoxy-3-(1'-dibenzofuranyl)benzaldehyde
2-methoxy-3-(1'-naphthalenyl)benzaldehyde
2-methoxy-3-(3'-chlorophenyl)benzaldehyde
2-methoxy-3-(3'-nitrophenyl)benzaldehyde
2-methoxy-3-phenylbenzaldehyde for 2-methoxy-3-(2'-methylphenyl)benzaldehyde the following compounds were generated:

Compound 2: 2-(3-[4'-Methylphenyl]-2-methoxyphenyl)-9-hydroxy-naphth[1,2-d]imidazole-5-sulfonic acid hydrochloride, (0.030 g, 60%) MS(ES) m/z 459 [M−H].

Compound 3: 2-(3-[3',4'-Dimethylphenyl]-2-methoxyphenyl)-9-hydroxy-naphth[1,2-d]imidazole-5-sulfonic acid hydrochloride, (0.020 g, 39%) MS(ES) m/z 473 [M−H].

Compound 4: 2-(3-[3'-Methoxyphenyl]-2-methoxyphenyl)-9-hydroxy-naphth[1,2-d]imidazole-5-sulfonic acid hydrochloride, (0.028 g, 55%) MS(ES) m/z 475 [M−H].

Compound 5: 2-(3-[3'-Trifluoromethylphenyl]-2-methoxyphenyl)-9-hydroxy-naphth[1,2-d]imidazole-5-sulfonic acid hydrochloride, (0.018 g, 33%) MS(ES) m/z 513 [M−H].

Compound 6: 2-(3-[4'-Fluorophenyl]-2-methoxyphenyl)-9-hydroxy-naphth[1,2-d]imidazole-5-sulfonic acid hydrochloride, (0.032 g, 64%) MS(ES) m/z 463 [M−H].

Compound 7: 2-(3-[4'-Chlorophenyl]-2-methoxyphenyl)-9-hydroxy-naphth[1,2-d]imidazole-5-sulfonic acid hydrochloride, (0.029 g, 56%). $^1$H NMR (400 MHz, DMSO-$d_6$) δ 8.46 (d, J=8.7 Hz, 1H), 8.36 (s, 1H), 8.13 (d, J=6.5 Hz, 1H), 7.68 (d, J=8.5 Hz, 2H), 7.67 (s, 1H), 7.59 (d, J=8.5 Hz, 2H), 7.55 (m, 2H), 7.14 (d, J=7.7 Hz, 1H), 3.38 (s, 3H). MS(ES) m/z 479, 481 [M−H].

Compound 8: 2-(3-[1'-Dibenzofuranyl]-2-methoxyphenyl)-9-hydroxy-naphth[1,2-d]imidazole-5-sulfonic acid hydrochloride, (0.035 g, 61%) MS(ES) m/z 535 [M−H].

Compound 9: 2-(3-[1'-Naphthalenyl]-2-methoxyphenyl)-9-hydroxy-naphth[1,2-d]imidazole-5-sulfonic acid hydrochloride, (0.034 g, 64%) MS(ES) m/z 495 [M−H].

Compound 10: 2-(3-[3'-Chlorophenyl]-2-methoxyphenyl)-9-hydroxy-naphth[1,2-d]imidazole-5-sulfonic acid hydrochloride, (0.031 g, 60%) MS(ES) m/z 479, 481 [M−H].

Compound 11: 2-(3-[3'-Nitrophenyl]-2-methoxyphenyl)-9-hydroxy-naphth[1,2-d]imidazole-5-sulfonic acid hydrochloride, (0.035 g, 66%) MS(ES) m/z 490 [M–H].

Compound 12: 2-(3-phenyl-2-methoxyphenyl)-9-hydroxy-naphth[1,2-d]imidazole-5-sulfonic acid hydrochloride, (0.028 g, 58%) MS(ES) m/z 445 [M–H]. $^1$H NMR (400 MHz, DMSO-$d_6$)) δ 8.49 (d, J=8.5 Hz, 1H), 8.36 (s, 1H), 8.13 (d, J=7.7 Hz, 1H), 7.6 (m, 3H), 7.49 (m, 5H), 7.15 (d, J=7.4 Hz, 1H), 3.38 (s, 3H).

EXAMPLE 2

Preparation of 2-(3-[2'-Methylphenyl]-2-methoxyphenyl)-9-hydroxy-naphth[1,2-d]imidazole-7-sulfonic acid hydrochloride (Compound 13)

a) 7,8-Diamino-1-hydroxy-3-naphthalene sulfonic acid dihydrochloride

A stirred solution of p-benzenediazonium sulfonic acid, was prepared by the addition of sodium sulfanilate (1.10 g, 5.2 mmole) to sodium nitrite (0.40 g, 5.7 mmole) in water (10 mL) followed by addition to ice (6.0 g) and concentrated HCl (1.1 mL, 37%). After 30 min. of standing at 0° C. 7-amino-1-hydroxy-3-naphthalene sulfonic acid (1.2 g, 5.2 mmole) was added in water (10 mL) and the reaction was stirred at room temperature overnight. The reaction mixture was warmed to 50° C. and sodium hydrosulfite (3.0 g, 15.6 mmole) was added and the reaction was stirred for 4 hours. The reaction was filtered and the precipitate was washed with water, methanol, and ether to give the title compound (0.54 g; 45%) as a red solid. MS(ES) m/z 255 [M+H].

b) 2-(3-[2'-Methylphenyl]-2-methoxyphenyl)-9-hydroxy-naphth[1,2-d]imidazole-7-sulfonic acid hydrochloride To an agitated solution of 2-methoxy-3-(2'-methylphenyl)benzaldehyde (0.030 g, 0.14 mmol) in EtOH (0.80 mL) was added 7,8-Diamino-1-hydroxy-3-naphthalene sulfonic acid dihydrochloride (0.033 g, 0.10 mmol) and sodium bisulfite (0.03 g) in water (0.20 mL). The solution was heated to 60° C. and agitated overnight. The solution was cooled to room temperature, the tan precipitate was isolated by filtration and washed with water and ethyl acetate to provide the title compound (0.015 g, 30%) MS(ES) m/z 459 [M–H].

Following the same procedure of Example 2b), except substituting:
2-methoxy-3-(4'-methylphenyl)benzaldehyde
2-methoxy-3-(3',4'-dimethylphenyl)benzaldehyde
2-methoxy-3-(3'-methoxyphenyl)benzaldehyde
2-methoxy-3-(3'-trifluoromethylphenyl)benzaldehyde
2-methoxy-3-(4'-fluorophenyl)benzaldehyde
2-methoxy-3-(4'-chlorophenyl)benzaldehyde
2-methoxy-3-(1'-dibenzofuranyl)benzaldehyde
2-methoxy-3-(1'-naphthalenyl)benzaldehyde
2-methoxy-3-(3'-chlorophenyl)benzaldehyde
2-methoxy-3-(3'-nitrophenyl)benzaldehyde
2-methoxy-3-phenylbenzaldehyde for 2-methoxy-3-(2'-methylphenyl)benzaldehyde, the following compounds were generated:

Compound 14: 2-(3-[4'-Methylphenyl]-2-methoxyphenyl)-9-hydroxy-naphth[1,2-d]imidazole-7-sulfonic acid hydrochloride, (0.020 g, 40%) MS(ES) m/z 459 [M–H].

Compound 15: 2-(3-[3',4'-Dimethylphenyl]-2-methoxyphenyl)-9-hydroxy-naphth[1,2-d]imidazole-5-sulfonic acid hydrochloride, (0.030 g, 59%).MS(ES) m/z 473 [M–H].

Compound 16: 2-(3-[3'-Methoxyphenyl]-2-methoxyphenyl)-9-hydroxy-naphth[1,2-d]imidazole-7-sulfonic acid hydrochloride, (0.030 g, 58%) MS(ES) m/z 475 [M–H].

Compound 17: 2-(3-[3'-Trifluoromethylphenyl]-2-methoxyphenyl)-9-hydroxy-naphth[1,2-d]imidazole-7-sulfonic acid hydrochloride, (0.025 g, 45%) MS(ES) m/z 513 [M–H].

Compound 18: 2-(3-[4'-Fluorophenyl]-2-methoxyphenyl)-9-hydroxy-naphth[1,2-d]imidazole-7-sulfonic acid hydrochloride, (0.030 g, 60%) MS(ES) m/z 463 [M–H].

Compound 19: 2-(3-[4'-Chlorophenyl]-2-methoxyphenyl)-9-hydroxy-naphth[1,2-d]imidazole-7-sulfonic acid hydrochloride, (0.020 g, 39%) MS(ES) m/z 479, 481 [M–H].

Compound 20: 2-(3-[1'-Dibenzofuranyl]-2-methoxyphenyl)-9-hydroxy-naphth[1,2-d]imidazole-7-sulfonic acid hydrochloride, (0.035 g, 61%) MS(ES) m/z 535 [M–H].

Compound 21: 2-(3-[1'-Naphthalenyl]-2-methoxyphenyl)-9-hydroxy-naphth[1,2-d]imidazole-7-sulfonic acid hydrochloride, (0.032 g, 60%) MS(ES) m/z 495 [M–H].

Compound 22: 2-(3-[3'-Chlorophenyl]-2-methoxyphenyl)-9-hydroxy-naphth[1,2-d]imidazole-7-sulfonic acid hydrochloride, (0.010 g, 19%) MS(ES) m/z 479, 481 [M–H].

Compound 23: 2-(3-[3'-Nitrophenyl]-2-methoxyphenyl)-9-hydroxy-naphth[1,2-d]imidazole-7-sulfonic acid hydrochloride, (0.020 g, 38%) $^1$H NMR (400 MHz, DMSO-$d_6$)) δ 8.5 (s, 1H), 8.33 (d, J=8.1 Hz, 1H), 8.18 (d, J=7.8 Hz, 1H), 8.14 (d, J=7.8 Hz, 1H), 8.05 (d, J=8.8 Hz, 1H)), 7.9 (m, 4H), 7.58 (t, J=7.7 Hz, 1H), 7.44 (s, 1H), 3.38 (s, 3H). MS(ES) m/z 490 [M–H].

Compound 24: 2-(3-phenyl-2-methoxyphenyl)-9-hydroxy-naphth[1,2-d]imidazole-7-sulfonic acid hydrochloride, (0.005 g, 10%) MS(ES) m/z 445 [M–H].

EXAMPLE 3

Preparation of 2-(4-[2'-Methylphenyl]-2-methoxyphenyl)-9-hydroxy-naphth[1,2-d]imidazole-5-sulfonic acid hydrochloride (Compound 25)

a) 2-methoxy-4-(2'-methylphenyl)benzaldehyde:

A solution of 4-bromo-2-methoxybenzaldehyde (0.43 g, 2 mmol), 2-methylphenylboronic acid (0.326 g, 2.4 mmol), 2M aqu. sodium carbonate (2 ml, 4 mmol) and tetrakistriphenylphosphinopalladium(0) (0.025 g) in 1,4-dioxane (30 mL) was stirred and heated under reflux under a nitrogen atmosphere for 24 h.

The reaction mixture was cooled and suspended between ethyl acetate and 3M aqu. hydrochloric acid (30 mL). The phases were separated and the aqueous phase was further extracted with ethyl acetate (3 times). The combined organic layers were dried over anhydrous MgSO$_4$ and concentrated under reduced pressure to give the title product. (0.42 g, 80%). MS(ES) m/z 227 [M+H].

Follow the procedure of example 1a), except substituting
4-methylphenylboronic acid
3,4-dimethylphenylboronic acid
3-methoxyphenylboronic acid
3-trifluoromethylphenylboronic acid
4-fluorophenylboronic acid
4-chlorophenylboronic acid
1-dibenzofuranylboronic acid
1-naphthalenylboronic acid
3-chlorophenylboronic acid
3-nitrophenylboronic acid
3-phenylboronic acid for 2-methylphenylboronic acid, the following compounds were generated:

2-methoxy-4-(4'-methylphenyl)benzaldehyde. $^1$H NMR (300 MHz, CDCl3)) δ 10.5 (s, 1H), 7.9 (d, J=7.2 Hz, 1H), 7.55 (d, J=7.8 Hz, 2H), 7.18 (m, 3H), 7.09 (s, 1H), 4.0 (s, 3H), 2.4 (s, 3H).

2-methoxy-4-(3',4'-dimethylphenyl)benzaldehyde. $^1$H NMR (300 MHz, CDCl3)) δ 10.5 (s, 1H), 7.9 (d, J=7.2 Hz, 1H), 7.40 (s, 1H), 7.38(d, J=7.8 Hz, 1H), 7.23 (d, J=7.2 Hz, 2H), 7.09 (s, 1H), 4.0 (s, 3H), 2.33 (s, 3H), 2.30 (s, 3H).

2-methoxy-4-(3'-methoxyphenyl)benzaldehyde. $^1$H NMR (300 MHz, CDCl3)) δ 10.5 (s, 1H), 7.9 (d, J=7.2 Hz, 1H), 7.4 (t, J=6.5 Hz, 1H), 7.25 (m, 4H), 7.0 (d, J=7.0 Hz, 1H), 4.1 (s, 3H), 3.9 (s, 3H).

2-methoxy-4-(3'-trifluoromethylphenyl)benzaldehyde, MS(ES) m/z 281 [M+H].

2-methoxy-4-(4'-fluorophenyl)benzaldehyde, MS(ES) m/z 231 [M+H].

2-methoxy-4-(4'-chlorophenyl)benzaldehyde, MS(ES) m/z 247 [M+H].

2-methoxy-4-(1'-dibenzofuranyl)benzaldehyde, MS(ES) m/z 303 [M+H], 605 [2M+H]

2-methoxy-4-(1'-naphthalenyl)benzaldehyde. $^1$H NMR (300 MHz, CDCl3)) δ 10.5 (s, 1H), 7.9 (m, 4H), 7.55 (m, 5H), 7.18 (d, J=7.0 Hz, 1H), 7.1 (s, 1H), 4.0 (s, 3H).

2-methoxy-4-(3'-chlorophenyl)benzaldehyde, MS(ES) m/z 247 [M+H].

2-methoxy-4-(3'-nitrophenyl)benzaldehyde, MS(ES) m/z 258 [M+H].

2-methoxy-4-phenylbenzaldehyde, MS(ES) m/z 213 [M+H].

b) 2-(4-[2'-Methylphenyl]-2-methoxyphenyl)-9-hydroxy-naphth[1,2-d]imidazole-5-sulfonic acid hydrochloride:

To an agitated solution of 2-methoxy-4-(2'methylphenyl)benzaldehyde (0.030 g, 0.14 mmol) in EtOH (0.80 mL) was added 1,2-diamino-8-hydroxy-naphthalene-4-sulfonic acid dihydrochloride (0.033 g, 0.10 0 mmol) and sodium bisulfite (0.03 g) in water (0.20 mL). The solution was heated to 60° C. and agitated overnight. The solution was cooled to room temperature, the tan precipitate was isolated by filtration and washed with water and ethyl acetate to provide the title compound (0.025 g, 50%) MS(ES) m/z 459 [M−H].

Following the same procedure of Example 3b), except substituting:
  2-methoxy-4-(4'-methylphenyl)benzaldehyde
  2-methoxy-4-(3',4'-dimethylphenyl)benzaldehyde
  2-methoxy-4-(3'-methoxyphenyl)benzaldehyde
  2-methoxy-4-(3'-trifluoromethylphenyl)benzaldehyde
  2-methoxy-4-(4'-fluorophenyl)benzaldehyde
  2-methoxy-4-(4'-chlorophenyl)benzaldehyde
  2-methoxy-4-(1'-dibenzofuranyl)benzaldehyde
  2-methoxy-4-(1'-naphthalenyl)benzaldehyde
  2-methoxy-4-(3'-chlorophenyl)benzaldehyde
  2-methoxy-4-(3'-nitrophenyl)benzaldehyde
  2-methoxy-4-phenylbenzaldehyde for 2-methoxy-4-(2'-methylphenyl)benzaldehyde the following compounds were generated:

Compound 26: 2-(4-[4'-Methylphenyl]-2-methoxyphenyl)-9-hydroxy-naphth[1,2-d]imidazole-5-sulfonic acid hydrochloride, (0.021 g, 42%) MS(ES) m/z 459 [M−H].

Compound 27: 2-(4-[3',4'-Dimethylphenyl]-2-methoxyphenyl)-9-hydroxy-naphth[1,2-d]imidazole-5-sulfonic acid hydrochloride, (0.035 g, 68%) MS(ES) m/z 473 [M−H].

Compound 28: 2-(4-[3'-Methoxyphenyl]-2-methoxyphenyl)-9-hydroxy-naphth[1,2-d]imidazole-5-sulfonic acid hydrochloride, (0.045 g, 88%) MS(ES) m/z 475 [M−H].

Compound 29: 2-(4-[3'-Trifluoromethylphenyl]-2-methoxyphenyl)-9-hydroxy-naphth[1,2-d]imidazole-5-sulfonic acid hydrochloride, (0.038 g, 69%) MS(ES) m/z 513 [M-H).

Compound 30: 2-(4-[4'-Fluorophenyl]-2-methoxyphenyl)-9-hydroxy-naphth[1,2-d]imidazole-5-sulfonic acid hydrochloride, (0.037 g, 74%) MS(ES) m/z 463 [M−H].

Compound 31: 2-(4-[4'-Chlorophenyl]-2-methoxyphenyl)-9-hydroxy-naphth[1,2-d]imidazole-5-sulfonic acid hydrochloride, (0.023 g, 44%) MS(ES) m/z 479, 481 [M−H].

Compound 32: 2-(4-[1'-Dibenzofuranyl]-2-methoxyphenyl)-9-hydroxy-naphth[1,2-d]imidazole-5-sulfonic acid hydrochloride, (0.049 g, 86%) MS(ES) m/z 535 [M−H].

Compound 33: 2-(4-[1'-Naphthalenyl]-2-methoxyphenyl)-9-hydroxy-naphth[1,2-d]imidazole-5-sulfonic acid hydrochloride, (0.018 g, 34%) MS(ES) m/z 495 [M−H].

Compound 34: 2-(4-[3'-Chlorophenyl]-2-methoxyphenyl)-9-hydroxy-naphth[1,2-d]imidazole-5-sulfonic acid hydrochloride, (0.025 g, 48%) MS(ES) m/z 479, 481 [M−H].

Compound 35: 2-(4-[3'-Nitrophenyl]-2-methoxyphenyl)-9-hydroxy-naphth[1,2-d]imidazole-5-sulfonic acid hydrochloride, (0.038 g, 72%) MS(ES) m/z 490 [M−H].

Compound 36: 2-(4-phenyl-2-methoxyphenyl)-9-hydroxy-naphth[1,2-d]imidazole-5-sulfonic acid hydrochloride, (0.033 g, 68%) MS(ES) m/z 445 [M−H].

EXAMPLE 4

Preparation of 2-(4-[2'-Methylphenyl]-2-methoxyphenyl)-9-hydroxy-naphth[1,2-d]imidazole-7-sulfonic acid hydrochloride (Compound 37)

To an agitated solution of 2-methoxy-4-(2'-methylphenyl)benzaldehyde (0.030 g, 0.14 mmol) in EtOH (0.80 mL) was added 1,2-diamino-8-hydroxy-naphthalene-6-sulfonic acid dihydrochloride (0.033 g, 0.10 mmol) and sodium bisulfite (0.03 g) in water (0.20 mL). The solution was heated to 60° C. and agitated over 18 hours. The solution was cooled to room temperature, the tan precipitate was isolated by filtration and washed with water and ethyl acetate to provide the title compound (0.010 g, 20%) MS(ES) m/z 459 [M−H].

Following the same procedure of Example 4, except substituting:
  2-methoxy-4-(4'-methylphenyl)benzaldehyde
  2-methoxy-4-(3',4'-dimethylphenyl)benzaldehyde
  2-methoxy-4-(3'-methoxyphenyl)benzaldehyde
  2-methoxy-4-(3'-trifluoromethylphenyl)benzaldehyde
  2-methoxy-4-(4'-fluorophenyl)benzaldehyde
  2-methoxy-4-(4'-chlorophenyl)benzaldehyde
  2-methoxy-4-(1'-dibenzofuranyl)benzaldehyde
  2-methoxy-4-(1'-naphthalenyl)benzaldehyde
  2-methoxy-4-(3'-chlorophenyl)benzaldehyde
  2-methoxy-4-(3'-nitrophenyl)benzaldehyde
  2-methoxy-4-phenylbenzaldehyde for 2-methoxy-4-(2'-methylphenyl)benzaldehyde the following compounds were generated:

Compound 38: 2-(4-[4'-Methylphenyl]-2-methoxyphenyl)-9-hydroxy-naphth[1,2-d]imidazole-7-sulfonic acid hydrochloride, (0.015 g, 30%) MS(ES) m/z 459 [M−H].

Compound 39: 2-(4-[3',4'-Dimethylphenyl]-2-methoxyphenyl)-9-hydroxy-naphth[1,2-d]imidazole-7-sulfonic acid hydrochloride, (0.010 g, 20%). $^1$H NMR (400 MHz, DMSO-d$_6$)) δ 8.33 (d, J=7.6 Hz, 1H), 7.85 (m, 3H), 7.64 (s, 1H), 7.56 (m, 3H), 7.36 (s, 1H), 7.28 (d, J=7.7 Hz, 1H), 2.33 (s, 3H), 2.28 (s, 3H). MS(ES) m/z 473 [M−H].

Compound 40: 2-(4-[3'-Methoxyphenyl]-2-methoxyphenyl)-9-hydroxy-naphth[1,2-d]imidazole-7-sulfonic acid hydrochloride, (0.031 g, 60%) MS(ES) m/z 475 [M−H].

Compound 41: 2-(4-[3'-Trifluoromethylphenyl]-2-methoxyphenyl)-9-hydroxy-naphth[1,2-d]imidazole-7-sulfonic acid hydrochloride, (0.027 g, 49%) MS(ES) m/z 513 [M−H].

Compound 42: 2-(4-[4'-Fluorophenyl]-2-methoxyphenyl)-9-hydroxy-naphth[1,2-d]imidazole-7-sulfonic acid hydrochloride, (0.028 g, 56%) MS(ES) m/z 463 [M−H].

Compound 43: 2-(4-[4'-Chlorophenyl]-2-methoxyphenyl)-9-hydroxy-naphth[1,2-d]imidazole-7-sulfonic acid hydrochloride, (0.008 g, 15%) MS(ES) m/z 479, 481 [M−H].

Compound 44: 2-(4-[1'-Dibenzofuranyl]-2-methoxyphenyl)-9-hydroxy-naphth[1,2-d]imidazole-7-sulfonic acid hydrochloride, (0.050 g, 87%) MS(ES) m/z 535 [M–H].

Compound 45: 2-(4-[1'-Naphthalenyl]-2-methoxyphenyl)-9-hydroxy-naphth[1,2-d]imidazole-7-sulfonic acid hydrochloride, (0.013 g, 24%) MS(ES) m/z 495 [M–H].

Compound 46: 2-(4-[3'-Chlorophenyl]-2-methoxyphenyl)-9-hydroxy-naphth[1,2-d]imidazole-7-sulfonic acid hydrochloride, (0.031 g, 60%) MS(ES) m/z 479, 481 [M–H].

Compound 47: 2-(4-[3'-Nitrophenyl]-2-methoxyphenyl)-9-hydroxy-naphth[1,2-d]imidazole-7-sulfonic acid hydrochloride, (0.026 g, 49%) MS(ES) m/z 490 [M–H].

Compound 48: 2-(4-phenyl-2-methoxyphenyl)-9-hydroxy-naphth[1,2-d]imidazole-7-sulfonic acid hydrochloride, (0.020 g, 41%). $^1$H NMR (400 MHz, DMSO-d$_6$) δ 8.17 (d, J=8.6 Hz, 1H), 8.0 (d, J=9.0 Hz, 1H), 7.86 (d, J=7.4 Hz, 2H), 7.81(d, J=7.4 Hz, 2H), 7.55 (m, 4H), 7.45 (m, 2H), 4.14 (s, 3H). MS(ES) m/z 445 [M–H].

EXAMPLE 5

Preparation of 2-(3-[2'-Methylphenyl]-2-hydroxyphenyl)-9-hydroxy-naphth[1,2-d]imidazole-5-sulfonic acid hydrochloride (Compound 49)

a) 2-hydroxy-3-(2'-methylphenyl)benzaldehyde:

The solution of 2-methoxy-3-(2'-methylphenyl)benzaldehyde (0.226 g, 1 mmol) in methylene chloride was cooled down to –78° C. and added boron tribromide (3 mL, 3 mmol). The solution was warmed up to room temperature and stirred for 18 hours. The reaction mixture was quenched with CH2Cl2/H2O (2:1), the layers were seperated and the organic layer was further washed with water and brine. The organics were combined, dried over MgSO$_4$ and concentrated to dryness to give the title compound. (0.047 g, 21%). MS(ES) m/z 213 [M+H].

Follow the procedure of example 5a), except substituting
2-methoxy-3-(4'-methylphenyl)benzaldehyde
2-methoxy-3-(3',4'-dimethylphenyl)benzaldehyde
2-methoxy-3-(3'-methoxyphenyl)benzaldehyde
2-methoxy-3-(3'-trifluoromethylphenyl)benzaldehyde
2-methoxy-3-(4'-fluorophenyl)benzaldehyde
2-methoxy-3-(4'-chlorophenyl)benzaldehyde
2-methoxy-3-(1'-dibenzofuranyl)benzaldehyde
2-methoxy-3-(1'-naphthalenyl)benzaldehyde
2-methoxy-3-(3'-chlorophenyl)benzaldehyde
2-methoxy-3-(3'-nitrophenyl)benzaldehyde
2-methoxy-3-phenylbenzaldehyde for 2-methoxy-3-(2'-methylphenyl)benzaldehyde the following compounds were generated:

2-hydroxy-3-(4'-methylphenyl)benzaldehyde, MS(ES) m/z 213 [M+H].

2-hydroxy-3-(3',4'-dimethylphenyl)benzaldehyde, MS(ES) m/z 227 [M+H].

2-hydroxy-3-(3'-trifluoromethylphenyl)benzaldehyde, MS(ES) m/z 267 [M+H].

2-hydroxy-3-(4'-fluorophenyl)benzaldehyde, MS(ES) m/z 217 [M+H].

2-hydroxy-3-(4'-chlorophenyl)benzaldehyde. Ref: Bull. Chem. Soc. Jpn., EN, 40, 1967,385–388

2-hydroxy-3-(1'-dibenzofuranyl)benzaldehyde. Ref: Bull. Chem. Soc. Jpn., EN, 40, 1967,385–388

2-hydroxy-3-(1'-naphthalenyl)benzaldehyde. Ref: Bull. Chem. Soc. Jpn., EN, 40, 1967,385–388

2-hydroxy-3-(3'-chlorophenyl)benzaldehyde, MS(ES) m/z 233 [M+H].

2-hydroxy-3-(3'-nitrophenyl)benzaldehyde, MS(ES) m/z 244 [M+H].

2-hydroxy-3-phenylbenzaldehyde. $^1$H NMR (300 MHz, CDCl$_3$) δ11.5 (s, 1H), 9.9 (s, 1H), 7.6 (m, 4H), 7.4 (m, 3H), 7.09(t, J=7.5 Hz, 1H).

b) 2-(3-[2'-Methylphenyl]-2-hydroxyphenyl)-9-hydroxy-naphth[1,2-d]imidazole-5-sulfonic acid hydrochloride:

To an agitated solution of 2-hydroxy-3-(2'-methylphenyl)benzaldehyde (0.030 g, 0.14 mmol) in EtOH (0.80 mL) was added 1,2-diamino-8-hydroxy-naphthalene-4-sulfonic acid dihydrochloride (0.033 g, 0.10 mmol) and sodium bisulfite (0.03 g) in water (0.20 mL). The solution was heated to 60° C. and agitated over 18 hours. The solution was cooled to room temperature, the tan precipitate was isolated by filtration and washed with water and ethyl acetate to provide the title compound (0.043 g, 89%) MS(ES) m/z 445 [M–H].

Following the same procedure of Example 5, except substituting:
2-hydroxy-3-(4'-methylphenyl)benzaldehyde
2-hydroxy-3-(3',4'-dimethylphenyl)benzaldehyde
2-hydroxy-3-(3'-trifluoromethylphenyl)benzaldehyde
2-hydroxy-3-(4'-fluorophenyl)benzaldehyde
2-hydroxy-3-(4'-chlorophenyl)benzaldehyde
2-hydroxy-3-(1'-dibenzofuranyl)benzaldehyde
2-hydroxy-3-(1'-naphthalenyl)benzaldehyde
2-hydroxy-3-(3'-chlorophenyl)benzaldehyde
2-hydroxy-3-(3'-nitrophenyl)benzaldehyde
2-hydroxy-3-phenylbenzaldehyde for 2-hydroxy-3-(2'-methylphenyl)benzaldehyde the following compounds were generated:

Compound 50: 2-(3-[4'-Methylphenyl]-2-hydroxyphenyl)-9-hydroxy-naphth[1,2-d]imidazole-5-sulfonic acid hydrochloride, (0.048 g, 99%) MS(ES) m/z 445 [M–H].

Compound 51: 2-(3-[3',4'-Dimethylphenyl]-2-hydroxyphenyl)-9-hydroxy-naphth[1,2-d]imidazole-5-sulfonic acid hydrochloride, (0.046 g, 93%) MS(ES) m/z 459 [M–H].

Compound 52: 2-(3-[3'-Trifluoromethylphenyl]-2-hydroxyphenyl)-9-hydroxy-naphth[1,2-d]imidazole-5-sulfonic acid hydrochloride, (0.054 g, 100%) MS(ES) m/z 499 [M–H].

Compound 53: 2-(3-[4'-Fluorophenyl]-2-hydroxyphenyl)-9-hydroxy-naphth[1,2-d]imidazole-5-sulfonic acid hydrochloride, (0.049 g, 100%) MS(ES) m/z 449 [M–H].

Compound 54: 2-(3-[4'-Chlorophenyl]-2-hydroxyphenyl)-9-hydroxy-naphth[1,2-d]imidazole-5-sulfonic acid hydrochloride, (0.050 g, 100%) MS(ES) m/z 465, 467 [M–H].

Compound 55: 2-(3-[1'-Dibenzofuranyl]-2-hydroxyphenyl)-9-hydroxy-naphth[1,2-d]imidazole-5-sulfonic acid hydrochloride, (0.056 g, 100%) MS(ES) m/z 521 [M–H].

Compound 56: 2-(3-[1'-Naphthalenyl]-2-hydroxyphenyl)-9-hydroxy-naphth[1,2-d]imidazole-5-sulfonic acid hydrochloride, (0.051 g, 100%) MS(ES) m/z 481 [M–H].

Compound 57: 2-(3-[3'-Chlorophenyl]-2-hydroxyphenyl)-9-hydroxy-naphth[1,2-d]imidazole-5-sulfonic acid hydrochloride, (0.050 g, 100%) MS(ES) m/z 465, 467 [M–H].

Compound 58: 2-(3-[3'-Nitrophenyl]-2-hydroxyphenyl)-9-hydroxy-naphth[1,2-d]imidazole-5-sulfonic acid hydrochloride, (0.051 g, 100%) MS(ES) m/z 476 [M–H].

Compound 59: 2-(3-phenyl-2-hydroxyphenyl)-9-hydroxy-naphth[1,2-d]imidazole-5-sulfonic acid hydrochloride, (0.032 g, 68%) MS(ES) m/z 431 [M–H].

EXAMPLE 6

Preparation of 2-(3-[2'-Methylphenyl]-2-hydroxyphenyl)-9-hydroxy-naphth[1,2-d]imidazole-7-sulfonic acid hydrochloride (Compound 60)

To an agitated solution of 2-hydroxy-3-(2'-methylphenyl)benzaldehyde (0.030 g, 0.14 mmol) in EtOH (0.80 mL) was added 1,2-diamino-8-hydroxy-naphthalene-6-sulfonic acid dihydrochloride (0.033 g, 0.10 mmol) and sodium bisulfite (0.03 g) in water (0.20 mL). The solution was heated to 60° C. and agitated over 18 hours. The solution was cooled to room temperature, the tan precipitate was isolated by filtration and washed with water and ethyl acetate to provide the title compound (0.048 g, 100%) MS(ES) m/z 445 [M–H]. Following the same procedure of Example 6, except substituting:

2-hydroxy-3-(4'-methylphenyl)benzaldehyde
2-hydroxy-3-(3',4'-dimethylphenyl)benzaldehyde
2-hydroxy-3-(3'-trifluoromethylphenyl)benzaldehyde
2-hydroxy-3-(4'-fluorophenyl)benzaldehyde
2-hydroxy-3-(4'-chlorophenyl)benzaldehyde
2-hydroxy-3-(1'-dibenzofuranyl)benzaldehyde
2-hydroxy-3-(1'-naphthalenyl)benzaldehyde
2-hydroxy-3-(3'-chlorophenyl)benzaldehyde
2-hydroxy-3-(3'-nitrophenyl)benzaldehyde
2-hydroxy-3-phenylbenzaldehyde for 2-hydroxy-3-(2'-methylphenyl)benzaldehyde the following compounds were generated:

Compound 61: 2-(3-[4'-Methylphenyl]-2-hydroxyphenyl)-9-hydroxy-naphth[1,2-d]imidazole-7-sulfonic acid hydrochloride, (0.044 g, 92%). $^1$NMR (400 MHz, DMSO-$d_6$) δ 7.78 (m, 4H), 7.53 (d, J=7.8 Hz, 2H), 7.38 (d, J=7.2 Hz, 1H), 7.33 (s, 1H), 7.26 (d, J=7.7 Hz, 2H), 7.15 (t, J=7.6 Hz, 1H), 2.5 (s, 3H). MS(ES) m/z 445 [M–H].

Compound 62: 2-(3-[3',4'-Dimethylphenyl]-2-hydroxyphenyl)-9-hydroxy-naphth[1,2-d]imidazole-5-sulfonic acid hydrochloride, (0.050 g, 100%). $^1$H NMR (400 MHz, DMSO-$d_6$) δ 7.75 (m, 3H), 7.42 (s, 1H), 7.34 (m, 4H), 7.21(d, J=7.8 Hz, 1H), 7.08 (t, J=7.6 Hz, 1H), 2.29 (s, 3H), 2.27 (s, 3H). MS(ES) m/z 459 [M–H].

Compound 63: 2-(3-[3'-Trifluoromethylphenyl]-2-hydroxyphenyl)-9-hydroxy-naphth[1,2-d]imidazole-7-sulfonic acid hydrochloride, (0.049 g, 91%) MS(ES) m/z 499 [M–H].

Compound 64: 2-(3-[4'-Fluorophenyl]-2-hydroxyphenyl)-9-hydroxy-naphth[1,2-d]imidazole-7-sulfonic acid hydrochloride, (0.043 g, 89%) MS(ES) m/z 449 [M–H].

Compound 65: 2-(3-[4'-Chlorophenyl]-2-hydroxyphenyl)-9-hydroxy-naphth[1,2-d]imidazole-7-sulfonic acid hydrochloride, (0.047 g, 93%). $^1$H NMR (400 MHz, DMSO-$d_6$) δ 8.27 (br s, 1H), 7.79 (s, 1H), 7.78 (d, J=7.1 Hz, 2H), 7.68(d, J=8.5 Hz, 2H), 7.5 (d, J=8.4 Hz, 2H), 7.43 (d, J=6.5 Hz, 1H), 7.35 (s, 1H), 7.12 (t, J=7.8 Hz, 1H). MS(ES) m/z 465, 467 [M–H].

Compound 66: 2-(3-[1'-Dibenzofuranyl]-2-hydroxyphenyl)-9-hydroxy-naphth[1,2-d]imidazole-7-sulfonic acid hydrochloride, (0.053 g, 95%) MS(ES) m/z 521 [M–H].

Compound 67: 2-(3-[1'-Naphthalenyl]-2-hydroxyphenyl)-9-hydroxy-naphth[1,2-d]imidazole-7-sulfonic acid hydrochloride, (0.049 g, 95%) MS(ES) m/z 481 [M–H].

Compound 68: 2-(3-[3'-Chlorophenyl]-2-hydroxyphenyl)-9-hydroxy-naphth[1,2-d]imidazole-7-sulfonic acid hydrochloride, (0.050 g, 100%) MS(ES) m/z 465, 467 [M–H].

Compound 69: 2-(3-[3'-Nitrophenyl]-2-hydroxyphenyl)-9-hydroxy-naphth[1,2-d]imidazole-7-sulfonic acid hydrochloride, (0.042 g, 82%). $^1$H NMR (400 MHz, DMSO-$d_6$) δ 8.54 (s, 1H), 8.23 (d, J=6.7 Hz, 1H), 8.12 (d, J=7.0 Hz, 1H), 7.76(m, 4H), 7.55 (d, J=7.5 Hz, 1H), 7.34 (s, 1H), 7.16 (t, J=7.7 Hz, 1H). MS(ES) m/z 476 [M–H].

Compound 70: 2-(3-phenyl-2-hydroxyphenyl)-9-hydroxy-naphth[1,2-d]imidazole-7-sulfonic acid hydrochloride, (0.013 g, 29%) MS(ES) m/z 431 [M–H].

EXAMPLE 7

Preparation of 2-(4-[2'-Methylphenyl]-2-hydroxyphenyl)-9-hydroxy-naphth[1,2-d]imidazole-5-sulfonic acid hydrochloride (Compound 71)

a) 2-hydroxy-4-(2'-methylphenyl)benzaldehyde:

The solution of 2-methoxy-4-(2'-methylphenyl) benzaldehyde (0.226 g, 1 mmol) in methylene chloride was cooled down to –78° C. and added boron tribromide (3 mL, 3 mmol). The solution was warmed up to room temperature and stirred for 18 hours. The reaction mixture was quenched with CH2Cl2/H2O (2:1), the layers were seperated and the organic layer was further washed with water and brine. The organics were combined, dried over $MgSO_4$ and concentrated to dryness to give the title compound.(0.047 g, 21%). MS(ES) m/z 213 [M+H].

Follow the procedure of example 5a), except substituting
2-methoxy-4-(4'-methylphenyl)benzaldehyde
2-methoxy-4-(3',4'-dimethylphenyl)benzaldehyde
2-methoxy-4-(3'-methoxyphenyl)benzaldehyde
2-methoxy-4-(3'-trifluoromethylphenyl)benzaldehyde
2-methoxy-4-(4'-fluorophenyl)benzaldehyde
2-methoxy-4-(4'-chlorophenyl)benzaldehyde
2-methoxy-4-(1'-dibenzofuranyl)benzaldehyde
2-methoxy-4-(1'-naphthalenyl)benzaldehyde
2-methoxy-4-(3'-chlorophenyl)benzaldehyde
2-methoxy-4-(3'-nitrophenyl)benzaldehyde
2-methoxy-4-phenylbenzaldehyde for 2-methoxy-3-(2'-methylphenyl)benzaldehyde the following compounds were generated:

2-hydroxy-4-(4'-methylphenyl)benzaldehyde, $^1$H NMR (300 MHz, CDCl$_3$) δ11.1 (s, 1H), 9.9 (s, 1H), 7.6 (d, J=7.2 Hz, 2H), 7.55 (s, 1H), 7.3 (d, J=7.5 Hz, 2H), 7.28 (d, J=7.5 Hz, 2H), 2.5 (s, 3H).

2-hydroxy-4-(3',4'-dimethylphenyl)benzaldehyde, $^1$H NMR (300 MHz, CDCl$_3$) δ11.1 (s, 1H), 9.9 (s, 1H), 7.6 (d, J=7.2 Hz, 1H), 7.45 (d, J=7.2 Hz, 1H), 7.4 (s, 1H), 7.22 (d, J=7.5 Hz, 2H), 7.20 (s, 1H), 2.33 (s, 3H), 2.30 (s, 3H).

2-hydroxy-4-(3'-trifluoromethylphenyl)benzaldehyde, $^1$H NMR (300 MHz, CDCl$_3$) δ11.1 (s, 1H), 9.9 (s, 1H), 7.6 (br m, 5H), 7.2 (m, 2H).

2-hydroxy-4-(4'-fluorophenyl)benzaldehyde, $^1$H NMR (300 MHz, CDCl$_3$) δ11.1 (s, 1H), 9.9 (s, 1H), 7.6 (m, 3H), 7.15 (m, 4H).

2-hydroxy-4-(4'-chlorophenyl)benzaldehyde. $^1$H NMR (300 MHz, CDCl$_3$) δ11.1 (s, 1H), 9.9 (s, 1H), 7.62 (d, J=7.5 Hz, 1H), 7.6 (d, J=7.2 Hz, 2H), 7.4 (d, J=7.2 Hz, 2H), 7.22 (d, J=7.5 Hz, 1H), 7.20 (s, 1H).

2-hydroxy-4-(1'-dibenzofuranyl)benzaldehyde. MS(ES) m/z 289 [M+H].

2-hydroxy-4-(1'-naphthalenyl)benzaldehyde. $^1$H NMR (300 MHz, CDCl$_3$) δ11.1 (s, 1H), 9.9 (s, 1H), 7.95 (m, 2H), 7.45 (m, 7H), 7.1 (s, 1H).

2-hydroxy-4-(3'-chlorophenyl)benzaldehyde, $^1$H NMR (300 MHz, CDCl$_3$) δ11.1 (s, 1H), 9.9 (s, 1H), 7.6 (d, J=7.2 Hz, 1H), 7.35 (t, J=7.5 Hz, 1H), 7.25 (d, J=7.5 Hz, 2H), 7.22 (s, 1H), 7.10 (s, 1H), 6.9 (d, J=7.2 Hz, 1H).

2-hydroxy-4-(3'-nitrophenyl)benzaldehyde, $^1$H NMR (300 MHz, CDCl$_3$) δ11.1 (s, 1H), 9.9 (s, 1H), 8.45 (s, 1H), 8.25 (d, J=7.2 Hz, 1H), 8.0 (d, J=7.2 Hz, 1H), 7.6 (m, 2H), 7.23 (m, 2H).

2-hydroxy-4-phenylbenzaldehyde. $^1$H NMR (300 MHz, CDCl$_3$) δ11.5 (s, 1H), 9.9 (s, 1H), 7.6 (m, 4H), 7.4 (m, 3H), 7.09(m, 1H).

b) 2-(4-[2'-Methylphenyl]-2-hydroxyphenyl)-9-hydroxy-naphth[1,2-d]imidazole-5-sulfonic acid hydrochloride:

To an agitated solution of 2-hydroxy-4-(2'-methylphenyl) benzaldehyde (0.030 g, 0.14 mmol) in EtOH (0.80 mL) was added 1,2-diamino-8-hydroxy-naphthalene-4-sulfonic acid dihydrochloride (0.033 g, 0.10 mmol) and sodium bisulfite (0.03 g) in water (0.20 mL). The solution was heated to 60° C. and agitated over 18 hours. The solution was cooled to room temperature, the tan precipitate was isolated by filtration and washed with water and ethyl acetate to provide the title compound (0.029 g, 60%) MS(ES) m/z 445 [M−H].
Following the same procedure of Example 7, except substituting:
2-hydroxy-4-(4'-methylphenyl)benzaldehyde
2-hydroxy-4-(3'-hydroxyphenyl)benzaldehyde
2-hydroxy-4-(4'-fluorophenyl)benzaldehyde
2-hydroxy-4-(4'-chlorophenyl)benzaldehyde
2-hydroxy-4-(1'-dibenzofuranyl)benzaldehyde
2-hydroxy-4-(1'-naphthalenyl)benzaldehyde
2-hydroxy-4-(3'-chlorophenyl)benzaldehyde
2-hydroxy-4-(3'-nitrophenyl)benzaldehyde
2-hydroxy-4-phenylbenzaldehyde
2-hydroxy-4-(3',4'-dimethylphenyl)benzaldehyde for 2-hydroxy-4-(2'-methylphenyl)benzaldehyde the following compounds were generated:
Compound 72: 2-(4-[4'-Methylphenyl]-2-hydroxyphenyl)-9-hydroxy-naphth[1,2-d]imidazole-5-sulfonic acid hydrochloride, (0.013 g, 26%) MS(ES) m/z 445 [M−H].
Compound 73: 2-(4-[3'-Hydroxyphenyl]-2-hydroxyphenyl)-9-hydroxy-naphth[1,2-d]imidazole-5-sulfonic acid hydrochloride, (0.048 g, 100%) MS(ES) m/z 447 [M−H].
Compound 74: 2-(4-[4'-Fluorophenyl]-2-hydroxyphenyl)-9-hydroxy-naphth[1,2-d]imidazole-5-sulfonic acid hydrochloride, (0.028 g, 57%) MS(ES) m/z 449 [M−H].
Compound 75: 2-(4-[4'-Chlorophenyl]-2-hydroxyphenyl)-9-hydroxy-naphth[1,2-d]imidazole-5-sulfonic acid hydrochloride, (0.026 g, 51%) MS(ES) m/z 465, 467 [M−H].
Compound 76: 2-(4-[1'-Dibenzofuranyl]-2-hydroxyphenyl)-9-hydroxy-naphth[1,2-d]imidazole-5-sulfonic acid hydrochloride, (0.051 g, 91%) MS(ES) m/z 521 [M−H].
Compound 77: 2-(4-[1'-Naphthalenyl]-2-hydroxyphenyl)-9-hydroxy-naphth[1,2-d]imidazole-5-sulfonic acid hydrochloride, (0.002 g, 3%) MS(ES) m/z 481 [M−H].
Compound 78: 2-(4-[3'-Chlorophenyl]-2-hydroxyphenyl)-9-hydroxy-naphth[1,2-d]imidazole-5-sulfonic acid hydrochloride, (0.040 g, 80%) MS(ES) m/z 465, 467 [M−H].
Compound 79: 2-(4-[3'-Nitrophenyl]-2-hydroxyphenyl)-9-hydroxy-naphth[1,2-d]imidazole-5-sulfonic acid hydrochloride, (0.043 g, 83%) MS(ES) m/z 476 [M−H].
Compound 80: 2-(4-phenyl-2-hydroxyphenyl)-9-hydroxy-naphth[1,2-d]imidazole-5-sulfonic acid hydrochloride, (0.047 g, 100%) MS(ES) m/z 431 [M−H].

EXAMPLE 8

Preparation of 2-(4-[2'-Methylphenyl]-2-hydroxyphenyl)-9-hydroxy-naphth[1,2-d]imidazole-7-sulfonic acid hydrochloride (Compound 81)

To an agitated solution of 2-hydroxy-4-(2'-methylphenyl) benzaldehyde (0.030 g, 0.14 mmol) in EtOH (0.80 mL) was added 1,2-diamino-8-hydroxy-naphthalene-6-sulfonic acid dihydrochloride (0.033 g, 0.10 mmol) and sodium bisulfite (0.03 g) in water (0.20 mL). The solution was heated to 60° C. and agitated overnight. The solution was cooled to room temperature, the tan precipitate was isolated by filtration and washed with water and ethyl acetate to provide the title compound (0.027 g, 55%) MS(ES) m/z 445 [M−H].
Following the same procedure of Example 8, except substituting:
2-hydroxy-4-(4'-methylphenyl)benzaldehyde
2-hydroxy-4-(3',4'-methylphenyl)benzaldehyde
2-hydroxy-4-(3'-hydroxyphenyl)benzaldehyde
2-hydroxy-4-(4'-fluorophenyl)benzaldehyde
2-hydroxy-4-(4'-chlorophenyl)benzaldehyde
2-hydroxy-4-(1'-dibenzofuranyl)benzaldehyde
2-hydroxy-4-(1'-naphthalenyl)benzaldehyde
2-hydroxy-4-(3'-chlorophenyl)benzaldehyde
2-hydroxy-4-(3'-nitrophenyl)benzaldehyde
2-hydroxy-4-phenylbenzaldehyde for 2-hydroxy-4-(2'-methylphenyl)benzaldehyde the following compounds were generated:

Compound 82: 2-(4-[4'-Methylphenyl]-2-hydroxyphenyl)-9-hydroxy-naphth[1,2-d]imidazole-7-sulfonic acid hydrochloride, (0.024 g, 49%). $^1$H NMR (400 MHz, DMSO-$d_6$)) δ 8.34 (d, J=8.0 Hz, 1H), 7.83 (m, 3H), 7.62 (d, J=7.9 Hz, 2H), 7.35(m, 5H), 2.35 (s, 3H). MS(ES) m/z 445 [M−H].
Compound 83: 2-(4-[3',4'-dimethylphenyl]-2-hydroxyphenyl)-9-hydroxy-naphth[1,2-d]imidazole-7-sulfonic acid hydrochloride, (0.052 g, 74%) MS(ES) m/z 460 [M+H].
Compound 84: 2-(4-[3'-Hydroxyphenyl]-2-hydroxyphenyl)-9-hydroxy-naphth[1,2-d]imidazole-7-sulfonic acid hydrochloride, (0.045 g, 93%) MS(ES) m/z 461 [M−H].
Compound 85: 2-(4-[4'-Fluorophenyl]-2-hydroxyphenyl)-9-bydroxy-naphth[1,2-d]imidazole-7-sulfonic acid hydrochloride, (0.031 g, 63%) MS(ES) m/z 449 [M−H].
Compound 86: 2-(4-[4'-Chlorophenyl]-2-hydroxyphenyl)-9-hydroxy-naphth[1,2-d]imidazole-7-sulfonic acid hydrochloride, (0.023 g, 46%) MS(ES) m/z 465, 467 [M-H].
Compound 87: 2-(4-[1'-Dibenzofuranyl]-2-hydroxyphenyl)-9-hydroxy-naphth[1,2-d]imidazole-7-sulfonic acid hydrochloride, (0.027 g, 48%) MS(ES) m/z 521 [M−H].
Compound 88: 2-(4-[1'-Naphthalenyl]-2-hydroxyphenyl)-9-hydroxy-naphth[1,2-d]imidazole-7-sulfonic acid hydrochloride, (0.007 g, 14%) MS(ES) m/z 481 [M−H].
Compound 89: 2-(4-[3'-Chlorophenyl]-2-hydroxyphenyl)-9-hydroxy-naphth[1,2-d]imidazole-7-sulfonic acid hydrochloride, (0.022 g, 43%) MS(ES) m/z 465, 467 [M-H].
Compound 90: 2-(4-[3'-Nitrophenyl]-2-hydroxyphenyl)-9-hydroxy-naphth[1,2-d]imidazole-7-sulfonic acid hydrochloride, (0.017 g, 33%) MS(ES) m/z 476 [M−H].
Compound 91: 2-(4-phenyl-2-hydroxyphenyl)-9-hydroxy-naphth[1,2-d]imidazole-7-sulfonic acid hydrochloride, (0.034 g, 73%). $^1$H NMR (400 MHz, DMSO-$d_6$)) δ 8.33 (d, J=8.2 Hz, 1H), 7.83 (m, 4H), 7.71 (d, J=7.5 Hz, 2H), 7.50 (m, 2H), 7.36(m, 3H). MS(ES) m/z 431 [M−H].

EXAMPLE 9

Preparation of 2-(3-phenyl-2-methoxyphenyl)-9-hydroxy-naphth[1,2-d]imidazole-7-carboxylic acid hydrochloride (Compound 92)

a) 2-[4-(1,3-dihydroisoindol-2-yl)-benzylidene]-succinic acid 1-ethyl ester:

To the refluxing solution of potassium tert-butoxide in tert-butanol was added 4-phthalimidobenzylaldehyde and diethyl succinate over 15 min. The reaction was allowed to reflux for 45 min., then cool to room temperature. The mixture was acidified with 3N HCl and concentrated under reduced pressure. The brown paste was treated with ice water and extracted multiple times with diethyl ether. The ether extracts were then extracted with cold sodium bicarbonate (sat.). The aqueous solution was slowly acidified with conc. HCl and the title (3.0 g, 79%) product was collected by filtration. MS(ES) m/z 397 [M+H+H2O].

b) 4-acetoxy-6-aminonaphthalene-2-carboxylic acid ethyl ester:

To a suspension of the compound of 9a) (3.0 g, 7.9 mmol) in acetic anhydride (25 mL) at room temperature was added sodium acetate (1.5 g, 20 mmol). The mixture was heated at reflux for 4 hours and cooled down to room temperature. The product was precipitated from acetic acid, collected and washed with methanol.

The above crude product (2.0 g, 5.0 mmol) was taken up a 1:1 mixture of chloroform and ethanol (20 mL). At room remperature, an excess of hydrazine was added and the reaction was allowed to stir for 6 h. The mixture was diluted in chloroform, washed with water and brine and concentrated to give the desired product as a red oil (69%). $^1$H NMR (300 Hz, CDCl3) δ 8.05 (s, 1H), 7.7 (d, J=9.0 Hz, 1H), 7.4 (s, 1H), 7.35(s, 1H), 7.0 (dd, J=9.0 Hz, 1.8 Hz, 1H), 4.4 (m, 2H), 1.9 (s, 3H), 1.5 (s, 3H). MS(ES) m/z 273 [M+H].

c) 7-amino-1-hydroxy-3-naphthoic acid:

The compound of example 9b) was taken up in 6N HCl (70 mL) and heated at reflux for 2 hours. After cooling down to room temperature, the solid was collected and washed with ethyl acetate. The title compound was obtained as pale solid (4.5 g, 64%). $^1$H NMR (300 Hz, CDCl3) δ 10.7 (br s, 1H), 8.08 (s, 2H), 7.95 (s, 1H), 7.45 (d, J=9.0 Hz, 2H). MS(ES) m/z 204 [M+H].

d) 7,8-Diamino-1-hydroxy-3-naphthoic acid dihydrochloride:

A stirred solution of p-benzenediazonium sulfonamide, was prepared by the addition of sulfanilamide (0.07 g, 0.4 mmole) in 10% aqueous HCl (2.5 mL) to sodium nitrite (0.07 g, 0.5 mmole) in water (0.5 mL) at 0° C. After 15 min. of standing at 0° C., 7-amino-1-hydroxy-3-naphthoic acid (0.07 g, 0.325 mmole) was added in water (1.0 mL) and the reaction was stirred at room temperature for 30 min. The reaction mixture was added to SnCl$_2$ in concentrated HCl (2 mL) and heated at 95° C. over 18 hours. The reaction was filtered to give the title compound (0.04 g; 43%) as a white solid. MS(ES) m/z 219 [M+H].

e) 1-(3,4-dimethylphenyl)-3-methyl-5-hydroxy-4-pyrrazolecarboxaldehyde:

A suspension of 2-(3,4-dimethylphenyl)-5-methyl-2,4-dihydropyrazol-3-one (8.7 g, 43 mmol) in DMF was treated with phosphorous oxychloride (4.82 mL, 52 mmol) at 0° C. After heated up to 90° C. for 2 hours, the mixture was poured to ice-water and stirred for 18 hours, the resulting solid was filtered to give the title compound as a grey solid (7.83 g, 79%). MS(ES) m/z 231 [M+H].

f) 2-(3-phenyl-2-methoxyphenyl)-9-hydroxy-naphth[1,2-d] imidazole-7-carboxylic acid hydrochloride To an agitated solution of 2-methoxy-3-phenylbenzaldehyde (0.020 g, 0.08 mmol) in EtOH (0.80 mL) was added 7,8-Diamino-1-hydroxy-3-naphthoic acid dihydrochloride (0.02 g, 0.07 mmol) and sodium bisulfite (0.02 g) in water (0.20 mL). The solution was heated to 60° C. and agitated over 18 hours. The solution was cooled to room temperature and concentrated under reduced pressure. The tan residue was subjected to HPLC (ODS-A, gradient 10–90% CH3CN/water 0.1% TFA) to provide the title compound (0.008 g, 20%) MS(ES) m/z 411 [M+H].

Following the same procedure of Example 9, except substituting:

2-methoxy-3-(3',4'-dimethylphenyl)benzaldehyde
2-hydroxy-3-(3',4'-dimethylphenyl)benzaldehyde
1-(3,4-dimethylphenyl)-3-methyl-5-hydroxy-4-pyrrazolecarboxaldehyde
1-hydroxy-2-naphthaldehyde
2-hydroxy-2-naphthaldehyde
2-pyridinecarboxaldehyde for 2-methoxy-3-phenylbenzaldehyde the following compounds were generated:

Compound 93: 2-(3-[3',4'-dimethylphenyl]-2-methoxyphenyl)-9-hydroxy-naphth[1,2-d]imidazole-7-carboxylic acid trifluoroacetate, (0.004 g, 8%) MS(ES) m/z 439 [M+H].

Compound 94: 2-(3-[3',4'-dimethylphenyl]-2-hydroxyphenyl)-9-hydroxy-naphth[1,2-d]imidazole-7-carboxylic acid trifluoroacetate, (0.005 g, 11%) MS(ES) m/z 425 [M+H].

Compound 95: 2-(1-[3,4-dimethylphenyl]-3-methyl-5-hydroxy-1H-pyrrazole-4-yl)-9-hydroxy-3H-naphth[1,2-d]imidazole-7-carboxylic acid trifluoroacetate, (0.004 g, 13%) MS(ES) m/z 429 [M+H].

Compound 96: 2-(1-hydroxy-2-naphthalenyl)-9-hydroxy-naphth[1,2-d]imidazole-7-carboxylic acid trifluoroacetate, (0.003 g, 7%) MS(ES) m/z 306 [M+H].

Compound 97: 2-(2-hydroxy-1-naphthalenyl)-9-hydroxy-naphth[1,2-d]imidazole-7-carboxylic acid trifluoroacetate, (0.02 g, 10%). $^1$H NMR (400 MHz, DMSO-d$_6$) δ 8.15 (d, J=9.1 Hz, 1H), 8.09 (d, J=9.1 Hz, 1H), 7.98 (d, J=8.2 Hz, 1H), 7.93 (s, 1H), 7.91 (s, 1H)), 7.52 (m, 2H), 7.46 (m, 3H). MS(ES) m/z 306 [M+H].

Compound 98: 2-(2-pyridinyl)-9-hydroxy-naphth[1,2-d] imidazole-7-carboxylic acid trifluoroacetate, (0.005 g, 16%) MS(ES) m/z 306 [M+H].

EXAMPLE 10

Preparation of 2-(3',4'-dimethylbiphenyl-3-yl)-9-hydroxy-3H-naphtho[1,2-d]imidazole-7-sulfonic acid hydrochloride (Compound 99)

a) 3',4'-dimethylbiphenyl-4-carbaldehyde:

A solution of 4-bromo-1,2-dimethylbenzene (0.225 g, 1.67 mmol), 4-formylphenylboronic acid (0.25 g, 1.67 mmol), 2M aqu. sodium carbonate (1.67 mL, 3.34 mmol) and tetrakistriphenylphosphinopalladium(0) (0.025 g) in 1,4-dioxane (30 mL) was stirred and heated under reflux under a nitrogen atmosphere for 24 h.

The reaction mixture was cooled and suspended between ethyl acetate and 3M aqu. hydrochloric acid (30 mL). The phases were separated and the aqueous phase was further extracted with ethyl acetate (3 times). The combined organic layers were dried over anhydrous MgSO$_4$ and concentrated under reduced pressure to give the title product. (0.26 g, 74%). MS(ES) m/z 211 [M+H].

Follow the procedure of example 10a), except substituting, 3-formylphenylboronic acid for 4-formylphenylboronic acid and
4-tert-butylphenylbromide
3,4-dimethylphenylbromide for 4-bromo-1,2-dimethylbenzene, the follow compounds were generated:

4-tert-butylbiphenyl-3-carbaldehyde, MS(ES) m/z 239 [M+H].

3',4'-dimethylbiphenyl-3-carbaldehyde, MS(ES) m/z 211 [M+H].

b) 3-(4-tert-butylbenzyloxy)-benzaldehyde:

3-hydroxybenzaldehyde (0.5 g, 4.1 mmol) in DMF (5 mL) was treated with potassium carbonate (0.56 g, 4.1 mmol) and 4-tert-butylbenzylbromide (0.9 g, 4.1 mmol). The solution was heated up to 90° C. for 36 hours. After cooling down to room temperature, the reaction mixture was poured into water and extracted with diethyl ether twice. The organic layers were combined, dried over MgSO$_4$, and concentrated to dryness. The crude product was passed through a plug of SiO2 with 5% ethyl acetate in hexane (250 mL). The title compound was obtained as a solid (0.7 g, 64%). MS(ES) m/z 269 [M+H].

Follow the procedure of example 10b), except substituting 3-trifluoromethylbenzylbromide for 4-tert-butylbenzylbromide, the following compound was obtained:
3-(3-trifluoromethylbenzyloxy)benzaldehyde, MS(ES) m/z 281 [M+H].

c) 3-(3,4-dimethylbenzyloxy)benzaldehyde:

Polymer-bounded triphenylphosphine (2.1 g, 6 mmol), DEAD (0.97 mL, 6 mmol), 3,4-dimethylphenylmethanol (0.8 g, 6 mmol), 3-hydroxybenzaldehyde (0.5 g, 4 mmol) in methylene chloride were stirred at room temperature for 48 hours. The resin was filtered and the filtrate was concentrated down to an oil. The crude oil was passed through a plug of SiO2 with 5% ethyl acetate in hexane (250 mL). The title compound was obtained as a solid (0.24 g, 25%). MS(ES) m/z 241 [M+H].

d) 2-(3',4'-dimethylbiphenyl-3-yl)-9-hydroxy-3H-naphtho[1,2-d]imidazole-7-sulfonic acid hydrochloride:

To an agitated solution of 3',4'-dimethylbiphenyl-3-carbaldehyde (0.030 g, 0.14 mmol) in EtOH (0.80 mL) was added 1,2-diamino-8-hydroxy-naphthalene-6-sulfonic acid dihydrochloride (0.033 g, 0.10 mmol) and sodium bisulfite (0.03 g) in water (0.20 mL). The solution was heated to 60° C. and agitated for 18 hours. The solution was cooled to room temperature, the tan precipitate was isolated by filtration and washed with water and ethyl acetate to provide the title compound (0.035 g, 85%) MS(ES) m/z 443 [M−H]. Following the same procedure of Example 10, except substituting:
biphenyl-4-carbaldehyde
3',4'-dimethylbiphenyl-4-carbaldehyde
4'-tert-butylbiphenyl-3-carbaldehyde
3-(4-tert-butylbenzyloxy)-benzaldehyde
3-(3-trifluoromethylbenzyloxy)benzaldehyde
3-(3,4-dimethylbenzyloxy)-benzaldehyde for 3',4'-dimethylbiphenyl-3-carbaldehyde, the following compounds were generated:

Compound 100: 2-biphenyl-4-yl-9-hydroxy-3H-naphtho[1,2-d]imidazole-7-sulfonic acid hydrochloride, (0.024 g, 62%) MS(ES) m/z 415 [M−H].

Compound 101: 2-(3',4'-dimethylbiphenyl-4-yl)-9-hydroxy-3H-naphtho[1,2-d]imidazole-7-sulfonic acid trifluoroacetate, (0.003 g, 7%) MS(ES) m/z 445 [M+H].

Compound 102: 2-(4'-tert-butylbiphenyl-3-yl)-9-hydroxy-3H-naphtho[1,2-d]imidizole-7-sulfonic acid trifluoroacetate, (0.001 g, 3%) MS(ES) m/z 473 [M+H].

Compound 103: 2-[3-(4-tert-butylbenzyloxy)-phenyl]-9-hydroxy-3H-naphtho[1,2-d]imidizole-7-sulfonic acid hydrochloride, (0.020 g, 44%) MS(ES) m/z 501 [M−H].

Compound 104: 2-[3-(3-trifluoromethylbenzyloxy)-phenyl]-9-hydroxy-3H-naphtho[1,2-d]imidizole-7-sulfonic acid hydrochloride, (0.024 g, 51%) MS(ES) m/z 513 [M−H].

Compound 105: 2-[3-(3,4-dimethylbenzyloxy)-phenyl]-9-hydroxy-3H-naphtho[1,2-d]imidizole-7-sulfonic acid hydrochloride, (0.018 g, 41%) MS(ES) m/z 473 [M−H].

EXAMPLE 11

Preparation of 2-(3',4'-dimethylbiphenyl-3-yl)-9-hydroxy-3H-naphtho[1,2-d]imidazole-7-carboxylic acid hydrochloride (Compound 106)

To an agitated solution of 3,4-dimethylbiphenyl-3-carbaldehyde (0.019 g, 0.09 mmol) in EtOH (0.80 mL) was added 7,8-Diamino-1-hydroxy-3-naphthoic acid dihydrochloride (0.024 g, 0.08 mmol) and sodium bisulfite (0.02 g) in water (0.20 mL). The solution was heated to 60° C. and agitated overnight. The solution was cooled to room temperature and concentrated under reduced pressure. The tan residue was subjected to HPLC (ODS-A, gradient 10–90% CH$_3$CN/water 0.1% TFA) to provide the title compound (0.015 g, 33%) MS(ES) m/z 409 [M+H].

Following the same procedure of Example 11, except substituting:
3',4'-dimethylbiphenyl-4-carbaldehyde
4'-tert-butylbiphenyl-3-carbaldehyde,
3-phenoxybenzaldehyde for 3,4-dimethylbiphenyl-3-carbaldehyde, the following compounds were generated:

Compound 107: 2-(3',4'-dimethylbiphenyl-4-yl)-9-hydroxy-3H-naphtho[1,2-d]imidazole-7-carboxylic acid trifluoroacetate, (0.012 g, 28%) MS(ES) m/z 409 [M+H].

Compound 108: 2-(4'-tert-butylbiphenyl-3-yl)-9-hydroxy-3H-naphtho[1,2-d]imidazole-7-carboxylic acid trifluoroacetate, (0.015 g, 33%) MS(ES) m/z 435 [M−H].

Compound 109: 9-hydroxy-2-(3-phenoxyphenyl)-3H-naphtho[1,2-d]imidazole-7-carboxylic acid trifluoroacetate, (0.004 g, 12%) MS(ES) m/z 397 [M+H].

EXAMPLE 12

Preparation of 3-[2-(3',4'-dimethylbiphenyl-3-yl)-9-hydroxy-3H-naphtho[1,2-d]imidazole-7-sulfonylamino]-benzoic acid: (Compound 110)

2-(3',4'-dimethylbiphenyl-3-yl)-9-hydroxyl-3H-naphtho[1,2-d]imidazole-7-sulfonic acid hydrochloride(0.08 g, 0.18 mmol) was suspended in 1 ml thionyl chloride containing catalytic amount of N,N-dimethylformamide. The reaction mixture was heated to 60° C. for 3 hours then was concentrated to dryness to give 2-(3',4'-dimethylbiphenyl-3-yl)-9-hydroxyl-3H-naphtho[1,2-d]imidazole-7-sulfonyl chloride.

To an agitated suspension of 3-aminobenzoic acid (0.028 g, 0.2 mmol) in THF (1 mL) was added 2-(3',4'-dimethylbiphenyl-3-yl)-9-hydroxyl-3H-naphtho[1,2-d]imidazole-7-sulfonyl chloride (0.083 g, 0.18 mmol) and sodium hydroxy (0.018 g, 0.4 mmol) in water (0.5 mL). After agitated for 30 minutes, the reaction mixture was added 6N hydrochloride (2 ml) and concentrated under reduced pressure. The residue was subjected to HPLC (ODS-A, gradient 10–90% CH3CN/water 0.1% TFA) to provide the title compound (0.005 g, 4%) MS(ES) m/z 564 [M+H].

Following the same procedure of Example 12, except substituting:
piperidine-3-carboxylic acid for 3-aminobenzoic acid, the following compound was generated:

Compound 111: 1-[2-(3',4'-dimethylbiphenyl-3-yl)-9-hydroxy-3H-naphtho[1,2-d]imidazole-7-sulfonyl]-piperidine-3-carboxylic acid, (0.015 g, 8%) MS(ES) m/z 556 [M+H].

EXAMPLE 13

Preparation of (S)-1-[2-(3',4'-dimethyl-biphenyl-3-yl)-9-hydroxy-3H-naphtho[1,2-d]imidazole-7-sulfonyl]-pyrrolidine-2-carboxylic acid: (Compound 112)

To an agitated suspension of (S)-pyrrolidine-2-carboxylic acid tert-butyl ester (0.036 g, 0.21 mmol) in DMF (1 mL) was added 2-(3',4'-dimethylbiphenyl-3-yl)-9-hydroxyl-3H-naphtho[1,2-d]imidazole-7-sulfonyl chloride (0.064 g, 0.14 mmol) and triethyl amine (0.022 g, 0.21 mmol). After agitated for 15 hrs, the reaction mixture was concentrated under reduced pressure to give (S)-1-[2-(3',4'-dimethylbiphenyl-3-yl)-9-hydroxy-3H-naphtho[1,2-d]imidazole-7-sulfonyl]-pyrrolidine-2-carboxylic acid tert-butyl ester. The crude product was treated with 90% trifluoroacetate acid (2 ml). After agitated for 1 hour, the mixture was concentrated under reduced pressure, then subjected to to HPLC (ODS-A, gradient 10–90% CH3CN/ water 0.1% TFA) to provide the title compound (0.006 g, 8%) MS(ES) m/z 542 [M+H].

EXAMPLE 14
Preparation of ({1-2-(3',4'-dimethylbiphenyl-3-yl)-9-hydroxy-3H-naphtho[1,2-d]imidazol-7-yl]-methanoyl}-amino)-acetic acid: (Compound 113)

To an agitated solution of 2-(3',4'-dimethylbiphenyl-3-yl)-9-hydroxy-3H-naphtho[1,2-d]imidazole-7-carboxylic acid (0.1 g, 0.25 mmol) in DMF (1 mL) was added glycine tert butyl ester (0.046 g, 0.27 mmol), triethyl amine (0.058 g, 0.75 mmol), 1-hydroxybenzotriazole (0.035 g, 0.26 mmol), and 1-ethyl-3-(3 dimethylaminopropyl)carbodiimide hydrochloride (0.05 g, 0.26 mmol). After agitated for 15 hrs, the reaction mixture was concentrated under reduced pressure to dryness. The residue was treated with 90% trifluoroacetate acid (1 mL). After agitated for 1 hour, the mixture was concentrated under reduced pressure, then subjected to HPLC (ODS-A, gradient 10–90% CH3CN/water 0.1% TFA) to provide the title compound (0.020 g, 18%) MS(ES) m/z 466 [M+H].

Following the same procedure of Example 13, except substituting:
L-alanine tert-butyl ester
sarcosine tert-butyl ester
L-proline tert-butyl ester for glycine tert butyl ester, the following compounds were generated:
Compound 114: (S)-2-({1-[2-(3',4'-dimethylbiphenyl-3-yl)-9-hydroxyl-3H-naphtho[1,2-d]imidazol-7-yl]-methanoyl}-amino)-propionic acid (0.025 g, 21%) MS(ES) m/z 480 [M+H].
Compound 115: ({1-[2-(3',4'-dimethylbiphenyl-3-yl)-9-hydroxyl-3H-naphtho[1,2-d]imidazol-7-yl]-methanoyl}-methylamino)-acetic acid (0.015 g, 13%) MS(ES) m/z 480 [M+H].
Compound 116: (S)-1-{1-[2-(3',4'-dimethylbiphenyl-3-yl)-9-hydroxyl-3H-naphtho[1,2-d]imidazol-7-yl]-methanoyl}-pyrrolidine-2-carboxylic acid (0.016 g, 22%) MS(ES) m/z 506 [M+H].

EXAMPLE 15
Preparation of (S)-2-({1-[2-(3',4'-dimethylbiphenyl-3-yl)-9-hydroxy-3H-naphtho[1,2-d]imidazol-7-yl]-methanoyl}-amino)-3-phenylpropionic acid: (Compound 117)

To the 2-(3',4'-dimethylbiphenyl-3-yl)-9-hydroxy-3H-naphtho[1,2-d]imidazole-7-carboxylic acid (0.05 g, 0.1 mmol) in DMF (0.5 mL) at room temperature was added phenylalanine tert butyl ester hydrochloride (0.11 mmol). A cocktail solution of 1-ethyl-3-(3-dimethylaminopropyl) carbodiimide hydrochloride (0.021 g, 0.11 mmol), triethylamine (0.3 mmol) in DMF (0.5 mL) was added and the reaction was agitated at room temperature for 18 hours. 1 ml water was added to the reaction mixture resulting in the formation of a tan precipitate. the mixture was filtered and allowed to dry. The solid mass was transferred into vial and dissolved in 90% trifluoroacetic acid (1 mL). The solutions were agitated for 6 hrs then concentrated under reduced pressure. The residues were taked up in DMSO and subjected to Gilson HPLC purification. The title compound was abtained as solid.(0.006 g, 10%). MS(ES) m/z 556 [M+H].

Following the procedure of example 15, except substituting
H-Tyr-OtBu HCl
H-Ile-OtBu HCl
H-Leu-OtBu HCl
H-Asp(OtBu)-OtBu HCl
H-Val-OtBu HCl
H-Trp-OtBu HCl
H-PhG-OtBu HCl for phenylalanine tert butyl ester hydrochloride, the following compounds were prepared:
Compound 118: (S)-2-({1-[2-(3',4'-dimethylbiphenyl-3-yl)-9-hydroxy-3H-naphtho[1,2-d]imidazol-7-yl]-methanoyl}-amino)-3-(4-hydroxyphenyl)-propionic acid. MS(ES) m/z 572 [M+H].
Compound 119: (S)-2-({1-[2-(3',4'-dimethylbiphenyl-3-yl)-9-hydroxy-3H-naphtho[1,2-d]imidazol-7-yl]-methanoyl}-amino)-3-methylpentanoic acid. MS(ES) m/z 522 [M+H].
Compound 120: (S)-2-({1-[2-(3',4'-dimethylbiphenyl-3-yl)-9-hydroxy-3H-naphtho[1,2-d]imidazol-7-yl]-methanoyl}-amino)-4-methylpentanoic acid. MS(ES) m/z 522 [M+H].
Compound 121: (S)-2-({1-[2-(3',4'-dimethylbiphenyl-3-yl)-9-hydroxy-3H-naphtho[1,2-d]imidazol-7-yl]-methanoyl}-amino)-succinic acid. MS(ES) m/z 524 [M+H].
Compound 122: (S)-2-({1-[2-(3',4'-dimethylbiphenyl-3-yl)-9-hydroxy-3H-naphtho[1,2-d]imidazol-7-yl]-methanoyl}-amino)-3-methylbutyric acid. MS(ES) m/z 508 [M+H].
Compound 123: (S)-2-({1-[2-(3',4'-dimethylbiphenyl-3-yl)-9-hydroxy-3H-naphtho[1,2-d]imidazol-7-yl]-methanoyl}-amino)-3-(1H-indol-3-yl)-propionic acid. MS(ES) m/z 595 [M+H].
Compound 124: (S)-2-({1-[2-(3',4'-dimethylbiphenyl-3-yl)-9-hydroxy-3H-naphtho[1,2-d]imidazol-7-yl]-methanoyl}-amino)-2-phenylacetic acid. MS(ES) m/z 542 [M+H].

EXAMPLE 16
Preparation of (S)-2-({1-[2-(4'-tert-butylbiphenyl-3-yl)-9-hydroxy-3H-naphtho[1,2-d]imidazol-7-yl]-methanoyl}-amino)-3-phenylpropionic acid (Compound 125)

To the 2-(4'-tert-butylbiphenyl-3-yl)-9-hydroxy-3H-naphtho[1,2-d]imidazole-7-carboxylic acid (0.047 g, 0.1 mmol) in dimethylformamide (0.5 mL)at room temperature was added phenylalanine tert butyl ester hydrochloride (0.11 mmol). A cocktail solution of 1-ethyl-3-(3-dimethylaminopropyl)carbodiimide hydrochloride (0.021 g, 0.11 mmol), triethylamine (0.3 mmol) in DMF (0.5 mL) was added and the reaction was agitated at room temperature for 18 hours. 1 ml water was added to the reaction mixture resulting in the formation of a tan precipitate. the mixture was filtered and allowed to dry. The solid mass was transferred into vial and dissolved in 1 ml of 90% trifluoroacetic acid. The solutions were agitated for 6 hrs then concentrated under reduced pressure. The residues were taked up in DMSO and subjected to Gilson HPLC purification. The title compound was abtained as solid.(0.016 g, 28%). MS(ES) m/z 584 [M+H].

Following the procedure of example 16, except substituting
H-Tyr-OtBu HCl
H-Ile-OtBu HCl
H-Leu-OtBu HCl
H-Asp(OtBu)-OtBu HCl
H-Val-OtBu HCl
H-Trp-OtBu HCl
H-PhG-OtBu HCl
H-Glu(OTBU)-OTBU
3-Aminopropionic acid tert-butyl ester for phenylalanine tert butyl ester hydrochloride, the following compounds were prepared:
Compound 126: (S)-2-({1-[2-(4'-tert-butylbiphenyl-3-yl)-9-hydroxy-3H-naphtho[1,2-d]imidazol-7-yl]-methanoyl}-amino)-3-(4-hydroxyphenyl)-propionic acid. MS(ES) m/z 600 [M+H].

Compound 127: (S)-2-({1-[2-(4'-tert-butylbiphenyl-3-yl)-9-hydroxy-3H-naphtho[1,2-d]imidazol-7-yl]-methanoyl}-amino)-3-methylpentanoic acid. MS(ES) m/z 550 [M+H].

Compound 128: (S)-2-({1-[2-(4'-tert-butylbiphenyl-3-yl)-9-hydroxy-3H-naphtho[1,2-d]imidazol-7-yl]-methanoyl}-amino)-4-methylpentanoic acid. MS(ES) m/z 550 [M+H].

Compound 129: (S)-2-({1-[2-(4'-tert-butylbiphenyl-3-yl)-9-hydroxy-3H-naphtho[1,2-d]imidazol-7-yl]-methanoyl}-amino)-succinic acid. MS(ES) m/z 552 [M+H].

Compound 130: (S)-2-({1-[2-(4'-tert-butylbiphenyl-3-yl)-9-hydroxy-3H-naphtho[1,2-d]imidazol-7-yl]-methanoyl}-amino)-3-methylbutyric acid. MS(ES) m/z 536 [M+H].

Compound 131: (S)-2-({1-[2-(4'-tert-butylbiphenyl-3-yl)-9-hydroxy-3H-naphtho[1,2-d]imidazol-7-yl]-methanoyl}-amino)-3-(1H-indol-3-yl)-propionic acid. MS(ES) m/z 623 [M+H].

Compound 132: (S)-2-({-[2-(4'-tert-butylbiphenyl-3-yl)-9-hydroxy-3H-naphtho[1,2-d]imidazol-7-yl]-methanoyl}-amino)-2-phenylacetic acid. MS(ES) m/z 570 [M+H].

Compound 133: (S)-2-({1-[2-(4'-tert-butylbiphenyl-3-yl)-9-hydroxy-3H-naphtho[1,2-d]imidazol-7-yl]-methanoyl}-amino)-pentanedioic acid. MS(ES) m/z 566 [M+H].

Compound 134: 3-({1-[2-(4'-tert-butylbiphenyl-3-yl)-9-hydroxy-3H-naphtho[1,2-d]imidazol-7-yl]-methanoyl}-amino)-propionic acid. MS(ES) m/z 508 [M+H].

EXAMPLE 17

Preparation of (S)-2-({1-[2-(3,4-dimethylbiphenyl-3-yl)-9-hydroxy-3H-naphtho[1,2-d]imidazol-7-yl]-methanoyl}-amino)-pentanedioic acid (Compound 135)

Follow the procedure of example 16, except substituting 2-(4'-tert-butylbiphenyl-3-yl)-9-hydroxy-3H-naphtho[1,2-d]imidazole-7-carboxylic acid for 2-(3',4'-dimethylbiphenyl-3-yl)-9-hydroxy-3H-naphtho[1,2-d]imidazole-7-carboxylic acid and substituting H-Glu (OTBU)-OTBU for phenylalanine tert butyl ester hydrochloride, the title compound was preparation as solid (0.019 g, 35%) MS(ES) m/z 538 [M+H].

EXAMPLE 18

2-[6-(4-tert-butylphenyl)-pyridin-2-yl]-9-hydroxy-3H-naphtho[1,2-d]imidazole-7-carboxylic acid (Compound 136)

a) [6-(4-tert-butylphenyl)-pyridin-2-yl]-methanol:

A solution of 6-bromopyridine-2-carboxylic acid (1.0 g, 5.0 mmol), 4-tert-butylphenylboronic acid (0.89 g, 5.0 mmol), 2M aqu. sodium carbonate (5.0 mL, 10.0 mmol) and tetrakistriphenylphosphinopalladium(0) (0.075 g) in 1,4-dioxane (30 mL) was stirred and heated under reflux under a nitrogen atmosphere for 24 h.

The reaction mixture was cooled and suspended between ethyl acetate and 3M aqu. hydrochloric acid (30 mL). The phases were separated and the aqueous phase was further extracted with ethyl acetate (3 times). The combined organic layers were dried over anhydrous $MgSO_4$ and concentrated under reduced pressure to give crude product.

To the above crude product (1.3 g, 5 mmol) in THF (20 mL) was slowly added borane-tetrahydrofuran (20 mL, 20.0 mmol) at 0° C. and continuously stirred for half hour at 0° C., then 18 hours at room temperature. The reaction mixture was neutralized with methanol and concentrated at reduced pressure. The residue was taken up with ethyl acetate (50 mL)and washed with water (3 times). The combined organics were dried over ($MgSO_4$), filtered and concentrated to dryness. The crude solid was further purified through column chromagratophy on $SiO_2$ (ethyl acetate/hexane=1:4) to give the title compound. (0.65 g, 50%). MS(ES) m/z 242 [M+H].

b) 2-[6-(4-tert-butylphenyl)-pyridin-2-yl]-9-hydroxy-3H-naphtho[1,2-d]imidazole-7-carboxylic acid:

A solution of dimethyl sulfoxide (0.47 mL, 6.2 mmol) in methylene chloride was added to a solution of oxalyl chloride (0.2 mL, 3.1 mmol) in 20 ml methylene chloride at –78° C. After stirred for 5 min., [6-(4-tert-butylphenyl)-pyridin-2-yl]-methanol (0.5 g, 2 mmol) was added. The reaction mixture was stirred at –78° C. for 15 min., triethylamine (1.76 mL, 12.45 mmol) was then added. While warming up to room temperature, it was continuously stirred for 1 hour. The reaction mixture was washed with water (3 times), the combined organics were dried over $MgSO_4$, filtered and concentrated down under reduced pressure to give the crude product.

To an agitated solution of the above product (0.054 g, 0.2 mmol) in EtOH (2 mL) was added 7,8-diamino-1-hydroxy-3-naphthoic acid dihydrochloride dihydrochloride (0.058 g, 0.20 mmol) and sodium bisulfite (0.04 g) in water (0.40 mL). The solution was heated to 60° C. and agitated overnight. The solution was cooled to room temperature and concentrated under reduced pressure. The residures were taked up in DMSO and subjected to Gilson HPLC purification. The title compound was abtained as solid.(0.004 g, 4%). MS(ES) m/z 438 [M+H].

EXAMPLE 19

2-[5-(3,4-dimethylphenyl)-furan-2-yl]-9-hydroxy-3H-naphtho[1,2-d]imidazole-7-carboxylic acid (Compound 137)

a) 5-(3,4-dimethylphenyl)-furan-2-carbaldehyde:

A solution of 5-bromofuran-2-carbaldehyde (0.23 g, 1.33 mmol), 3,4-dimethylphenylboronic acid (0.2 g, 1.33 mmol), 2M aqu. sodium carbonate (1.33 mL, 2.66 mmol) and tetrakistriphenylphosphinopalladium(0) (0.025 g) in 1,4-dioxane (30 mL) was stirred and heated under reflux under a nitrogen atmosphere for 24 h.

The reaction mixture was cooled and suspended between ethyl acetate and 3M aqu. hydrochloric acid (30 ml). The phases were separated and the aqueous phase was further extracted with ethyl acetate (3 times). The combined organic layers were dried over anhydrous $MgSO_4$ and concentrated under reduced pressure to give the title product. $^1$H NMR (300 MHz, DMSO-$d_6$) δ 9.6 (s, 1H), 7.68 (s, 1H), 7.65 (d, J=4 Hz, 1H), 7.62 (d, J=4.4 Hz, 1H), 7.3 (d, J=4.4 Hz, 1H), 7.25 (d, J=4 Hz, 1H), 2.3 (s, 3H), 2.28 (s, 3H).

b) 2-[5-(3,4-dimethylphenyl)-furan-2-yl]-9-hydroxy-3H-naphtho[1,2-d]imidazole-7-carboxylic acid:

To an agitated solution of 5-(3,4-dimethylphenyl)-furan-2-carbaldehyde (0.030 g, 0.15 mmol) in EtOH (0.80 mL) was added 7,8-diamino-1-hydroxy-3-naphthoic acid dihydrochloride (0.029 g, 0.10 mmol) and sodium bisulfite (30 mg) in water (0.20 mL). The solution was heated to 60° C. and agitated overnight. The solution was cooled to room temperature, the tan precipitate was isolated by filtration and washed with water and ethyl acetate to provide the title compound (0.007 g, 15%) MS(ES) m/z 399 [M–H].

EXAMPLE 20

2-[4-(3,4-dimethylphenyl)-furan-2-yl]-9-hydroxy-3H-naphtho[1,2-d]imidazole-7-carboxylic acid (Compound 138)

Follow the procedure of Experimental 19a), except substituting 4-bromofuran-2-carbaldehyde for 5-bromofuran-2-carbaldehyde, the crude product was obtained. Follow the procedure of Experiment 19b), except substituting the above crude product for 5-(3,4-dimethylphenyl)-furan-2-carbaldehyde, the title compound was prepared as a yellow solid. (0.03 g, 56%). MS(ES) m/z 399 [M+H].

EXAMPLE 21

9-Hydroxy-2-[5-(3-isopropylphenyl)-furan-2-yl]-3H-naphtho[1,2-d]imidazole-7-carboxylic acid (Compound 139)

a) 5-(3-isopropylphenyl)-furan-2-carbaldehyde:

Follow the procedure of Example 19a), except substituting 3-isopropylphenyl boronic acid for 3,4-dimethylphenylboronic acid, the title compound was prepared. $^1$H NMR (300 MHz, CDCl3)) δ 9.65 (s, 1H), 7.7(s, 1H), 7.65 (d, J=6.2 Hz, 1H), 7.38 (t, J=7.7 Hz, 1H), 7.32 (d, J=3.8 Hz, 1H), 7.28(d, J=6.2 Hz, 1H), 6.8 (d, J=3.8 Hz, 1H), 3.0 (m, 1H), 1.39 (s, 3H), 1.38(s, 3H).

b) 9-Hydroxy-2-[5-(3-isopropylphenyl)-furan-2-yl]-3H-naphtho[1,2-d]imidazole-7-carboxylic acid:

Follow the procedure of Example 19b), except substituting 5-(3-isopropylphenyl)-furan-2-carbaldehyde for 5-(3,4-dimethylphenyl)-furan-2-carbaldehyde, the title copmpound was prepared as a yellow solid. (0.03 g, 66%). MS(ES) m/z 413 [M+H].

EXAMPLE 22

9-Hydroxy-2-[4-(4-tert-butylphenyl)-furan-2-yl]-3H-naphtho[1,2-d]imidazole-7-carboxylic acid (Compound 140)

a) 4-(4-tert-butylphenyl)-furan-2-carbaldehyde:

Follow the procedure of Example 19a), except substituting 4-tert-butylphenyl boronic acid for 3,4-dimethylphenylboronic acid and 4-bromofuran-2-carbaldehyde for 5-bromofuran-2-carbaldehyde, the title compound was prepared (0.022 g, 2.5%). $^1$H NMR (300 MHz, CDCl$_3$)) δ 9.69 (s, 1H), 7.94(s, 1H), 7.52 (s, 1H), 7.45 (s, 4H), 1.32 (s, 9H).

b) 9-Hydroxy-2-[4-(4-tert-butylphenyl)-furan-2-yl]-3H-naphtho[1,2-d]imidazole-7-carboxylic acid:

Follow the procedure of Example 19b), except substituting 4-(4-tert-butylphenyl)-furan-2-carbaldehyde for 5-(3,4-dimethylphenyl)-furan-2-carbaldehyde, the title copmpound was prepared as a yellow solid. (0.036 g, 84%). MS(ES) m/z 427 [M+H].

EXAMPLE 23

9-Hydroxy-2-[5-(4-tert-butylphenyl)-furan-2-yl]-3H-naphtho[1,2-d]imidazole-7-carboxylic acid (Compound 141)

a) 5-(4-tert-butylphenyl)-furan-2-carbaldehyde:

Follow the procedure of Example 19a), except substituting 4-tert-butylphenyl boronic acid for 3,4-dimethylphenylboronic acid, the title compound was prepared (0.05 g, 8.5%). $^1$H NMR (300 MHz, CDCl$_3$)) δ 9.62 (s, 1H), 7.75(d, J=8.8 Hz, 2H), 7.49 (d, J=8.8 Hz, 2H), 7.31 (d, J=7.0 Hz, 1H), 6.81 (d, J=7.0 Hz, 1H), 1.32 (s, 9H).

b) 9-Hydroxy-2-[5-(4-tert-butylphenyl)-furan-2-yl]-3H-naphtho[1,2-d]imidazole-7-carboxylic acid:

Follow the procedure of Example 19b), except substituting 5-(4-tert-butylphenyl)-furan-2-carbaldehyde for 5-(3,4-dimethylphenyl)-furan-2-carbaldehyde, the title copmpound was prepared as a yellow solid. (0.035 g, 83%). MS(ES) m/z 427 [M+H].

EXAMPLE 24

2-[5-(3,4-dimethylphenyl)-thiophen-2-yl]-9-hydroxy-3H-naphtho[1,2-d]imidazole-7-carboxylic acid (Compound 142)

a) 5-(3,4-dimethylphenyl)-thiophene-2-carbaldehyde:

Follow the procedure of Example 19a), except substituting 5-bromothiophene-2-carbaldehyde for 5-bromofuran-2-carbaldehyde, the title compound was prepared (0.35 g, 81%). $^1$H NMR (300 MHz, CDCl3)) δ 9.87 (s, 1H), 7.72(d, J=3.8 Hz, 1H), 7.45 (s, 1H), 7.42 (d, J=7.8 Hz, 1H), 7.35 (d, J=3.8 Hz, 1H), 7.18 (d, J=7.8 Hz, 1H), 2.32 (s, 3H), 2.30 (s, 3H).

b) 2-[5-(3,4-dimethylphenyl)-thiophen-2-yl]-9-hydroxy-3H-naphtho[1,2-d]imidazole-7-carboxylic acid:

Follow the procedure of Example 19b), except substituting 5-(3,4-dimethylphenyl)-thiophene-2-carbaldehyde for 5-(3,4-dimethylphenyl)-furan-2-carbaldehyde and, the title copmpound was prepared as a yellow solid. (0.035 g, 83%). MS(ES) m/z 427 [M+H].

EXAMPLE 25

2-[4-(3,4-dimethylphenyl)-thiophen-2-yl]-9-hydroxy-3H-naphtho[1,2-d]imidazole-7-carboxylic acid (Compound 143)

a) 4-(3,4-dimethylphenyl)-thiophene-2-carbaldehyde:

Follow the procedure of Example 19a), except substituting 4-bromothiophene-2-carbaldehyde for 5-bromofuran-2-carbaldehyde, the title compound was prepared (0.24 g, 55%). $^1$H NMR (300 MHz, CDCl3)) δ 9.87 (s, 1H), 8.0 (s, 1H), 7.8 (s, 1H), 7.38 (s, 1H), 7.33 (d, J=7.9 Hz, 1H), 7.20 (d, J=7.9 Hz, 1H), 2.33 (s, 3H), 2.30 (s, 3H).

b) 2-[4-(3,4-dimethylphenyl)-thiophen-2-yl]-9-hydroxy-3H-naphtho[1,2-d]imidazole-7-carboxylic acid:

Follow the procedure of Example 19b), except substituting 4-(3,4-dimethylphenyl)-thiophene-2-carbaldehyde for 5-(3,4-dimethylphenyl)-furan-2-carbaldehyde, the title copmpound was prepared as a solid. (0.04 g, 89%). MS(ES) m/z 415 [M+H].

EXAMPLE 26

2-[4-(4-tert-butylphenyl)-thiophen-2-yl]-9-hydroxy-3H-naphtho[1,2-d]imidazole-7-carboxylic acid (Compound 144)

a) 4-(4-tert-butylphenyl)-thiophene-2-carbaldehyde:

Follow the procedure of Example 19a), except substituting 4-bromothiophene-2-carbaldehyde for 5-bromofuran-2-carbaldehyde and 4-tert-butylphenylboronic acid for 3,4-dimethylphenylboronic acid, the title compound was prepared. $^1$H NMR (300 MHz, CDCl3)) δ 9.95 (s, 1H), 8.05 (s, 1H), 7.85 (s, 1H), 7.52 (s, 2H), 7.45 (s, 2H), 1.34 (s, 9H).

b) 2-[4-(4-tert-butylphenyl)-thiophen-2-yl]-9-hydroxy-3H-naphtho[1,2-d]imidazole-7-carboxylic acid:

Follow the procedure of Example 19b), except substituting 4-(4-tert-butylphenyl)-thiophene-2-carbaldehyde for 5-(3,4-dimethylphenyl)-furan-2-carbaldehyde, the title compound was prepared as a solid. (0.035 g, 79%).MS(ES) m/z 443 [M+H].

EXAMPLE 27

2-[5-(4-tert-butylphenyl)-thiophen-2-yl]-9-hydroxy-3H-naphtho[1,2-d]imidazole-7-carboxylic acid (Compound 145)

a) 5-(4-tert-butylphenyl)-thiophene-2-carbaldehyde:

Follow the procedure of Example 19a), except substituting 5-bromothiophene-2-carbaldehyde for 5-bromofuran-2-carbaldehyde and 4-tert-butylphenylboronic acid for 3,4-dimethylphenylboronic acid, the title compound was prepared. $^1$H NMR (300 MHz, CDCl3)) δ 9.85 (s, 1H), 7.72 (d, J=5.0 Hz, 1H), 7.62 (d, J=8.4 Hz, 2H), 7.49 (d, J=8.4 Hz, 2H), 7.32 (d, J=5.0, 1H), 1.31 (s, 9H).

b) 2-[5-(4-tert-butylphenyl)-thiophen-2-yl]-9-hydroxy-3H-naphtho[1,2-d]imidazole-7-carboxylic acid:

Follow the procedure of Example 19b), except substituting 5-(4-tert-butylphenyl)-thiophene-2-carbaldehyde for 5-(3,4-dimethylphenyl)-furan-2-carbaldehyde, the title copmpound was prepared as a solid. (0.04 g, 90%). MS(ES) m/z 443 [M+H].

EXAMPLE 28

2-[5-(3,4-dichlorophenyl)furan-2-yl]-9-hydroxy-3H-naphtho[1,2-d]imidazole-7-carboxylic acid (Compound 146)

a) 2-bromo-5-(1,1-dimethoxymethyl)furan:

A solution of 5-bromo-2-furaldehyde (5.0 g, 0.028 mol), trimethylorthoformate (3.9 g, 0.036 mmol), and pyridinium-p-toluenesulfonate (0.01 g) in 20 ml methanol was heated to reflux under argon for 18 hrs. The solution was concentrated to leave a pale yellow oil. The oil is diluted with ethyl acetate and passed through basic alumina which was pre-washed with ethyl acetate. The organic portion was concentrated under reduced pressure to give pale yellow oil (6.0 g, 97%). $^1$H NMR (300 MHz, CDCl3)) δ 6.38 (d, J=3.1 Hz, 1H), 6.29 (d, J=3.2 Hz, 1H), 3.3 (s, 6H).

b) 2-tri-n-butylstanyl-5-(1,1-dimethoxymethyl)furan:

2-bromo-5-(1,1-dimethoxymethyl)furan (3 g, 0.013 mol) dissolved in 35 ml THF was cooled to −78° C., and was then added 1.6M n-butyllithium in hexane (0.96 g, 0.015 mmol) slowly. After stirred at −78° C. for 10 min., it was added tributyltin chloride (4.42 g, 0.013 mol) and was warmed up to room temperature. The reaction mixture was quenched with methanol and washed with water. The organics were combined, dried over MgSO$_4$ and concentrated under reduced pressure to give the title as yellow oil. (5.95 g, 99%). $^1$H NMR (300 MHz, CDCl$_3$)) δ 6.5 (d, J=3.1 Hz, 1H), 6.4 (d, J=3.2 Hz, 1H), 5.45 (s, 1H), 3.32 (s, 6H), 1.6 (m, 6H), 1.35 (m, 6H), 1.15 (m, 6H), 0.9 (m, 9H).

c) 2-(3,4-dichlorophenyl)-5-(1,1-dimethoxymethyl)furan:

To a solution of 2-tri-n-butylstanyl-5-(1,1-dimethoxymethyl)furan (5.85 g, 0.013 mol) and 1-bromo-3,4-dichlorobenzene (2.56 g, 0.011 mol) in 25 ml distilled THF was added palladium (II) chloride bis triphenylphosphine (0.56 mmol) and was heated to reflux for 18 hrs. After the reaction mixture was cooled to room temperature, it was diluted with water and extracted twice with ethyl acetate. The organics were washed brine, dried over MgSO$_4$, and concentrated to a dark oil. The dark oil was further purified through column chromatography on SiO$_2$ (Hexane:EtOAc= 9:1) to give the title compound as a pale yellow oil (2.16 g, 68%). $^1$H NMR (300 MHz, CDCl$_3$) δ 7.8(s, 1H), 7.5 (dd, J=1.9 Hz, 8.3 Hz, 1H), 7.48 (d, J=8.3 Hz, 1H), 6.62 (d, J=3.1 Hz, 1H), 6.5 (d, J=3.2 Hz, 1H), 5.45 (s, 1H), 3.4 (s, 6H).

d) 5-(3,4-dichlorophenyl)furan-2-carbaldehyde:

2-(3,4-dichlorophenyl)-5-(1,1-dimethoxymethyl)furan (2.15 g, 7.5 mmol) in 35 ml acetone was added pyridinium-p-toluenesulfonate and stirred at room temperature for 18 hrs. After concentrated under reduced pressure, the mixture was taken up with ethyl acetate, washed with water and brine. The organics were dried over MgSO$_4$, filtered and concentrated to give the title compound as a yellow solid (1.56 g, 92%). $^1$H NMR (300 MHz, CDCl$_3$) δ 9.7 (s, 1H), 7.9(s, 1H), 7.65 (d, J=8.3 Hz, 1H), 7.55 (d, J=8.3 Hz, 1H)), 7.3 (d, J=3.1 Hz, 1H), 6.82 (d, J=3.2 Hz, 1H). MS(ES) m/z 241 [M+H].

e) 2-[5-(3,4-dichlorophenyl)furan-2-yl]-9-hydroxy-3H-naphtho[1,2-d]imidazole-7-carboxylic acid:

Follow the procedure of Example 19b), except substituting 5-(3,4-dichlorophenyl)furan-2-carbaldehyde for 5-(3,4-dimethylphenyl)-furan-2-carbaldehyde, the title copmpound was prepared as a yellow solid. (0.06 g, 91%) MS(ES) m/z 439 [M+H].

EXAMPLE 29

2-[5-benzo[b]thiophen-2-yl-furan-2-yl]-9-hydroxy-3H-naphtho[1,2-d]imidazole-7-carboxylic acid (Compound 147)

a) 2-benzo[b]thiophen-2-yl-5-(1,1-dimethoxymethyl)-furan:

Follow the procedure of Example 19a), except substituting 2-bromo-5-(1,1-dimethoxymethyl)furan for 5-bromofuran-2-carbaldehyde and thionaphthene-2-boronic acid for 3,4-dimethylphenylboronic acid, the title compound was prepared as a yellow solid (2.16 g, 52%). $^1$H NMR (300 MHz, CDCl$_3$)) δ 7.8 (d, J=7.4 Hz, 1H), 7.78 (d, J=7.4 Hz, 1H), 7.5 (s, 1H)), 7.3 (m, 2H), 6.6 (d, J=3.2 Hz, 1H), 6.5 (d, J=3.1 Hz, 1H), 5.5 (s, 1H), 3.4 (s, 6H).

b) 5-benzo[b]thiophen-2-yl-furan-2-carbaldehyde:

Follow the procedure of Example 28d), except substituting 2-benzo[b]thiophen-2-yl-5-(1,1-dimethoxymethyl)furan for 2-(3,4-dichlorophenyl)-5-(1,1-dimethoxymethyl)furan, the title compound was prepared as a solid (1.65 g, 92%). MS(ES) m/z 229 [M+H].

c) 2-[5-benzo[b]thiophen-2-yl-furan-2-yl]-9-hydroxy-3H-naphtho[1,2-d]imidazole-7-carboxylic acid:

Follow the procedure of Example 19b), except substituting 5-benzo[b]thiophen-2-yl-furan-2-carbaldehyde for 5-(3,4-dimethylphenyl)-furan-2-carbaldehyde, the title copmpound was prepared as a solid. (0.06 g, 91%). MS(ES) m/z 427 [M+H].

EXAMPLE 30

2-[4'-tert-butyl-6-methoxybiphenyl-3-yl]-9-hydroxy-3H-naphtho[1,2-d]imidazole-7-carboxylic acid (Compound 148)

a) 4'-tert-butyl-6-methoxybiphenyl-3-carbaldehyde:

Follow the procedure of Example 19a), except substituting 1-bromo-4-tert-butylbenzene for 5-bromofuran-2-carbaldehyde and 5-formyl-2-methoxyphenylboronic acid for 3,4-dimethylphenylboronic acid, the title compound was prepared as a solid. MS(ES) m/z 269 [M+H].

b) 2-[4'-tert-butyl-6-methoxybiphenyl-3-yl]-9-hydroxy-3H-naphtho[1,2-d]imidazole-7-carboxylic acid:

Follow the procedure of Example 19b), except substituting 4'-tert-butyl-6-methoxybiphenyl-3-carbaldehyde for 5-(3,4-dimethylphenyl)-furan-2-carbaldehyde, the title copmpound was prepared as a solid. (0.011 g, 12%). MS(ES) m/z 467 [M+H].

EXAMPLE 31

2-[6-fluoro-3',4'-dimethylbiphenyl-3-yl]-9-hydroxy-3H-naphtho[1,2-d]imidazole-7-carboxylic acid (Compound 149)

a) 6-fluoro-3',4'-dimethylbiphenyl-3-carbaldehyde:

Follow the procedure of Example 19a), except substituting 3-bromo-4-fluorobenzaldehyde for 5-bromofuran-2-carbaldehyde, the title compound was prepared as a solid. MS(ES) m/z 229 [M+H].

b) 2-[6-fluoro-3',4'-dimethylbiphenyl-3-yl]-9-hydroxy-3H-naphtho[1,2-d]imidazole-7-carboxylic acid:

Follow the procedure of Example 19b), except substituting 6-fluoro-3',4'-dimethylbiphenyl-3-carbaldehyde for 5-(3,4-dimethylphenyl)-furan-2-carbaldehyde, the title copmpound was prepared as a solid. (0.004 g, 5%). MS(ES) m/z 427 [M+H].

EXAMPLE 32

2-[4-fluoro-3',4'-dimethylbiphenyl-3-yl]-9-hydroxy-3H-naphtho[1,2-d]imidazole-7-carboxylic acid (Compound 150)

a) 4-fluoro-3',4'-dimethylbiphenyl-3-carbaldehyde:

Follow the procedure of Example 19a), except substituting 5-bromo-2-fluorobenzaldehyde for 5-bromofuran-2- carbaldehyde, the title compound was prepared as a solid. $^1$H NMR (300 MHz, CDCl$_3$)) δ 10.3 (s, 1H), 8.05 (m, 2H), 7.5 (m, 2H), 7.4 (d, J=7.5 Hz, 1H)), 7.23 (d, J=7.5 Hz, 1H).

b) 2-[4-fluoro-3',4'-dimethylbiphenyl-3-yl]-9-hydroxy-3H-naphtho[1,2-d]imidazole-7-carboxylic acid:

Follow the procedure of Example 19b), except substituting 4-fluoro-3',4'-dimethylbiphenyl-3-carbaldehyde for 5-(3,4-dimethylphenyl)-furan-2-carbaldehyde, the title copmpound was prepared as a solid. (0.006 g, 6%). MS(ES) m/z 427 [M+H].

EXAMPLE 33

2-[4'-tert-butyl-4-fluorobiphenyl-3-yl]-9-hydroxy-3H-naphtho[1,2-d]imidazole-7-carboxylic acid (Compound 151)

a) 4'-tert-butyl-4-fluorobiphenyl-3-carbaldehyde:

Follow the procedure of Example 19a), except substituting 5-bromo-2-fluorobenzaldehyde for 5-bromofuran-2-carbaldehyde and 4-tert-butylphenyl boronic acid for 3,4-dimethylphenylboronic acid, the title compound was prepared as a solid. $^1$H NMR (300 MHz, DMSO-d$_6$)) δ 10.2 (s, 1H), 8.1 (m, 2H), 7.65 (d, J=5.0 Hz, 2H), 7.59 (s, 1H), 7.55 (d, J=5.0 Hz, 2H), 1.35 (s, 9H).

b) 2-[4'-tert-butyl-4-fluorobiphenyl-3-yl]-9-hydroxy-3H-naphtho[1,2-d]imidazole-7-carboxylic acid:

Follow the procedure of Example 19b), except substituting 4'-tert-butyl-4-fluorobiphenyl-3-carbaldehyde for 5-(3,4-dimethylphenyl)-furan-2-carbaldehyde, the title compound was prepared as a solid. (0.002 g, 3%). MS(ES) m/z 455 [M+H].

EXAMPLE 34

2-[4'-trifluoromethylbiphenyl-3-yl]-9-hydroxy-3H-naphtho[1,2-d]imidazole-7-carboxylic acid (Compound 152)

a) 4'-trifluoromethylbiphenyl-3-carbaldehyde:

Follow the procedure of Example 19a), except substituting 5-bromo-2-fluorobenzaldehyde for 5-bromofuran-2-carbaldehyde and 4-tert-butylphenyl boronic acid for 3,4-dimethylphenylboronic acid, the title compound was prepared as a solid. MS(ES) m/z 251 [M+H].

b) 2-[4'-trifluoromethylbiphenyl-3-yl]-9-hydroxy-3H-naphtho[1,2-d]imidazole-7-carboxylic acid:

Follow the procedure of Example 19b), except substituting 4'-trifluoromethylbiphenyl-3-carbaldehyde for 5-(3,4-dimethylphenyl)-furan-2-carbaldehyde, the title compound was prepared as a solid. (0.016 g, 22%). MS(ES) m/z 449 [M+H].

EXAMPLE 35

2-[4'-tert-butyl-6-fluoro-biphenyl-3-yl]-9-hydroxy-3H-naphtho[1,2-d]imidazole-7-carboxylic acid (Compound 153)

a) 4'-tert-butyl-6-fluorobiphenyl-3-carbaldehyde:

Follow the procedure of Example 19a), except substituting 3-bromo-4-fluorobenzaldehyde for 5-bromofuran-2-carbaldehyde and 4-tert-butylphenyl boronic acid for 3,4-dimethylphenylboronic acid, the title compound was prepared as a solid. MS(ES) m/z 257 [M+H], 513 [2M+H].

b) 2-[4'-tert-butyl-6-fluoro-biphenyl-3-yl]-9-hydroxy-3H-naphtho[1,2-d]imidazole-7-carboxylic acid:

Follow the procedure of Example 19b), except substituting 4'-tert-butyl-6-fluorobiphenyl-3-carbaldehyde for 5-(3,4-dimethylphenyl)-furan-2-carbaldehyde, the title copmpound was prepared as a solid. (0.039 g, 86%). MS(ES) m/z 455 [M+H].

EXAMPLE 36

2-[5-(4-tert-butylphenyl)-pyridin-3-yl]-9-hydroxy-1H-naphtho[1,2-d]imidazole-7-carboxylic acid (Compound 154)

a) 5-(4-butylphenyl)-pyridine-3-carbaldehyde:

Follow the procedure of example 1a) except substituting 5-bromopyridine-3-carbaldehyde for 3-bromo-2-methoxybenzaldehyde and 4-tert-butylphenylboronic acid for 2-methylphenylboronic acid, the title compound was prepared as a solid. MS(ES) m/z 240 [M+H].

b) 2-[5-(4-tert-butylphenyl)-pyridin-3-yl]-9-hydroxy-1H-naphtho[1,2-d]imidazole-7-carboxylic acid:

Follow the procedure of example 1c) except substituting 5-(4-butylphenyl)-pyridine-3-carbaldehyde for 2-methoxy-3-(2'-methylphenyl)benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.025 g, 57%). MS(ES) m/z 438 [M+H].

EXAMPLE 37

2-[(2-fluoro-4-trifluoromethylbiphenyl)-3-yl]-9-hydroxy-1H-naphtho[1,2-d]imidazole-7-carboxylic acid (Compound 155)

a) 2'-fluoro-3'-trifluoromethylbiphenyl-3-carbaldehyde:

Follow the procedure of example 1a) except substituting 4-trifluoromethyl-2-fluorobromobenzene for 3-bromo-2-methoxybenzaldehyde and 3-formylphenylboronic acid for 2-methylphenylboronic acid, the title compound was prepared as a solid. MS(ES) m/z 269 [M+H].

b) 2-[(2-fluoro-4-trifluoromethylbiphenyl)-3-yl]-9-hydroxy-1H-naphtho[1,2-d]imidazole-7-carboxylic acid:

Follow the procedure of example 1c) except substituting 2'-fluoro-3'-trifluoromethylbiphenyl-3-carbaldehyde for 2-methoxy-3-(2'-methyl phenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.035 g, 57%). MS(ES) m/z 467 [M+H].

EXAMPLE 38

2-[(2,5-difluoro-4-trifluoromethylbiphenyl)-3-yl]-9-hydroxy-1H-naphtho[1,2-d]imidazole-7-carboxylic acid (Compound 156)

a) 2',5'-difluoro-3'-trifluoromethylbiphenyl-3-carbaldehyde:

Follow the procedure of example 1a) except substituting 4-trifluoromethyl-2,5-difluorobromobenzene for 3-bromo-2-methoxybenzaldehyde and 3-formylphenylboronic acid for 2-methylphenylboronic acid, the title compound was prepared as a solid. MS(ES) m/z 287 [M+H].

b) 2-[(2,5-difluoro-4-trifluoromethylbiphenyl)-3-yl]-9-hydroxy-1H-naphtho[1,2-d]imidazole-7-carboxylic acid:

Follow the procedure of example 1c) except substituting 2,5'-difluoro-3'-trifluoromethylbiphenyl-3-carbaldehyde for 2-methoxy-3-(2'-methyl phenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.035 g, 67%). MS(ES) m/z 485 [M+H].

EXAMPLE 39

2-[(4-fluoro-4'-trifluoromethylbiphenyl)-3-yl]-9-hydroxy-1H-naphtho[1,2-d]imidazole-7-carboxylic acid (Compound 157)

a) 4-fluoro-4'-trifluoromethylbiphenyl-3-carbaldehyde:

Follow the procedure of example 1a) except substituting 3-bromo-4-fluorobenzaldehyde for 3-bromo-2-methoxybenzaldehyde and 4-trifluoromethylbenzeneboronic acid for 2-methylphenylboronic acid, the title compound was prepared as a solid. MS(ES) m/z 269 [M+H].

b) 2-[(4-fluoro-4'-trifluoromethylbiphenyl)-3-yl]-9-hydroxy-1H-naphtho[1,2-d]imidazole-7-carboxylic acid:

Follow the procedure of example 1c) except substituting 4-fluoro-4'-trifluoromethylbiphenyl-3-carbaldehyde for 2-methoxy-3-(2'-methyl phenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.042 g, 90%). MS(ES) m/z 467 [M+H].

EXAMPLE 40

2-[5-(4-trifluoromethylphenyl)-furan-2-yl]-9-hydroxy-3H-naphtho[1,2-d]imidazole-7-carboxylic acid (Compound 158)

a) 5-(4-trifluoromethylphenyl)-furan-2-carbaldehyde:

Follow the procedure of example 1a) except substituting 5-bromofuran-2-carbaldehyde for 3-bromo-2-methoxybenzaldehyde and trifluoromethyl phenyl boronic acid for 2-methylphenylboronic acid, the title compound was prepared as a solid. MS(ES) m/z 227 [M+H]

b) 2-[5-(4-trifluoromethylphenyl)-furan-2-yl]-9-hydroxy-3H-naphtho[1,2-d]imidazole-7-carboxylic acid:

Follow the procedure of example 1c) except substituting 5-(4-trifluoromethylphenyl)-furan-2-carbaldehyde for 2-methoxy-3-(2'-methyl phenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.044 g, 94%). MS(ES) m/z 439 [M+H].

EXAMPLE 41

2-[4-(4-trifluoromethylphenyl)-thiophen-2-yl]-9-hydroxy-3H-naphtho[1,2-d]imidazole-7-carboxylic acid (Compound 159)

a) 4-(4-trifluoromethylphenyl)-thiophene-2-carbaldehyde:

Follow the procedure of example 1a) except substituting 4-bromothiophene-2-carbaldehyde for 3-bromo-2-methoxybenzaldehyde and trifluoro methyl phenyl boronic acid for 2-methylphenylboronic acid, the title compound was prepared as a solid. MS(ES) m/z 257 [M+H].

b) 2-[4-(4-trifluoromethylphenyl)-thiophen-2-yl]-9-hydroxy-3H-naphtho[1,2-d]imidazole-7-carboxylic acid:

Follow the procedure of example 1c) except substituting 4-(4-trifluoromethylphenyl)-thiophene-2-carbaldehyde for 2-methoxy-3-(2'-methyl phenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.041 g, 84%). MS(ES) m/z 455 [M+H].

EXAMPLE 42

2-(4'-ethylbiphenyl-3-yl)-9-hydroxy-3H-naphtho[1,2-d]imidazole-7-carboxylic acid (Compound 160)

a) 4'-ethylbiphenyl-3-carbaldehyde:

Follow the procedure of example 1a) except substituting 4-ethyl-bromobenzene for 3-bromo-2-methoxybenzaldehyde and 3-formylbenzene boronic acid for 2-methylphenylboronic acid, the title compound was prepared as a solid. MS(ES) m/z 211 [M+H].

b) 2-(4'-ethylbiphenyl-3-yl)-9-hydroxy-3H-naphtho[1,2-d]imidazole-7-carboxylic acid:

Follow the procedure of example 1c) except substituting 4'-ethylbiphenyl-3-carbaldehyde for 2-methoxy-3-(2'-methyl phenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.046 g, 99%). MS(ES) m/z 409 [M+H].

EXAMPLE 43

2-(4'-propylbiphenyl-3-yl)-9-hydroxy-3H-naphtho[1,2-d]imidazole-7-carboxylic acid (Compound 161)

a) 4'-propylbiphenyl-3-carbaldehyde:

Follow the procedure of example 1a) except substituting 4-propyl-bromobenzene for 3-bromo-2-methoxybenzaldehyde and 3-formylbenzene boronic acid for 2-methylphenylboronic acid, the title compound was prepared as a solid. MS(ES) m/z 225 [M+H].

b) 2-(4'-propylbiphenyl-3-yl)-9-hydroxy-3H-naphtho[1,2-d]imidazole-7-carboxylic acid:

Follow the procedure of example 1c) except substituting 4'-propylbiphenyl-3-carbaldehyde for 2-methoxy-3-(2'-methylphenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.05 g, 99%). MS(ES) m/z 423 [M+H].

EXAMPLE 44

2-(4'-butylbiphenyl-3-yl)-9-hydroxy-3H-naphtho[1,2-d]imidazole-7-carboxylic acid (Compound 162)

a) 4'-butylbiphenyl-3-carbaldehyde:

Follow the procedure of example 1a) except substituting 4-butyl-bromobenzene for 3-bromo-2-methoxybenzaldehyde and 3-formylbenzene boronic acid for 2-methylphenylboronic acid, the title compound was prepared as a solid. MS(ES) m/z 239 [M+H].

b) 2-(4'-butylbiphenyl-3-yl)-9-hydroxy-3H-naphtho[1,2-d]imidazole-7-carboxylic acid:

Follow the procedure of example 1c) except substituting 4'-butyllbiphenyl-3-carbaldehyde for 2-methoxy-3-(2'-methylphenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.048 g, 99%). MS(ES) m/z 437 [M+H].

EXAMPLE 45

2-(4'-carboxy-3'-methylbiphenyl-3-yl)-9-hydroxy-3H-naphtho[1,2-d]imidazole-7-carboxylic acid (Compound 163)

a) 3'-formyl-3-methylbiphenyl-4-carboxylic acid:

Follow the procedure of example 1a) except substituting 4-bromo-2-methylbenzoic acid for 3-bromo-2-methoxybenzaldehyde and 3-formylbenzene boronic acid for 2-methylphenylboronic acid, the title compound was prepared as a solid. MS(ES) m/z 241 [M+H].

b) 2-(4'-carboxy-3'-methylbiphenyl-3-yl)-9-hydroxy-3H-naphtho[1,2-d]imidazole-7-carboxylic acid:

Follow the procedure of example 1c) except substituting 3'-formyl-3-methylbiphenyl-4-carboxylic acid for 2-methoxy-3-(2'-methylphenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.060 g, 99%). MS(ES) m/z 439 [M+H].

EXAMPLE 46

2-(4'-cyano-3'-methylbiphenyl-3-yl)-9-hydroxy-3H-naphtho[1,2-d]imidazole-7-carboxylic acid (Compound 164)

a) 3'-formyl-3-methylbiphenyl-4-carbonitrile:

Follow the procedure of example 1a) except substituting 4-cyano-3-methylbromobenzene for 3-bromo-2- methoxybenzaldehyde and 3-formylbenzene boronic acid for 2-methylphenylboronic acid, the title compound was prepared as a solid. MS(ES) m/z 222 [M+H].

b) 2-(4'-cyano-3'-methylbiphenyl-3-yl)-9-hydroxy-3H-naphtho[1,2-d]imidazole-7-carboxylic acid:

Follow the procedure of example 1c) except substituting 3'-formyl-3-methylbiphenyl-4-carbonitrile for 2-methoxy-3-(2'-methylphenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.065 g, 99%). MS(ES) m/z 420 [M+H].

EXAMPLE 47

2-(4'-fluoro-3'-methylbiphenyl-3-yl)-9-hydroxy-3H-naphtho[1,2-d]imidazole-7-carboxylic acid (Compound 165)

a) 4'-fluoro-3'-methylbiphenyl-3-carbaldehyde:

Follow the procedure of example 1a) except substituting 3-bromobenzaldehyde for 3-bromo-2-methoxybenzaldehyde and 4-fluoro-3-methylbenzene boronic acid for 2-methylphenylboronic acid, the title compound was prepared as a solid. MS(ES) m/z 215 [M+H].

b) 2-(4'-fluoro-3'-methylbiphenyl-3-yl)-9-hydroxy-3H-naphtho[1,2-d]imidazole-7-carboxylic acid:

Follow the procedure of example 1c) except substituting 4'-fluoro-3'-methylbiphenyl-3-carbaldehyde for 2-methoxy-3-(2'-methylphenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.057 g, 99%). MS(ES) m/z 413 [M+H].

EXAMPLE 48

2-[1-(4-tert-butylphenyl)-1H-pyrazol-4-yl]-9-hydroxy-3H-naphtho[1,2-d]imidazole-7-carboxylic acid (Compound 166)

a) 1-(4-tert-butylphenyl)-1H-pyrazole:

To the mixture of 4-tert butyl benzene boronic acid (0.1 g, 0.56 mmol), pyrazole (0.02 g, 0.28 mmol), anhydrous cupric acetate(0.1 g, 0.56 mmol) and pyridine in methylene chloride (10 ml), was added 4Å powdered molecular sieves (0.15 g) The reaction was stirred unfer air at room temperature for 2 days. The reaction was filtered through Celite and concentrated under reduced precedure to dryness. The residue was purifed by silica gel chromatography to give the title compound. $^1$H NMR (300 MHz, CDCl$_3$) 7.9 (s, 1H), 7.72 (s, 1H), 7.65 (d, J=6.8 Hz, 2H), 7.45 (d, J=6.8 Hz, 2H), 6.45 (s, 1H), 1.3 (s, 9H). MS(ES) m/z 201 [M+H].

b) 1-(4-tert-butylphenyl)-1H-pyrazole-4-carbaldehyde:

Phosphorus oxychloride (0.075 ml, 0.5 mmol) was added dropwise slowly to a stirred solution of freshly distilled dimethylformamide (0.075 ml, 1.0 mmol) containing 1-(4-tert-butylphenyl)-1H-pyrazole (0.1 g, 0.5 mmol) at 90–100° C. After complete addition, the reaction mixture was stirred for another 4 hours under the same conditions. The reaction mixture was cooled and ice-water added. The pH was adjusted to 4 with a diluted sodium hydroxide solution and then extract with ethanol. The organic solution was washed with hydrochloric acid (1N), with a diluted solution of sodium bicarbonate and then dried over sodium sulfate. The crude product was purified by silica gel chromatography to give the title compound as a solid (0.035 g, 44%). $^1$H NMR (300 MHz, CDCl$_3$) 9.9 (s, 1H), 8.41 (s, 1H), 8.16 (s, 1H), 7.65 (d, J=6.8 Hz, 2H), 7.45 (d, J=6.8 Hz, 2H), 1.38 (s, 9H). MS(ES) m/z 229 [M+H].

c) 2-[1-(4-tert-butylphenyl)-1H-pyrazol-4-yl]-9-hydroxy-3H-naphtho[1,2-d]imidazole-7-carboxylic acid:

Follow the procedure of example 1c) except substituting 1-(4-tert-butylphenyl)-1H-pyrazole-4-carbaldehyde for 2-methoxy-3-(2'-methylphenyl) benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.030 g, 70%). $^1$H NMR (300 MHz, DMSO-d$_6$) 10.9 (s, 1H), 9.4 (s, 1H), 9.2 (s, 1H), 8.53 (d, J=7.7 Hz, 1H), 8.24 (d, J=7.7 Hz, 1H), 7.89 (m, 4H), 7.82 (d, J=6.8 Hz), 1.38 (s, 9H). MS(ES) m/z 427 [M+H].

EXAMPLE 49

2-(3',4'-difluorobiphenyl-3-yl)-9-hydroxy-3H-naphtho[1,2-d]imidazole-7-carboxylic acid (Compound 167)

a) 3',4'-difluorobiphenyl-3-carbaldehyde:

Follow the procedure of example 1a) except substituting 3-bromobenzaldehyde for 3-bromo-2-methoxybenzaldehyde and 3,4-difluorophenyl boronic acid for 2-methylphenylboronic acid, the title compound was prepared as a solid (0.305 g, 44%). MS(ES) m/z 219 [M+H].

b) 2-(3',4'-difluorobiphenyl-3-yl)-9-hydroxy-3H-naphtho[1,2-d]imidazole-7-carboxylic acid:

Follow the procedure of example 1c) except substituting 3',4'-difluorobiphenyl-3-carbaldehyde for 2-methoxy-3-(2'-methylphenyl)benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.038 g, 91%). MS(ES) m/z 417 [M+H].

EXAMPLE 50

2-[3-(9H-fluoren-2-yl)-phenyl]-9-hydroxy-3H-naphtho[1,2-d]imidazole-7-carboxylic acid (Compound 168)

a) 3-(9H-Fluoren-2-yl)-benzaldehyde:

Follow the procedure of example 1a) except substituting 2-bromo-9H-fluorene for 3-bromo-2-methoxybenzaldehyde and 3-formylphenylboronic acid for 2-methylphenylboronic acid, the title compound was prepared as a solid (0.475 g, 53%). MS(ES) m/z 271 [M+H].

b) 2-[3-(9H-fluoren-2-yl)-phenyl]-9-hydroxy-3H-naphtho[1,2-d]imidazole-7-carboxylic acid:

Follow the procedure of example 1c) except substituting 3-(9H-Fluoren-2-yl)-benzaldehyde for 2-methoxy-3-(2'-methylphenyl)benzaldehyde and 5,6-diamino-4-hydroxynaphthalene-2-carboxylic acid for 3,4-diamino-5-hydroxy-1-naphthalene sulfonic acid dihydrochloride, the title compound was prepared as a solid (0.004 g, 8%). MS(ES) m/z 469 [M+H].

EXAMPLE 51

Capsule Composition

An oral dosage form for administering a presently invented agonist of the TPO receptor is produced by filing a standard two piece hard gelatin capsule with the ingredients in the proportions shown in Table 1, below.

TABLE I

| INGREDIENTS | AMOUNTS |
|---|---|
| 2-(3-[2'-Methylphenyl]-2-methoxyphenyl)-9-hydroxy-naphth[1,2-d]imidazole-5-sulfonic acid hydrochloride (Compound 1) | 25 mg |
| Lactose | 55 mg |

TABLE I-continued

| INGREDIENTS | AMOUNTS |
| --- | --- |
| Talc | 16 mg |
| Magnesium Stearate | 4 mg |

EXAMPLE 52

Injectable Parenteral Composition

An injectable form for administering a presently invented agonist of the TPO receptor is produced by stirring 1.5% by weight of 2-(3-[4'-Methylphenyl]-2-methoxyphenyl)-9-hydroxy-naphth[1,2-d]imidazole-5-sulfonic acid hydrochloride (Compound 2) in 10% by volume propylene glycol in water.

EXAMPLE 53

Tablet Composition

The sucrose, calcium sulfate dihydrate and a presently invented agonist of the TPO receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
| --- | --- |
| 2-(3-[3',4'-Dimethylphenyl]-2-methoxyphenyl)-9-hydroxy-naphth[1,2-d]imidazole-5-sulfonic acid hydrochloride (Compound 3) | 20 mg |
| calcium sulfate dihydrate | 30 mg |
| sucrose | 4 mg |
| starch | 2 mg |
| talc | 1 mg |
| stearic acid | 0.5 mg |

Preferred among the compounds of the present invention are the following.

2-(3-[3'-Trifluoromethylphenyl]-2-methoxyphenyl)-9-hydroxy-naphth[1,2-d]imidazole-7-sulfonic acid hydrochloride;
2-(3-[2'-Methylphenyl]-2-methoxyphenyl)-9-hydroxy-naphth[1,2-d]imidazole-5-sulfonic acid hydrochloride;
2-(4-[3'-Chlorophenyl]-2-methoxyphenyl)-9-hydroxy-naphth[1,2-d]imidazole-7-sulfonic acid hydrochloride;
2-(3-[4'-Methylphenyl]-2-methoxyphenyl)-9-hydroxy-naphth[1,2-d]imidazole-5-sulfonic acid hydrochloride;
2-(3-[3',4'-Dimethylphenyl]-2-methoxyphenyl)-9-hydroxy-naphth[1,2-d]imidazole-5-sulfonic acid hydrochloride;
2-(3-[4'-Methylphenyl]-2-methoxyphenyl)-9-hydroxy-naphth[1,2-d]imidazole-7-sulfonic acid hydrochloride;
2-(3-[3',4'-Dimethylphenyl]-2-methoxyphenyl)-9-hydroxy-naphth[1,2-d]imidazole-5-sulfonic acid hydrochloride;
2-(3-[4'-Chlorophenyl]-2-methoxyphenyl)-9-hydroxy-naphth[1,2-d]imidazole-7-sulfonic acid hydrochloride;
2-(4-[4'-Methylphenyl]-2-methoxyphenyl)-9-hydroxy-naphth[1,2-d]imidazole-7-sulfonic acid hydrochloride; and
2-(4-[3',4'-Dimethylphenyl]-2-methoxyphenyl)-9-hydroxy-naphth[1,2-d]imidazole-7-sulfonic acid hydrochloride.

Most preferred among the compounds of the present invention are the following.

2-(4'-tert-butylbiphenyl-3-yl)-9-hydroxy-3H-naphtho[1,2-d]imidizole-7-sulfonic acid trifuoroacetate;
2-(4'-tert-butylbiphenyl-3-yl)-9-hydroxy-3H-naphtho[1,2-d]imidazole-7-carboxylic acid trifluoroacetate;
9-Hydroxy-2-[5-(4-tert-butylphenyl)-furan-2-yl]-3H-naphtho[1,2-d]imidazole-7-carboxylic acid;
2-[4-(4-tert-butylphenyl)-thiophen-2-yl]-9-hydroxy-3H-naphtho[1,2-d]imidazole-7-carboxylic acid; and
2-[4'-tert-butyl-4-fluorobiphenyl-3-yl]-9-hydroxy-3H-naphtho[1,2-d]imidazole-7-carboxylic acid.

While the preferred embodiments of the invention are illustrated by the above, it is to be understood that the invention is not limited to the precise instructions herein disclosed and that the right to all modifications coming within the scope of the following claims is reserved.

What is claimed is:

1. A method of treating thrombocytopenia in a mammal in need thereof which comprises administering to such mammal a therapeutically effective amount of a compound of Formula (I):

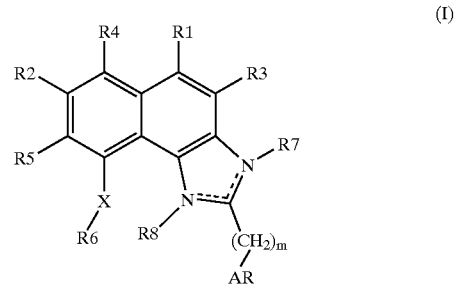

(I)

wherein:
the C ring has one double bond where indicated by the broken lines, provided that $R^8$ is absent when the nitrogen attached thereto has a double bond and provided that $R^7$ is absent when the nitrogen attached thereto has a double bond;
$R^1$, $R^2$, $R^3$, $R^4$ and $R^5$ are each independently selected from the group consisting of: hydrogen, —C(O)OR$^{11}$, —CONR$^9$R$^{10}$, —SO$_2$NR$^9$R$^{10}$, phosphonic acid, phosphinic acid, C$_{1-6}$alkyl, C$_{1-6}$alkoxy, —(CH$_2$)$_p$OR$^{11}$, nitro, cyano, halogen, —NR$^9$R$^{10}$, N-acylamino, N-sulfonylamino, —S(O)$_n$R$^{11}$, aryl, substituted aryl, alkyl, cycloalkyl, substituted cycloalkyl, protected —OH, and alkyl substituted with one or more substituents selected from the group consisting of: alkoxy, acyloxy, aryl, substituted aryl, —NR$^9$R$^{10}$, N-acylamino, oxo, hydroxy, cycloalkyl, substituted cycloalkyl, —C(O)OR$^{11}$, —C(O)NR$^9$R$^{10}$, —S(O)$_2$NR$^9$R$^{10}$, —S(O)$_n$R$^{11}$, aryloxy, nitro, cyano, halogen, and protected —OH;
where
n is 0 to 3;
p is 0 to 6;
$R^{11}$ is selected from the group consisting of: hydrogen, alkyl, cycloalkyl, C$_1$–C$_{12}$aryl, substituted alkyl, substituted cycloalkyl and substituted C$_1$–C$_{12}$aryl; and
$R^9$ and $R^{10}$ are independently selected from hydrogen, cycloalkyl, C$_1$–C$_{12}$aryl, substituted cycloalkyl, substituted C$_1$–C$_{12}$aryl, alkyl or alkyl substituted with one or more substituents selected from the group consisting of: alkoxy, acyloxy, aryloxy, —NR$^{11}$R$^{11}$, N-acylamino, oxo, hydroxy, —C(O)OR$^{11}$, —S(O)$_n$R$^{11}$, —C(O)NR$^{11}$R$^{11}$, —S(O)$_2$NR$^{11}$R$^{11}$, nitro, cyano, halogen, cycloalkyl, substituted cycloalkyl, aryl, substituted aryl and protected —OH where n and R$^{11}$ are as described above; or R$^9$ and R$^{10}$ taken together with the nitrogen to which they are attached represent a 5 to 6 member saturated ring containing up to one other heteroatom selected from oxygen and nitrogen;

R$^6$ is selected from the group consisting of: hydrogen, alkyl, cycloalkyl, C$_1$–C$_{12}$aryl, substituted alkyl, substituted cycloalkyl and substituted C$_1$–C$_{12}$aryl;

R$^7$ is absent when the nitrogen attached thereto has a double bond or selected from the group consisting of: hydrogen, alkyl, cycloalkyl, C$_1$–C$_{12}$aryl, substituted alkyl, substituted cycloalkyl and substituted C$_1$–C$_{12}$aryl;

R$^8$ is absent when the nitrogen attached thereto has a double bond or selected from the group consisting of: hydrogen, alkyl, cycloalkyl, C$_1$–C$_{12}$aryl, substituted alkyl, substituted cycloalkyl and substituted C$_1$–C$_{12}$aryl;

m is 0–6;

X is selected from the group consisting of sulfur, sulfonamido, oxygen and an amino group which may be substituted by C$_1$–C$_{10}$alkyl or benzyl;

AR is a cyclic or polycyclic aromatic ring containing from 3 to 16 carbon atoms, optionally containing one or more heteroatoms, provided that when the number of carbon atoms is 3 the aromatic ring contains at least two heteroatoms and when the number of carbon atoms is 4 the aromatic ring at least one heteroatom, optionally substituted with one or more substituents selected from the group consisting of: alkyl, substituted alkyl, cycloalkyl, substituted cycloalkyl, aryl, substituted aryl, aryloxy, hydroxy, alkoxy, acyloxy, —NR$^{12}$R$^{13}$, N-acylamino, N-sulfonylamino, nitro, cyano, halogen, —C(O)OR$^{11}$, —C(O)NR$^{12}$R$^{13}$, —S(O)$_2$NR$^{12}$R$^{13}$, —S(O)$_n$R$^{11}$, protected —OH, and alkyl substituted with one or more substituents selected from the group consisting of: alkoxy, acyloxy, aryl, substituted aryl, amino, N-acylamino, oxo, hydroxy, cycloalkyl, substituted cycloalkyl, —C(O)OR$^{11}$, —S(O)$_2$NR$^{12}$R$^{13}$, —S(O)$_n$R$^{11}$, aryloxy, nitro, cyano, halogen, and protected —OH, where n is 0 to 3;

R$^{11}$ is selected from the group consisting of: hydrogen, alkyl, cycloalkyl, C$_1$–C$_{12}$aryl, substituted alkyl, substituted cycloalkyl and substituted C$_1$–C$_{12}$aryl, and R$^{12}$ and R$^{13}$ are independently selected from the group consisting of: hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, aryloxy, —NR$^{11}$R$^{11}$, N-acylamino, oxo, hydroxy, —C(O)OR$^{11}$, —S(O)$_n$R$^{11}$, —C(O)NR$^{11}$R$^{11}$, —S(O)$_2$NR$^{11}$R$^{11}$, nitro, cyano, cycloalkyl, substituted cycloalkyl, halogen, C$_1$–C$_{12}$aryl, substituted C$_1$–C$_{12}$aryl and protected —OH, where n and R$^{11}$ are as described above; and pharmaceutically acceptable salts, hydrates, solvates and esters thereof.

2. The method of claim 1 wherein the compound administered is a compound of Formula (II):

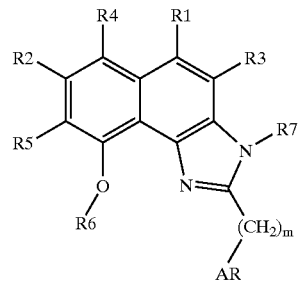

(II)

in which

R$^1$, R$^2$, R$^3$, R$^4$ and R$^5$ are each independently selected from the group consisting of: carboxylic acid, sulfonic acid, hydrogen, C$_{1-4}$alkoxy, C$_{1-6}$alkyl and halogen;

R$^6$ is selected from the group consisting of: hydrogen, alkyl, cycloalkyl, C$_1$–C$_{12}$aryl and substituted alkyl;

R$^7$ is selected form the group consisting of: hydrogen, alkyl, cycloalkyl, C$_1$–C$_{12}$aryl and substituted alkyl;

m is 0–3; and

AR is cyclic or polycyclic aromatic C$_3$–C$_{14}$, optionally containing from one to three heteroatoms, provided that when C is 3 the aromatic ring contains at least two heteroatoms and when C is 4 the aromatic ring contains at least one heteroatom, and optionally substituted with one or more substituents selected from the group consisting of: alkyl, substituted alkyl, C$_1$–C$_{12}$aryl, substituted cycloalkyl, substituted C$_1$–C$_{12}$aryl, aryloxy, —NR$^{11}$R$^{11}$, hydroxy, alkoxy, cycloalkyl, amino, nitro, cyano, halogen and protected —OH, where R$^{11}$ is selected from the group consisting of: hydrogen, alkyl, cycloalkyl, C$_1$–C$_{12}$aryl, substituted alkyl, substituted cycloalkyl and substituted C$_1$–C$_{12}$aryl;

and pharmaceutically acceptable salts, hydrates, solvates and esters thereof.

3. The method of claim 2 wherein the compound administered is a compound of Formula (II), in which R$^1$, R$^2$, R$^3$, R$^4$ and R$^5$ are each independently selected from carboxylic acid, sulfonic acid, hydrogen, C$_{1-3}$alkoxy, C$_{1-3}$alkyl and halogen;

R$^6$ is selected form hydrogen, alkyl and substituted alkyl;

R$^7$ is selected form hydrogen, alkyl and substituted alkyl;

m is 0; and

AR is selected from naphthalene, phenyl, pyridine and pyrazole, and optionally substituted with from one to three substituents selected from the group consisting of: alkyl, substituted alkyl, C$_1$–C$_{12}$aryl, substituted C$_1$–C$_{12}$aryl, hydroxy, amino, —NR$^{11}$R$^{11}$, alkoxy and halogen, where R$^{11}$ is selected from the group consisting of: hydrogen, alkyl, cycloalkyl, C$_1$–C$_{12}$aryl, substituted alkyl, substituted cycloalkyl and substituted C$_1$–C$_{12}$aryl;

and pharmaceutically acceptable salts, hydrates, solvates and esters thereof.

4. The method of claim 1 wherein the compound administered is a compound selected from:
2-(3-[2'-Methylphenyl]-2-methoxyphenyl)-9-hydroxy-naphth[1,2-d]imidazole-5-sulfonic acid hydrochloride;
2-(3-[4'-Methylphenyl]-2-methoxyphenyl)-9-hydroxy-naphth[1,2-d]imidazole-5-sulfonic acid hydrochloride;

2-(3-[3',4'-Dimethylphenyl]-2-methoxyphenyl)-9-hydroxy-naphth[1,2-d]imidazole-5-sulfonic acid hydrochloride;
2-(3-[3'-Methoxyphenyl]-2-methoxyphenyl)-9-hydroxy-naphth[1,2-d]imidazole-5-sulfonic acid hydrochloride;
2-(3-[3'-Trifluoromethylphenyl]-2-methoxyphenyl)-9-hydroxy-naphth[1,2-d]imidazole-5-sulfonic acid hydrochloride;
2-(3-[4'-Fluorophenyl]-2-methoxyphenyl)-9-hydroxy-naphth[1,2-d]imidazole-5-sulfonic acid hydrochloride;
2-(3-[4'-Chlorophenyl]-2-methoxyphenyl)-9-hydroxy-naphth[1,2-d]imidazole-5-sulfonic acid hydrochloride;
2-(3-[1'-Dibenzofuranyl]-2-methoxyphenyl)-9-hydroxy-naphth[1,2-d]imidazole-5-sulfonic acid hydrochloride;
2-(3-[1'-Naphthalenyl]-2-methoxyphenyl)-9-hydroxy-naphth[1,2-d]imidazole-5-sulfonic acid hydrochloride;
2-(3-[3'-Chlorophenyl]-2-methoxyphenyl)-9-hydroxy-naphth[1,2-d]imidazole-5-sulfonic acid hydrochloride;
2-(3-[3'-Nitrophenyl]-2-methoxyphenyl)-9-hydroxy-naphth[1,2-d]imidazole-5-sulfonic acid hydrochloride;
2-(3-phenyl-2-methoxyphenyl)-9-hydroxy-naphth[1,2-d]imidazole-5-sulfonic acid hydrochloride;
2-(3-[2'-Methylphenyl]-2-methoxyphenyl)-9-hydroxy-naphth[1,2-d]imidazole-7-sulfonic acid hydrochloride;
2-(3-[4'-Methylphenyl]-2-methoxyphenyl)-9-hydroxy-naphth[1,2-d]imidazole-7-sulfonic acid hydrochloride;
2-(3-[3',4'-Dimethylphenyl]-2-methoxyphenyl)-9-hydroxy-naphth[1,2-d]imidazole-5-sulfonic acid hydrochloride;
2-(3-[3'-Methoxyphenyl]-2-methoxyphenyl)-9-hydroxy-naphth[1,2-d]imidazole-7-sulfonic acid hydrochloride;
2-(3-[3'-Trifluoromethylphenyl]-2-methoxyphenyl)-9-hydroxy-naphth[1,2-d]imidazole-7-sulfonic acid hydrochloride;
2-(3-[4'-Fluorophenyl]-2-methoxyphenyl)-9-hydroxy-naphth[1,2-d]imidazole-7-sulfonic acid hydrochloride;
2-(3-[4'-Chlorophenyl]-2-methoxyphenyl)-9-hydroxy-naphth[1,2-d]imidazole-7-sulfonic acid hydrochloride;
2-(3-[1'-Dibenzofuranyl]-2-methoxyphenyl)-9-hydroxy-naphth[1,2-d]imidazole-7-sulfonic acid hydrochloride;
2-(3-[1'-Naphthalenyl]-2-methoxyphenyl)-9-hydroxy-naphth[1,2-d]imidazole-7-sulfonic acid hydrochloride;
2-(3-[3'-Chlorophenyl]-2-methoxyphenyl)-9-hydroxy-naphth[1,2-d]imidazole-7-sulfonic acid hydrochloride;
2-(3-[3'-Nitrophenyl]-2-methoxyphenyl)-9-hydroxy-naphth[1,2-d]imidazole-7-sulfonic acid hydrochloride;
2-(3-phenyl-2-methoxyphenyl)-9-hydroxy-naphth[1,2-d]imidazole-7-sulfonic acid hydrochloride;
2-(4-[2'-Methylphenyl]-2-methoxyphenyl)-9-hydroxy-naphth[1,2-d]imidazole-5-sulfonic acid hydrochloride;
2-(4-[4'-Methylphenyl]-2-methoxyphenyl)-9-hydroxy-naphth[1,2-d]imidazole-5-sulfonic acid hydrochloride;
2-(4-[3',4'-Dimethylphenyl]-2-methoxyphenyl)-9-hydroxy-naphth[1,2-d]imidazole-5-sulfonic acid hydrochloride;
2-(4-[3'-Methoxyphenyl]-2-methoxyphenyl)-9-hydroxy-naphth[1,2-d]imidazole-5-sulfonic acid hydrochloride;
2-(4-[3'-Trifluoromethylphenyl]-2-methoxyphenyl)-9-hydroxy-naphth[1,2-d]imidazole-5-sulfonic acid hydrochloride;
2-(4-[4'-Fluorophenyl]-2-methoxyphenyl)-9-hydroxy-naphth[1,2-d]imidazole-5-sulfonic acid hydrochloride;
2-(4-[4'-Chlorophenyl]-2-methoxyphenyl)-9-hydroxy-naphth[1,2-d]imidazole-5-sulfonic acid hydrochloride;
2-(4-[1'-Dibenzofuranyl]-2-methoxyphenyl)-9-hydroxy-naphth[1,2-d]imidazole-5-sulfonic acid hydrochloride;
2-(4-[1'-Naphthalenyl]-2-methoxyphenyl)-9-hydroxy-naphth[1,2-d]imidazole-5-sulfonic acid hydrochloride;
2-(4-[3'-Chlorophenyl]-2-methoxyphenyl)-9-hydroxy-naphth[1,2-d]imidazole-5-sulfonic acid hydrochloride;
2-(4-[3'-Nitrophenyl]-2-methoxyphenyl)-9-hydroxy-naphth[1,2-d]imidazole-5-sulfonic acid hydrochloride;
2-(4-phenyl-2-methoxyphenyl)-9-hydroxy-naphth[1,2-d]imidazole-5-sulfonic acid hydrochloride;
2-(4-[2'-Methylphenyl]-2-methoxyphenyl)-9-hydroxy-naphth[1,2-d]imidazole-7-sulfonic acid hydrochloride;
2-(4-[4'-Methylphenyl]-2-methoxyphenyl)-9-hydroxy-naphth[1,2-d]imidazole-7-sulfonic acid hydrochloride;
2-(4-[3',4'-Dimethylphenyl]-2-methoxyphenyl)-9-hydroxy-naphth[1,2-d]imidazole-7-sulfonic acid hydrochloride;
2-(4-[3'-Methoxyphenyl]-2-methoxyphenyl)-9-hydroxy-naphth[1,2-d]imidazole-7-sulfonic acid hydrochloride;
2-(4-[3'-Trifluoromethylphenyl]-2-methoxyphenyl)-9-hydroxy-naphth[1,2-d]imidazole-7-sulfonic acid hydrochloride;
2-(4-[4'-Fluorophenyl]-2-methoxyphenyl)-9-hydroxy-naphth[1,2-d]imidazole-7-sulfonic acid hydrochloride;
2-(4-[4'-Chlorophenyl]-2-methoxyphenyl)-9-hydroxy-naphth[1,2-d]imidazole-7-sulfonic acid hydrochloride;
2-(4-[1'-Dibenzofuranyl]-2-methoxyphenyl)-9-hydroxy-naphth[1,2-d]imidazole-7-sulfonic acid hydrochloride;
2-(4-[1'-Naphthalenyl]-2-methoxyphenyl)-9-hydroxy-naphth[1,2-d]imidazole-7-sulfonic acid hydrochloride;
2-(4-[3'-Chlorophenyl]-2-methoxyphenyl)-9-hydroxy-naphth[1,2-d]imidazole-7-sulfonic acid hydrochloride;
2-(4-[3'-Nitrophenyl]-2-methoxyphenyl)-9-hydroxy-naphth[1,2-d]imidazole-7-sulfonic acid hydrochloride;
2-(4-phenyl-2-methoxyphenyl)-9-hydroxy-naphth[1,2-d]imidazole-7-sulfonic acid hydrochloride;
2-(3-[2'-Methylphenyl]-2-hydroxyphenyl)-9-hydroxy-naphth[1,2-d]imidazole-5-sulfonic acid hydrochloride;
2-(3-[4'-Methylphenyl]-2-hydroxyphenyl)-9-hydroxy-naphth[1,2-d]imidazole-5-sulfonic acid hydrochloride;
2-(3-[3',4'-Dimethylphenyl]-2-hydroxyphenyl)-9-hydroxy-naphth[1,2-d]imidazole-5-sulfonic acid hydrochloride;
2-(3-[3'-Trifluoromethylphenyl]-2-hydroxyphenyl)-9-hydroxy-naphth[1,2-d]imidazole-5-sulfonic acid hydrochloride;
2-(3-[4'-Fluorophenyl]-2-hydroxyphenyl)-9-hydroxy-naphth[1,2-d]imidazole-5-sulfonic acid hydrochloride;
2-(3-[4'-Chlorophenyl]-2-hydroxyphenyl)-9-hydroxy-naphth[1,2-d]imidazole-5-sulfonic acid hydrochloride;
2-(3-[1'-Dibenzofuranyl]-2-hydroxyphenyl)-9-hydroxy-naphth[1,2-d]imidazole-5-sulfonic acid hydrochloride;
2-(3-[1'-Naphthalenyl]-2-hydroxyphenyl)-9-hydroxy-naphth[1,2-d]imidazole-5-sulfonic acid hydrochloride;
2-(3-[3'-Chlorophenyl]-2-hydroxyphenyl)-9-hydroxy-naphth[1,2-d]imidazole-5-sulfonic acid hydrochloride;
2-(3-[3'-Nitrophenyl]-2-hydroxyphenyl)-9-hydroxy-naphth[1,2-d]imidazole-5-sulfonic acid hydrochloride;
2-(3-phenyl-2-hydroxyphenyl)-9-hydroxy-naphth[1,2-d]imidazole-5-sulfonic acid hydrochloride;

2-(3-[2'-Methylphenyl]-2-hydroxyphenyl)-9-hydroxy-naphth[1,2-d]imidazole-7-sulfonic acid hydrochloride;

2-(3-[4'-Methylphenyl]-2-hydroxyphenyl)-9-hydroxy-naphth[1,2-d]imidazole-7-sulfonic acid hydrochloride;

2-(3-[3',4'-Dimethylphenyl]-2-hydroxyphenyl)-9-hydroxy-naphth[1,2-d]imidazole-5-sulfonic acid hydrochloride;

2-(3-[3'-Trifluoromethylphenyl]-2-hydroxyphenyl)-9-hydroxy-naphth[1,2-d]imidazole-7-sulfonic acid hydrochloride;

2-(3-[4'-Fluorophenyl]-2-hydroxyphenyl)-9-hydroxy-naphth[1,2-d]imidazole-7-sulfonic acid hydrochloride;

2-(3-[4'-Chlorophenyl]-2-hydroxyphenyl)-9-hydroxy-naphth[1,2-d]imidazole-7-sulfonic acid hydrochloride;

2-(3-[1'-Dibenzofuranyl]-2-hydroxyphenyl)-9-hydroxy-naphth[1,2-d]imidazole-7-sulfonic acid hydrochloride;

2-(3-[1'-Naphthalenyl]-2-hydroxyphenyl)-9-hydroxy-naphth[1,2-d]imidazole-7-sulfonic acid hydrochloride;

2-(3-[3'-Chlorophenyl]-2-hydroxyphenyl)-9-hydroxy-naphth[1,2-d]imidazole-7-sulfonic acid hydrochloride;

2-(3-[3'-Nitrophenyl]-2-hydroxyphenyl)-9-hydroxy-naphth[1,2-d]imidazole-7-sulfonic acid hydrochloride;

2-(3-phenyl-2-hydroxyphenyl)-9-hydroxy-naphth[1,2-d]imidazole-7-sulfonic acid hydrochloride;

2-(4-[2'-Methylphenyl]-2-hydroxyphenyl)-9-hydroxy-naphth[1,2-d]imidazole-5-sulfonic acid hydrochloride;

2-(4-[4'-Methylphenyl]-2-hydroxyphenyl)-9-hydroxy-naphth[1,2-d]imidazole-5-sulfonic acid hydrochloride;

2-(4-[3'-Hydroxyphenyl]-2-hydroxyphenyl)-9-hydroxy-naphth[1,2-d]imidazole-5-sulfonic acid hydrochloride;

2-(4-[4'-Fluorophenyl]-2-hydroxyphenyl)-9-hydroxy-naphth[1,2-d]imidazole-5-sulfonic acid hydrochloride;

2-(4-[4'-Chlorophenyl]-2-hydroxyphenyl)-9-hydroxy-naphth[1,2-d]imidazole-5-sulfonic acid hydrochloride;

2-(4-[1'-Dibenzofuranyl]-2-hydroxyphenyl)-9-hydroxy-naphth[1,2-d]imidazole-5-sulfonic acid hydrochloride;

2-(4-[1'-Naphthalenyl]-2-hydroxyphenyl)-9-hydroxy-naphth[1,2-d]imidazole-5-sulfonic acid hydrochloride;

2-(4-[3'-Chlorophenyl]-2-hydroxyphenyl)-9-hydroxy-naphth[1,2-d]imidazole-5-sulfonic acid hydrochloride;

2-(4-[3'-Nitrophenyl]-2-hydroxyphenyl)-9-hydroxy-naphth[1,2-d]imidazole-5-sulfonic acid hydrochloride;

2-(4-phenyl-2-hydroxyphenyl)-9-hydroxy-naphth[1,2-d]imidazole-5-sulfonic acid hydrochloride;

2-(4-[2'-Methylphenyl]-2-hydroxyphenyl)-9-hydroxy-naphth[1,2-d]imidazole-7-sulfonic acid hydrochloride;

2-(4-[4'-Methylphenyl]-2-hydroxyphenyl)-9-hydroxy-naphth[1,2-d]imidazole-7-sulfonic acid hydrochloride;

2-(4-[3'-Hydroxyphenyl]-2-hydroxyphenyl)-9-hydroxy-naphth[1,2-d]imidazole-7-sulfonic acid hydrochloride;

2-(4-[4'-Fluorophenyl]-2-hydroxyphenyl)-9-hydroxy-naphth[1,2-d]imidazole-7-sulfonic acid hydrochloride;

2-(4-[4'-Chlorophenyl]-2-hydroxyphenyl)-9-hydroxy-naphth[1,2-d]imidazole-7-sulfonic acid hydrochloride;

2-(4-[1'-Dibenzofuranyl]-2-hydroxyphenyl)-9-hydroxy-naphth[1,2-d]imidazole-7-sulfonic acid hydrochloride;

2-(4-[1'-Naphthalenyl]-2-hydroxyphenyl)-9-hydroxy-naphth[1,2-d]imidazole-7-sulfonic acid hydrochloride;

2-(4-[3'-Chlorophenyl]-2-hydroxyphenyl)-9-hydroxy-naphth[1,2-d]imidazole-7-sulfonic acid hydrochloride;

2-(4-[3'-Nitrophenyl]-2-hydroxyphenyl)-9-hydroxy-naphth[1,2-d]imidazole-7-sulfonic acid hydrochloride;

2-(4-phenyl-2-hydroxyphenyl)-9-hydroxy-naphth[1,2-d]imidazole-7-sulfonic acid hydrochloride;

2-(3-phenyl-2-methoxyphenyl)-9-hydroxy-naphth[1,2-d]imidazole-7-carboxylic acid hydrochloride;

2-(3-[3',4'-dimethylphenyl]-2-methoxyphenyl)-9-hydroxy-naphth[1,2-d]imidazole-7-carboxylic acid trifluoroacetate;

2-(3-[3',4'-dimethylphenyl]-2-hydroxyphenyl)-9-hydroxy-naphth[1,2-d]imidazole-7-carboxylic acid trifluoroacetate;

2-(1-[3,4-dimethylphenyl]-3-methyl-5-hydroxy-1H-pyrrazole-4-yl)-9-hydroxy-3H-naphth[1,2-d]imidazole-7-carboxylic acid trifluoroacetate;

2-(1-hydroxy-2-naphthalenyl)-9-hydroxy-naphth[1,2-d]imidazole-7-carboxylic acid trifluoroacetate;

2-(2-pyridinyl)-9-hydroxy-naphth[1,2-d]imidazole-7-carboxylic acid trifluoroacetate;

2-(3',4'-dimethylbiphenyl-3-yl)-9-hydroxy-3H-naphtho[1,2-d]imidazole-7-sulfonic acid hydrochloride;

2-biphenyl-4-yl-9-hydroxy-3H-naphtho[1,2-d]imidazole-7-sulfonic acid hydrochloride;

2-(3',4'-dimethylbiphenyl-4-yl)-9-hydroxy-3H-naphtho[1,2-d]imidazole-7-sulfonic acid trifluoroacetate;

2-(4'-tert-butylbiphenyl-3-yl)-9-hydroxy-3H-naphtho[1,2-d]imidizole-7-sulfonic acid trifuoroacetate;

2-[3-(4-tert-butylbenzyloxy)-phenyl]-9-hydroxy-3H-naphtho[1,2-d]imidizole-7-sulfonic acid hydrochloride;

2-[3-(3-trifluoromethylbenzyloxy)-phenyl]-9-hydroxy-3H-naphtho[1,2-d]imidizole-7-sulfonic acid hydrochloride;

2-[3-(3,4-dimethylbenzyloxy)-phenyl]-9-hydroxy-3H-naphtho[1,2-d]imidizole-7-sulfonic acid hydrochloride;

2-(3',4'-dimethylbiphenyl-3-yl)-9-hydroxy-3H-naphtho[1,2-d]imidazole-7-carboxylic acid hydrochloride;

2-(3',4'-dimethylbiphenyl-4-yl)-9-hydroxy-3H-naphtho[1,2-d]imidazole-7-carboxylic acid trifluoroacetate;

2-(4'-tert-butylbiphenyl-3-yl)-9-hydroxy-3H-naphtho[1,2-d]imidazole-7-carboxylic acid trifluoroacetate;

9-hydroxy-2-(3-phenoxyphenyl)-3H-naphtho[1,2-d]imidazole-7-carboxylic acid trifluoroacetate;

3-[2-(3',4'-dimethylbiphenyl-3-yl)-9-hydroxy-3H-naphtho[1,2-d]imidazole-7-sulfonylamino]-benzoic acid;

1-[2-(3',4'-dimethylbiphenyl-3-yl)-9-hydroxy-3H-naphtho[1,2-d]imidazole-7-sulfonyl]-piperidine-3-carboxylic acid;

(S)-1-[2-(3',4'-dimethyl-biphenyl-3-yl)-9-hydroxy-3H-naphtho[1,2-d]imidazole-7-sulfonyl]-pyrrolidine-2-carboxylic acid;

({1-[2-(3',4'-dimethylbiphenyl-3-yl)-9-hydroxy-3H-naphtho[1,2-d]imidazol-7-yl]-methanoyl}-amino)-acetic acid;

(S)-2-({1-[2-(3',4'-dimethylbiphenyl-3-yl)-9-hydroxyl-3H-naphtho[1,2-d]imidazol-7-yl]-methanoyl}-amino)-propionic acid;

({1-[2-(3',4'-dimethylbiphenyl-3-yl)-9-hydroxyl-3H-naphtho[1,2-d]imidazol-7-yl]-methanoyl}-methylamino)-acetic acid;

(S)-1-{1-[2-(3',4'-dimethylbiphenyl-3-yl)-9-hydroxyl-3H-naphtho[1,2-d]imidazol-7-yl]-methanoyl}-pyrrolidine-2-carboxylic acid;

(S)-2-({1-[2-(4' tert-butyllbiphenyl-3-yl)-9-hydroxy-3H-naphtho[1,2-d]imidazol-7-yl]-methanoyl}-amino)-pentanedioic acid;

2-[6-(4-tert-butylphenyl)-pyridin-2-yl]-9-hydroxy-3H-naphtho[1,2-d]imidazole-7-carboxylic acid;

2-[5-(3,4-dichlorophenyl)furan-2-yl]-9-hydroxy-3H-naphtho[1,2-d]imidazole-7-carboxylic acid;

2-[5-benzo[b]thiophen-2-yl-furan-2-yl]-9-hydroxy-3H-naphtho[1,2-d]imidazole-7-carboxylic acid;

9-Hydroxy-2-[5-(4-tert-butylphenyl)-furan-2-yl]-3H-naphtho[1,2-d]imidazole-7-carboxylic acid;

9-Hydroxy-2-[4-(4-tert-butylphenyl)-furan-2-yl]-3H-naphtho[1,2-d]imidazole-7-carboxylic acid;

2-[5-(3,4-dimethylphenyl)-furan-2-yl]-9-hydroxy-3H-naphtho[1,2-d]imidazole-7-carboxylic acid;

2-[4-(3,4-dimethylphenyl)-furan-2-yl]-9-hydroxy-3H-naphtho[1,2-d]imidazole-7-carboxylic acid;

2-[5-(4-tert-butylphenyl)-thiophen-2-yl]-9-hydroxy-3H-naphtho[1,2-d]imidazole-7-carboxylic acid;

2-[4-(4-tert-butylphenyl)-thiophen-2-yl]-4-hydroxy-3H-naphtho[1,2-d]imidazole-7-carboxylic acid;

2-[5-(3,4-dimethylphenyl)-thiophen-2-yl]-9-hydroxy-3H-naphtho[1,2-d]imidazole-7-carboxylic acid;

2-[4-(3,4-dimethylphenyl)-thiophen-2-yl]-9-hydroxy-3H-naphtho[1,2-d]imidazole-7-carboxylic acid;

2-[4'-tert-butyl-6-methoxybiphenyl-3-yl]-9-hydroxy-3H-naphtho[1,2-d]imidazole-7-carboxylic acid;

2-[4'-tert-butyl-6-fluoro-biphenyl-3-yl]-9-hydroxy-3H-naphtho[1,2-d]imidazole-7-carboxylic acid;

2-[4'-tert-butyl-4-fluorobiphenyl-3-yl]-9-hydroxy-3H-naphtho[1,2-d]imidazole-7-carboxylic acid;

2-[6-fluoro-3',4'-dimethylbiphenyl-3-yl]-9-hydroxy-3H-naphtho[1,2-d]imidazole-7-carboxylic acid;

2-[4-fluoro-3',4'-dimethylbiphenyl-3-yl]-9-hydroxy-3H-naphtho[1,2-d]imidazole-7-carboxylic acid;

2-[4'-trifluoromethylbiphenyl-3-yl]-9-hydroxy-3H-naphtho[1,2-d]imidazole-7-carboxylic acid;

9-Hydroxy-2-[5-(3-isopropylphenyl)-furan-2-yl]-3H-naphtho[1,2-d]imidazole-7-carboxylic acid;

9-Hydroxy-2-[4-(4-tert-butylphenyl)-furan-2-yl]-3H-naphtho[1,2-d]imidazole-7-carboxylic acid;

9-Hydroxy-2-[5-(4-tert-butylphenyl)-furan-2-yl]-3H-naphtho[1,2-d]imidazole-7-carboxylic acid;

2-[5-(3,4-dimethylphenyl)-thiophen-2-yl]-9-hydroxy-3H-naphtho[1,2-d]imidazole-7-carboxylic acid;

2-[4-(3,4-dimethylphenyl)-thiophen-2-yl]-9-hydroxy-3H-naphtho[1,2-d]imidazole-7-carboxylic acid;

2-[4-(4-tert-butylphenyl)-thiophen-2-yl]-9-hydroxy-3H-naphtho[1,2-d]imidazole-7-carboxylic acid;

2-[5-(4-tert-butylphenyl)-thiophen-2-yl]-9-hydroxy-3H-naphtho[1,2-d]imidazole-7-carboxylic acid;

2-[5-(3,4-dichlorophenyl)furan-2-yl]-9-hydroxy-3H-naphtho[1,2-d]imidazole-7-carboxylic acid;

2-[5-benzo[b]thiophen-2-yl-furan-2-yl]-9-hydroxy-3H-naphtho[1,2-d]imidazole-7-carboxylic acid;

2-[4'-tert-butyl-6-methoxybiphenyl-3-yl]-9-hydroxy-3H-naphtho[1,2-d]imidazole-7-carboxylic acid;

2-[6-fluoro-3',4'-dimethylbiphenyl-3-yl]-9-hydroxy-3H-naphtho[1,2-d]imidazole-7-carboxylic acid;

2-[4-fluoro-3',4'-dimethylbiphenyl-3-yl]-9-hydroxy-3H-naphtho[1,2-d]imidazole-7-carboxylic acid;

2-[4'-tert-butyl-4-fluorobiphenyl-3-yl]-9-hydroxy-3H-naphtho[1,2-d]imidazole-7-carboxylic acid;

2-[4'-trifluoromethylbiphenyl-3-yl]-9-hydroxy-3H-naphtho[1,2-d]imidazole-7-carboxylic acid;

2-[4'-tert-butyl-6-fluoro-biphenyl-3-yl]-9-hydroxy-3H-naphtho[1,2-d]imidazole-7-carboxylic acid;

2-[5-(4-tert-butylphenyl)-pyridin-3-yl]-9-hydroxy-1H-naphtho[1,2-d]imidazole-7-carboxylic acid;

2-[(2-fluoro-4-trifluoromethylbiphenyl)-3-yl]-9-hydroxy-1H-naphtho[1,2-d]imidazole-7-carboxylic acid;

2-[(2,5-difluoro-4-trifluoromethylbiphenyl)-3-yl]-9-hydroxy-1H-naphtho[1,2-d]imidazole-7-carboxylic acid;

2-[(4-fluoro-4'-trifluoromethylbiphenyl)-3-yl]-9-hydroxy-1H-naphtho[1,2-d]imidazole-7-carboxylic acid;

2-[5-(4-trifluoromethylphenyl)-furan-2-yl]-9-hydroxy-3H-naphtho[1,2-d]imidazole-7-carboxylic acid;

2-[4-(4-trifluoromethylphenyl)-thiophen-2-yl]-9-hydroxy-3H-naphtho[1,2-d]imidazole-7-carboxylic acid;

2-(4'-ethylbiphenyl-3-yl)-9-hydroxy-3H-naphtho[1,2-d]imidazole-7-carboxylic acid;

2-(4'-propylbiphenyl-3-yl)-9-hydroxy-3H-naphtho[1,2-d]imidazole-7-carboxylic acid;

2-(4'-butylbiphenyl-3-yl)-9-hydroxy-3H-naphtho[1,2-d]imidazole-7-carboxylic acid;

2-(4'-carboxy-3'-methylbiphenyl-3-yl)-9-hydroxy-3H-naphtho[1,2-d]imidazole-7-carboxylic acid;

2-(4'-cyano-3'-methylbiphenyl-3-yl)-9-hydroxy-3H-naphtho[1,2-d]imidazole-7-carboxylic acid;

2-(4'-fluoro-3'-methylbiphenyl-3-yl)-9-hydroxy-3H-naphtho[1,2-d]imidazole-7-carboxylic acid;

2-[1-(4-tert-butylphenyl)-1H-pyrazol-4-yl]-9-hydroxy-3H-naphtho[1,2-d]imidazole-7-carboxylic acid;

2-(3',4'-difluorobiphenyl-3-yl)-9-hydroxy-3H-naphtho[1,2-d]imidazole-7-carboxylic acid; and 2-[3-(9H-fluoren-2-yl)-phenyl]-9-hydroxy-3H-naphtho[1,2-d]imidazole-7-carboxylic acid, and pharmaceutically acceptable salts, hydrates, solvates and esters thereof.

5. The method of claim 1 wherein the mammal is a human.

6. A method of enhancing platelet production in a mammal in need thereof which comprises administering to such mammal a therapeutically effective among of a compound of Formula (I):

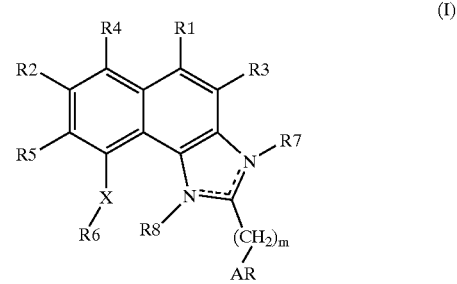

wherein:
the C ring has one double bond where indicated by the broken lines, provided that $R^8$ is absent when the nitrogen attached thereto has a double bond and provided that $R^7$ is absent when the nitrogen attached thereto has a double bond;

R¹, R², R³, R⁴ and R⁵ are each independently selected from the group consisting of: hydrogen, —C(O)OR¹¹, —CONR⁹R¹⁰, —SO₂NR⁹R¹⁰, phosphonic acid, phosphinic acid, C₁₋₆alkyl, C₁₋₆alkoxy, —(CH₂)ₚOR¹¹, nitro, cyano, halogen, —NR⁹R¹⁰, N-acylamino, N-sulfonylamino, —S(O)ₙR¹¹, aryl, substituted aryl, alkyl, cycloalkyl, substituted cycloalkyl, protected —OH, and alkyl substituted with one or more substituents selected from the group consisting of: alkoxy, acyloxy, aryl, substituted aryl, —NR⁹R¹⁰, N-acylamino, oxo, hydroxy, cycloalkyl, substituted cycloalkyl, —C(O)OR¹¹, —C(O)NR⁹R¹⁰, —S(O)₂NR⁹R¹⁰, —S(O)ₙR¹¹, aryloxy, nitro, cyano, halogen, and protected —OH;

where n is 0 to 3;

p is 0 to 6;

R¹¹ is selected from the group consisting of: hydrogen, alkyl, cycloalkyl, C₁–C₁₂aryl, substituted alkyl, substituted cycloalkyl and substituted C₁–C₁₂aryl; and R⁹ and R¹⁰ are independently selected from hydrogen, cycloalkyl, C₁–C₁₂aryl, substituted cycloalkyl, substituted C₁–C₁₂aryl, alkyl or alkyl substituted with one or more substituents selected from the group consisting of: alkoxy, acyloxy, aryloxy, —NR¹¹R¹¹, N-acylamino, oxo, hydroxy, —C(O)OR¹¹, —S(O)ₙR¹¹, —C(O)NR¹¹R¹¹, —S(O)₂NR¹¹R¹¹, nitro, cyano, halogen, cycloalkyl, substituted cycloalkyl, aryl, substituted aryl and protected —OH where n and R¹¹ are as described above; or R⁹ and R¹⁰ taken together with the nitrogen to which they are attached represent a 5 to 6 member saturated ring containing up to one other heteroatom selected from oxygen and nitrogen;

R⁶ is selected from the group consisting of: hydrogen, alkyl, cycloalkyl, C₁–C₁₂aryl, substituted alkyl, substituted cycloalkyl and substituted C₁–C₁₂aryl;

R⁷ is absent when the nitrogen attached thereto has a double bond or selected from the group consisting of: hydrogen, alkyl, cycloalkyl, C₁–C₁₂aryl, substituted alkyl, substituted cycloalkyl and substituted C₁–C₁₂aryl;

R⁸ is absent when the nitrogen attached thereto has a double bond or selected from the group consisting of: hydrogen, alkyl, cycloalkyl, C₁–C₁₂aryl, substituted alkyl, substituted cycloalkyl and substituted C₁–C₁₂aryl;

m is 0–6;

X is selected from the group consisting of sulfur, sulfonamido, oxygen and an amino group which may be substituted by C₁–C₁₀alkyl or benzyl;

AR is a cyclic or polycyclic aromatic ring containing from 3 to 16 carbon atoms, optionally containing one or more heteroatoms, provided that when the number of carbon atoms is 3 the aromatic ring contains at least two heteroatoms and when the number of carbon atoms is 4 the aromatic ring at least one heteroatom, optionally substituted with one or more substituents selected from the group consisting of: alkyl, substituted alkyl, cycloalkyl, substituted cycloalkyl, aryl, substituted aryl, aryloxy, hydroxy, alkoxy, acyloxy, —NR¹²R¹³, N-acylamino, N-sulfonylamino, nitro, cyano, halogen, —C(O)OR¹¹, —C(O)NR¹²R¹³, —S(O)₂NR¹²R¹³, —S(O)ₙR¹¹, protected —OH, and alkyl substituted with one or more substituents selected from the group consisting of: alkoxy, acyloxy, aryl, substituted aryl, amino, N-acylamino, oxo, hydroxy, cycloalkyl, substituted cycloalkyl, —C(O)OR¹¹, —S(O)₂NR¹²R¹³, —S(O)ₙR¹¹, aryloxy, nitro, cyano, halogen, and protected —OH, where n is 0 to 3;

R¹¹ is selected from the group consisting of: hydrogen, alkyl, cycloalkyl, C₁–C₁₂aryl, substituted alkyl, substituted cycloalkyl and substituted C₁–C₁₂aryl, and R¹² and R¹³ are independently selected from the group consisting of: hydrogen, cycloalkyl, C₆–C₁₂aryl, substituted cycloalkyl, substituted C₆–C₁₂aryl, alkyl or alkyl substituted with one or more substituents selected from the group consisting of: alkoxy, acyloxy, aryloxy, —NR¹¹R¹¹, N-acylamino, oxo, hydroxy, —C(O)OR¹¹, —S(O)ₙR¹¹, —C(O)NR¹¹R¹¹, —S(O)₂NR¹¹R¹¹, nitro, cyano, cycloalkyl, substituted cycloalkyl, halogen, C₁–C₁₂aryl, substituted C₁–C₁₂aryl and protected —OH, where n and R¹¹ are as described above; and pharmaceutically acceptable salts, hydrates, solvates and esters thereof.

7. The method of claim 6 wherein the mammal is a human.

8. The method of claim 1 wherein the compound is administered orally.

9. The method of claim 1 wherein the compound is administered parenterally.

10. A method of agonizing the TPO receptor in a mammal in need thereof which comprises administering to such mammal a therapeutically effective amount of a compound of Formula (I):

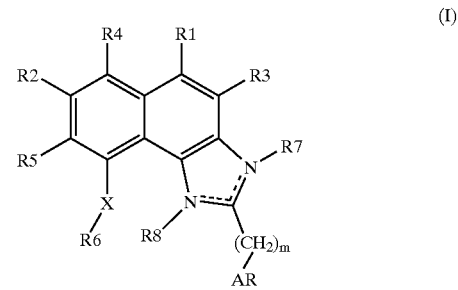

(I)

wherein:

the C ring has one double bond where indicated by the broken lines, provided that R⁸ is absent when the nitrogen attached thereto has a double bond and provided that R⁷ is absent when the nitrogen attached thereto has a double bond;

R¹, R², R³, R⁴ and R⁵ are each independently selected from the group consisting of: hydrogen, —C(O)OR¹¹, —CONR⁹R¹⁰, —SO₂NR⁹R¹⁰, phosphonic acid, phosphinic acid, C₁₋₆alkyl, C₁₋₆alkoxy, —(CH₂)ₚOR¹¹, nitro, cyano, halogen, —NR⁹R¹⁰, N-acylamino, N-sulfonylamino, —S(O)ₙR¹¹, aryl, substituted aryl, alkyl, cycloalkyl, substituted cycloalkyl, protected —OH, and alkyl substituted with one or more substituents selected from the group consisting of: alkoxy, acyloxy, aryl, substituted aryl, —NR⁹R¹⁰, N-acylamino, oxo, hydroxy, cycloalkyl, substituted cycloalkyl, —C(O)OR¹¹, —C(O)NR⁹R¹⁰, —S(O)₂NR⁹R¹⁰, —S(O)ₙR¹¹, aryloxy, nitro, cyano, halogen, and protected —OH;

where n is 0 to 3;

p is 0 to 6;

$R^{11}$ is selected from the group consisting of: hydrogen, alkyl, cycloalkyl, $C_1$–$C_{12}$aryl, substituted alkyl, substituted cycloalkyl and substituted $C_1$–$C_{12}$aryl; and $R^9$ and $R^{10}$ are independently selected from hydrogen, cycloalkyl, $C_1$–$C_{12}$aryl, substituted cycloalkyl, substituted $C_1$–$C_{12}$aryl, alkyl or alkyl substituted with one or more substituents selected from the group consisting of: alkoxy, acyloxy, aryloxy, —$NR^{11}R^{11}$, N-acylamino, oxo, hydroxy, —$C(O)OR^{11}$, —$S(O)_nR^{11}$, —$C(O)NR^{11}R^{11}$, —$S(O)_2NR^{11}R^{11}$, nitro, cyano, halogen, cycloalkyl, substituted cycloalkyl, aryl, substituted aryl and protected —OH where n and $R^{11}$ are as described above; or $R^9$ and $R^{10}$ taken together with the nitrogen to which they are attached represent a 5 to 6 member saturated ring containing up to one other heteroatom selected from oxygen and nitrogen;

$R^6$ is selected from the group consisting of: hydrogen, alkyl, cycloalkyl, $C_1$–$C_{12}$aryl, substituted alkyl, substituted cycloalkyl and substituted $C_1$–$C_{12}$aryl;

$R^7$ is absent when the nitrogen attached thereto has a double bond or selected from the group consisting of: hydrogen, alkyl, cycloalkyl, $C_1$–$C_{12}$aryl, substituted alkyl, substituted cycloalkyl and substituted $C_1$–$C_{12}$aryl;

$R^8$ is absent when the nitrogen attached thereto has a double bond or selected from the group consisting of: hydrogen, alkyl, cycloalkyl, $C_1$–$C_{12}$aryl, substituted alkyl, substituted cycloalkyl and substituted $C_1$–$C_{12}$aryl;

m is 0–6;

X is selected from the group consisting of sulfur, sulfonamido, oxygen and an amino group which may be substituted by $C_1$–$C_{10}$alkyl or benzyl;

AR is a cyclic or polycyclic aromatic ring containing from 3 to 16 carbon atoms, optionally containing one or more heteroatoms, provided that when the number of carbon atoms is 3 the aromatic ring contains at least two heteroatoms and when the number of carbon atoms is 4 the aromatic ring at least one heteroatom, optionally substituted with one or more substituents selected from the group consisting of: alkyl, substituted alkyl, cycloalkyl, substituted cycloalkyl, aryl, substituted aryl, aryloxy, hydroxy, alkoxy, acyloxy, —$NR^{12}R^{13}$, N-acylamino, N-sulfonylamino, nitro, cyano, halogen, —$C(O)OR^{11}$, —$C(O)NR^{12}R^{13}$, —$S(O)_2NR^{12}R^{13}$, —$S(O)_nR^{11}$, protected —OH, and alkyl substituted with one or more substituents selected from the group consisting of: alkoxy, acyloxy, aryl, substituted aryl, amino, N-acylamino, oxo, hydroxy, cycloalkyl, substituted cycloalkyl, —$C(O)OR^{11}$, —$S(O)_2NR^{12}R^{13}$, —$S(O)_nR^{11}$, aryloxy, nitro, cyano, halogen, and protected —OH, where n is 0 to 3;

$R^{11}$ is selected from the group consisting of: hydrogen, alkyl, cycloalkyl, $C_1$–$C_{12}$aryl, substituted alkyl, substituted cycloalkyl and substituted $C_1$–$C_{12}$aryl, and $R^{12}$ and $R^{13}$ are independently selected from the group consisting of: hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, —$NR^{11}R^{11}$, N-acylamino, oxo, hydroxy, —$C(O)OR^{11}$, —$S(O)_nR^{11}$, —$C(O)NR^{11}R^{11}$, —$S(O)_2NR^{11}R^{11}$, nitro, cyano, cycloalkyl, substituted cycloalkyl, halogen, $C_1$–$C_{12}$aryl, substituted $C_1$–$C_{12}$aryl and protected —OH, where n and $R^{11}$ are as described above; and pharmaceutically acceptable salts, hydrates, solvates and esters thereof.

11. The method of claim 10 wherein the mammal is a human.

12. A compound selected from:

2-(3-[2'-Methylphenyl]-2-methoxyphenyl)-9-hydroxy-naphth[1,2-d]imidazole-5-sulfonic acid hydrochloride;

2-(3-[4'-Methylphenyl]-2-methoxyphenyl)-9-hydroxy-naphth[1,2-d]imidazole-5-sulfonic acid hydrochloride;

2-(3-[3',4'-Dimethylphenyl]-2-methoxyphenyl)-9-hydroxy-naphth[1,2-d]imidazole-5-sulfonic acid hydrochloride;

2-(3-[3'-Methoxyphenyl]-2-methoxyphenyl)-9-hydroxy-naphth[1,2-d]imidazole-5-sulfonic acid hydrochloride;

2-(3-[3'-Trifluoromethylphenyl]-2-methoxyphenyl)-9-hydroxy-naphth[1,2-d]imidazole-5-sulfonic acid hydrochloride;

2-(3-[4'-Fluorophenyl]-2-methoxyphenyl)-9-hydroxy-naphth[1,2-d]imidazole-5-sulfonic acid hydrochloride;

2-(3-[4'-Chlorophenyl]-2-methoxyphenyl)-9-hydroxy-naphth[1,2-d]imidazole-5-sulfonic acid hydrochloride;

2-(3-[1'-Dibenzofuranyl]-2-methoxyphenyl)-9-hydroxy-naphth[1,2-d]imidazole-5-sulfonic acid hydrochloride;

2-(3-[1'-Naphthalenyl]-2-methoxyphenyl)-9-hydroxy-naphth[1,2-d]imidazole-5-sulfonic acid hydrochloride;

2-(3-[3'-Chlorophenyl]-2-methoxyphenyl)-9-hydroxy-naphth[1,2-d]imidazole-5-sulfonic acid hydrochloride;

2-(3-[3'-Nitrophenyl]-2-methoxyphenyl)-9-hydroxy-naphth[1,2-d]imidazole-5-sulfonic acid hydrochloride;

2-(3-phenyl-2-methoxyphenyl)-9-hydroxy-naphth[1,2-d]imidazole-5-sulfonic acid hydrochloride;

2-(3-[2'-Methylphenyl]-2-methoxyphenyl)-9-hydroxy-naphth[1,2-d]imidazole-7-sulfonic acid hydrochloride;

2-(3-[4'-Methylphenyl]-2-methoxyphenyl)-9-hydroxy-naphth[1,2-d]imidazole-7-sulfonic acid hydrochloride;

2-(3-[3',4'-Dimethylphenyl]-2-methoxyphenyl)-9-hydroxy-naphth[1,2-d]imidazole-5-sulfonic acid hydrochloride;

2-(3-[3'-Methoxyphenyl]-2-methoxyphenyl)-9-hydroxy-naphth[1,2-d]imidazole-7-sulfonic acid hydrochloride;

2-(3-[3'-Trifluoromethylphenyl]-2-methoxyphenyl)-9-hydroxy-naphth[1,2-d]imidazole-7-sulfonic acid hydrochloride;

2-(3-[4'-Fluorophenyl]-2-methoxyphenyl)-9-hydroxy-naphth[1,2-d]imidazole-7-sulfonic acid hydrochloride;

2-(3-[4'-Chlorophenyl]-2-methoxyphenyl)-9-hydroxy-naphth[1,2-d]imidazole-7-sulfonic acid hydrochloride;

2-(3-[1'-Dibenzofuranyl]-2-methoxyphenyl)-9-hydroxy-naphth[1,2-d]imidazole-7-sulfonic acid hydrochloride;

2-(3-[1'-Naphthalenyl]-2-methoxyphenyl)-9-hydroxy-naphth[1,2-d]imidazole-7-sulfonic acid hydrochloride;

2-(3-[3'-Chlorophenyl]-2-methoxyphenyl)-9-hydroxy-naphth[1,2-d]imidazole-7-sulfonic acid hydrochloride;

2-(3-[3'-Nitrophenyl]-2-methoxyphenyl)-9-hydroxy-naphth[1,2-d]imidazole-7-sulfonic acid hydrochloride;

2-(3-phenyl-2-methoxyphenyl)-9-hydroxy-naphth[1,2-d]imidazole-7-sulfonic acid hydrochloride;

2-(4-[2'-Methylphenyl]-2-methoxyphenyl)-9-hydroxy-naphth[1,2-d]imidazole-5-sulfonic acid hydrochloride;

2-(4-[4'-Methylphenyl]-2-methoxyphenyl)-9-hydroxy-naphth[1,2-d]imidazole-5-sulfonic acid hydrochloride;
2-(4-[3',4'-Dimethylphenyl]-2-methoxyphenyl)-9-hydroxy-naphth[1,2-d]imidazole-5-sulfonic acid hydrochloride;
2-(4-[3'-Methoxyphenyl]-2-methoxyphenyl)-9-hydroxy-naphth[1,2-d]imidazole-5-sulfonic acid hydrochloride;
2-(4-[3'-Trifluoromethylphenyl]-2-methoxyphenyl)-9-hydroxy-naphth[1,2-d]imidazole-5-sulfonic acid hydrochloride;
2-(4-[4'-Fluorophenyl]-2-methoxyphenyl)-9-hydroxy-naphth[,2-d]imidazole-5-sulfonic acid hydrochloride;
2-(4-[4'-Chlorophenyl]-2-methoxyphenyl)-9-hydroxy-naphth[1,2-d]imidazole-5-sulfonic acid hydrochloride;
2-(4-[1'-Dibenzofuranyl]-2-methoxyphenyl)-9-hydroxy-naphth[1,2-d]imidazole-5-sulfonic acid hydrochloride;
2-(4-[1'-Naphthalenyl]-2-methoxyphenyl)-9-hydroxy-naphth[1,2-d]imidazole-5-sulfonic acid hydrochloride;
2-(4-[3'-Chlorophenyl]-2-methoxyphenyl)-9-hydroxy-naphth[1,2-d]imidazole-5-sulfonic acid hydrochloride;
2-(4-[3'-Nitrophenyl]-2-methoxyphenyl)-9-hydroxy-naphth[1,2-d]imidazole-5-sulfonic acid hydrochloride;
2-(4-phenyl-2-methoxyphenyl)-9-hydroxy-naphth[1,2-d]imidazole-5-sulfonic acid hydrochloride;
2-(4-[2'-Methylphenyl]-2-methoxyphenyl)-9-hydroxy-naphth[1,2-d]imidazole-7-sulfonic acid hydrochloride;
2-(4-[4'-Methylphenyl]-2-methoxyphenyl)-9-hydroxy-naphth[1,2-d]imidazole-7-sulfonic acid hydrochloride;
2-(4-[3',4'-Dimethylphenyl]-2-methoxyphenyl)-9-hydroxy-naphth[1,2-d]imidazole-7-sulfonic acid hydrochloride;
2-(4-[3'-Methoxyphenyl]-2-methoxyphenyl)-9-hydroxy-naphth[1,2-d]imidazole-7-sulfonic acid hydrochloride;
2-(4-[3'-Trifluoromethylphenyl]-2-methoxyphenyl)-9-hydroxy-naphth[1,2-d]imidazole-7-sulfonic acid hydrochloride;
2-(4-[4'-Fluorophenyl]-2-methoxyphenyl)-9-hydroxy-naphth[1,2-d]imidazole-7-sulfonic acid hydrochloride;
2-(4-[4'-Chlorophenyl]-2-methoxyphenyl)-9-hydroxy-naphth[1,2-d]imidazole-7-sulfonic acid hydrochloride;
2-(4-[1'-Dibenzofuranyl]-2-methoxyphenyl)-9-hydroxy-naphth[1,2-d]imidazole-7-sulfonic acid hydrochloride;
2-(4-[1'-Naphthalenyl]-2-methoxyphenyl)-9-hydroxy-naphth[1,2-d]imidazole-7-sulfonic acid hydrochloride;
2-(4-[3'-Chlorophenyl]-2-methoxyphenyl)-9-hydroxy-naphth[1,2-d]imidazole-7-sulfonic acid hydrochloride;
2-(4-[3'-Nitrophenyl]-2-methoxyphenyl)-9-hydroxy-naphth[1,2-d]imidazole-7-sulfonic acid hydrochloride;
2-(4-phenyl-2-methoxyphenyl)-9-hydroxy-naphth[1,2-d]imidazole-7-sulfonic acid hydrochloride;
2-(3-[2'-Methylphenyl]-2-hydroxyphenyl)-9-hydroxy-naphth[1,2-d]imidazole-5-sulfonic acid hydrochloride;
2-(3-[4'-Methylphenyl]-2-hydroxyphenyl)-9-hydroxy-naphth[1,2-d]imidazole-5-sulfonic acid hydrochloride;
2-(3-[3',4'-Dimethylphenyl]-2-hydroxyphenyl)-9-hydroxy-naphth[1,2-d]imidazole-5-sulfonic acid hydrochloride;
2-(3-[3'-Trifluoromethylphenyl]-2-hydroxyphenyl)-9-hydroxy-naphth[1,2-d]imidazole-5-sulfonic acid hydrochloride;
2-(3-[4'-Fluorophenyl]-2-hydroxyphenyl)-9-hydroxy-naphth[1,2-d]imidazole-5-sulfonic acid hydrochloride;
2-(3-[4'-Chlorophenyl]-2-hydroxyphenyl)-9-hydroxy-naphth[1,2-d]imidazole-5-sulfonic acid hydrochloride;
2-(3-[1'-Dibenzofuranyl]-2-hydroxyphenyl)-9-hydroxy-naphth[1,2-d]imidazole-5-sulfonic acid hydrochloride;
2-(3-[1'-Naphthalenyl]-2-hydroxyphenyl)-9-hydroxy-naphth[1,2-d]imidazole-5-sulfonic acid hydrochloride;
2-(3-[3'-Chlorophenyl]-2-hydroxyphenyl)-9-hydroxy-naphth[1,2-d]imidazole-5-sulfonic acid hydrochloride;
2-(3-[3'-Nitrophenyl]-2-hydroxyphenyl)-9-hydroxy-naphth[1,2-d]imidazole-5-sulfonic acid hydrochloride;
2-(3-phenyl-2-hydroxyphenyl)-9-hydroxy-naphth[1,2-d]imidazole-5-sulfonic acid hydrochloride;
2-(3-[2'-Methylphenyl]-2-hydroxyphenyl)-9-hydroxy-naphth[1,2-d]imidazole-7-sulfonic acid hydrochloride;
2-(3-[4'-Methylphenyl]-2-hydroxyphenyl)-9-hydroxy-naphth[1,2-d]imidazole-7-sulfonic acid hydrochloride;
2-(3-[3',4'-Dimethylphenyl]-2-hydroxyphenyl)-9-hydroxy-naphth[1,2-d]imidazole-5-sulfonic acid hydrochloride;
2-(3-[3'-Trifluoromethylphenyl]-2-hydroxyphenyl)-9-hydroxy-naphth[1,2-d]imidazole-7-sulfonic acid hydrochloride;
2-(3-[4'-Fluorophenyl]-2-hydroxyphenyl)-9-hydroxy-naphth[1,2-d]imidazole-7-sulfonic acid hydrochloride;
2-(3-[4'-Chlorophenyl]-2-hydroxyphenyl)-9-hydroxy-naphth[1,2-d]imidazole-7-sulfonic acid hydrochloride;
2-(3-[1'-Dibenzofuranyl]-2-hydroxyphenyl)-9-hydroxy-naphth[1,2-d]imidazole-7-sulfonic acid hydrochloride;
2-(3-[1'-Naphthalenyl]-2-hydroxyphenyl)-9-hydroxy-naphth[1,2-d]imidazole-7-sulfonic acid hydrochloride;
2-(3-[3'-Chlorophenyl]-2-hydroxyphenyl)-9-hydroxy-naphth[1,2-d]imidazole-7-sulfonic acid hydrochloride;
2-(3-[3'-Nitrophenyl]-2-hydroxyphenyl)-9-hydroxy-naphth[1,2-d]imidazole-7-sulfonic acid hydrochloride;
2-(3-phenyl-2-hydroxyphenyl)-9-hydroxy-naphth[1,2-d]imidazole-7-sulfonic acid hydrochloride;
2-(4-[2'-Methylphenyl]-2-hydroxyphenyl)-9-hydroxy-naphth[1,2-d]imidazole-5-sulfonic acid hydrochloride;
2-(4-[4'-Methylphenyl]-2-hydroxyphenyl)-9-hydroxy-naphth[1,2-d]imidazole-5-sulfonic acid hydrochloride;
2-(4-[3'-Hydroxyphenyl]-2-hydroxyphenyl)-9-hydroxy-naphth[1,2-d]imidazole-5-sulfonic acid hydrochloride;
2-(4-[4'-Fluorophenyl]-2-hydroxyphenyl)-9-hydroxy-naphth[1,2-d]imidazole-5-sulfonic acid hydrochloride;
2-(4-[4'-Chlorophenyl]-2-hydroxyphenyl)-9-hydroxy-naphth[1,2-d]imidazole-5-sulfonic acid hydrochloride;
2-(4-[1'-Dibenzofuranyl]-2-hydroxyphenyl)-9-hydroxy-naphth[1,2-d]imidazole-5-sulfonic acid hydrochloride;
2-(4-[1'-Naphthalenyl]-2-hydroxyphenyl)-9-hydroxy-naphth[1,2-d]imidazole-5-sulfonic acid hydrochloride;
2-(4-[3'-Chlorophenyl]-2-hydroxyphenyl)-9-hydroxy-naphth[1,2-d]imidazole-5-sulfonic acid hydrochloride;
2-(4-[3'-Nitrophenyl]-2-hydroxyphenyl)-9-hydroxy-naphth[1,2-d]imidazole-5-sulfonic acid hydrochloride;
2-(4-phenyl-2-hydroxyphenyl)-9-hydroxy-naphth[1,2-d]imidazole-5-sulfonic acid hydrochloride;
2-(4-[2'-Methylphenyl]-2-hydroxyphenyl)-9-hydroxy-naphth[1,2-d]imidazole-7-sulfonic acid hydrochloride;
2-(4-[4'-Methylphenyl]-2-hydroxyphenyl)-9-hydroxy-naphth[1,2-d]imidazole-7-sulfonic acid hydrochloride;
2-(4-[3'-Hydroxyphenyl]-2-hydroxyphenyl)-9-hydroxy-naphth[1,2-d]imidazole-7-sulfonic acid hydrochloride;

2-(4-[4'-Fluorophenyl]-2-hydroxyphenyl)-9-hydroxy-naphth[1,2-d]imidazole-7-sulfonic acid hydrochloride;

2-(4-[4'-Chlorophenyl]-2-hydroxyphenyl)-9-hydroxy-naphth[1,2-d]imidazole-7-sulfonic acid hydrochloride;

2-(4-[1'-Dibenzofuranyl]-2-hydroxyphenyl)-9-hydroxy-naphth[1,2-d]imidazole-7-sulfonic acid hydrochloride;

2-(4-[1'-Naphthalenyl]-2-hydroxyphenyl)-9-hydroxy-naphth[1,2-d]imidazole-7-sulfonic acid hydrochloride;

2-(4-[3'-Chlorophenyl]-2-hydroxyphenyl)-9-hydroxy-naphth[1,2-d]imidazole-7-sulfonic acid hydrochloride;

2-(4-[3'-Nitrophenyl]-2-hydroxyphenyl)-9-hydroxy-naphth[1,2-d]imidazole-7-sulfonic acid hydrochloride;

2-(4-phenyl-2-hydroxyphenyl)-9-hydroxy-naphth[1,2-d]imidazole-7-sulfonic acid hydrochloride;

2-(3-phenyl-2-methoxyphenyl)-9-hydroxy-naphth[1,2-d]imidazole-7-carboxylic acid hydrochloride;

2-(3-[3',4'-dimethylphenyl]-2-methoxyphenyl)-9-hydroxy-naphth[1,2-d]imidazole-7-carboxylic acid trifluoroacetate;

2-(3-[3',4'-dimethylphenyl]-2-hydroxyphenyl)-9-hydroxy-naphth[1,2-d]imidazole-7-carboxylic acid trifluoroacetate;

2-(1-[3,4-dimethylphenyl]-3-methyl-5-hydroxy-1H-pyrrazole-4-yl)-9-hydroxy-3H-naphth[1,2-d]imidazole-7-carboxylic acid trifluoroacetate;

2-(1-hydroxy-2-naphthalenyl)-9-hydroxy-naphth[1,2-d]imidazole-7-carboxylic acid trifluoroacetate;

2-(2-pyridinyl)-9-hydroxy-naphth[1,2-d]imidazole-7-carboxylic acid trifluoroacetate;

2-(3',4'-dimethylbiphenyl-3-yl)-9-hydroxy-3H-naphtho[1,2-d]imidazole-7-sulfonic acid hydrochloride;

2-biphenyl-4-yl-9-hydroxy-3H-naphtho[1,2-d]imidazole-7-sulfonic acid hydrochloride;

2-(3',4'-dimethylbiphenyl-4-yl)-9-hydroxy-3H-naphtho[1,2-d]imidazole-7-sulfonic acid trifluoroacetate;

2-(4'-tert-butylbiphenyl-3-yl)-9-hydroxy-3H-naphtho[1,2-d]imidizole-7-sulfonic acid trifluoroacetate;

2-[3-(4-tert-butylbenzyloxy)-phenyl]-9-hydroxy-3H-naphtho[1,2-d]imidizole-7-sulfonic acid hydrochloride;

2-[3-(3-trifluoromethylbenzyloxy)-phenyl]-9-hydroxy-3H-naphtho[1,2-d]imidizole-7-sulfonic acid hydrochloride;

2-[3-(3,4-dimethylbenzyloxy)-phenyl]-9-hydroxy-3H-naphtho[1,2-d]imidizole-7-sulfonic acid hydrochloride;

2-(3',4'-dimethylbiphenyl-3-yl)-9-hydroxy-3H-naphtho[1,2-d]imidazole-7-carboxylic acid hydrochloride;

2-(3',4'-dimethylbiphenyl-4-yl)-9-hydroxy-3H-naphtho[1,2-d]imidazole-7-carboxylic acid trifluoroacetate;

2-(4'-tert-butylbiphenyl-3-yl)-9-hydroxy-3H-naphtho[1,2-d]imidazole-7-carboxylic acid trifluoroacetate;

9-hydroxy-2-(3-phenoxyphenyl)-3H-naphtho[1,2-d]imidazole-7-carboxylic acid trifluoroacetate;

3-[2-(3',4'-dimethylbiphenyl-3-yl)-9-hydroxy-3H-naphtho[1,2-d]imidazole-7-sulfonylamino]-benzoic acid;

1-[2-(3',4'-dimethylbiphenyl-3-yl)-9-hydroxy-3H-naphtho[1,2-d]imidazole-7-sulfonyl]-piperidine-3-carboxylic acid;

(S)-1-[2-(3',4'-dimethyl-biphenyl-3-yl)-9-hydroxy-3H-naphtho[1,2-d]imidazole-7-sulfonyl]-pyrrolidine-2-carboxylic acid;

({1-[2-(3',4'-dimethylbiphenyl-3-yl)-9-hydroxy-3H-naphtho[1,2-d]imidazol-7-yl]-methanoyl}-amino)-acetic acid;

(S)-2-({1-[2-(3',4'-dimethylbiphenyl-3-yl)-9-hydroxyl-3H-naphtho[1,2-d]imidazol-7-yl]-methanoyl}-amino)-propionic acid;

({1-[2-(3',4'-dimethylbiphenyl-3-yl)-9-hydroxyl-3H-naphtho[1,2-d]imidazol-7-yl]-methanoyl}-methylamino)-acetic acid;

(S)-1-{1-[2-(3',4'-dimethylbiphenyl-3-yl)-9-hydroxyl-3H-naphtho[1,2-d]imidazol-7-yl]-methanoyl}-pyrrolidine-2-carboxylic acid;

(S)-2-({1-[2-(4' tert-butyllbiphenyl-3-yl)-9-hydroxy-3H-naphtho[1,2-d]imidazol-7-yl]-methanoyl}-amino)-pentanedioic acid;

2-[6-(4-tert-butylphenyl)-pyridin-2-yl]-9-hydroxy-3H-naphtho[1,2-d]imidazole-7-carboxylic acid;

2-[5-(3,4-dichlorophenyl)furan-2-yl]-9-hydroxy-3H-naphtho[1,2-d]imidazole-7-carboxylic acid;

2-[5-benzo[b]thiophen-2-yl-furan-2-yl]-9-hydroxy-3H-naphtho[1,2-d]imidazole-7-carboxylic acid;

9-Hydroxy-2-[5-(4-tert-butylphenyl)-furan-2-yl]-3H-naphtho[1,2-d]imidazole-7-carboxylic acid;

9-Hydroxy-2-[4-(4-tert-butylphenyl)-furan-2-yl]-3H-naphtho[1,2-d]imidazole-7-carboxylic acid;

2-[5-(3,4-dimethylphenyl)-furan-2-yl]-9-hydroxy-3H-naphtho[1,2-d]imidazole-7-carboxylic acid;

2-[4-(3,4-dimethylphenyl)-furan-2-yl]-9-hydroxy-3H-naphtho[1,2-d]imidazole-7-carboxylic acid;

2-[5-(4-tert-butylphenyl)-thiophen-2-yl]-9-hydroxy-3H-naphtho[1,2-d]imidazole-7-carboxylic acid;

2-[4-(4-tert-butylphenyl)-thiophen-2-yl]-4-hydroxy-3H-naphtho[1,2-d]imidazole-7-carboxylic acid;

2-[5-(3,4-dimethylphenyl)-thiophen-2-yl]-9-hydroxy-3H-naphtho[1,2-d]imidazole-7-carboxylic acid;

2-[4-(3,4-dimethylphenyl)-thiophen-2-yl]-9-hydroxy-3H-naphtho[1,2-d]imidazole-7-carboxylic acid;

2-[4'-tert-butyl-6-methoxybiphenyl-3-yl]-9-hydroxy-3H-naphtho[1,2-d]imidazole-7-carboxylic acid;

2-[4'-tert-butyl-6-fluoro-biphenyl-3-yl]-9-hydroxy-3H-naphtho[1,2-d]imidazole-7-carboxylic acid;

2-[4'-tert-butyl-4-fluorobiphenyl-3-yl]-9-hydroxy-3H-naphtho[1,2-d]imidazole-7-carboxylic acid;

2-[6-fluoro-3',4'-dimethylbiphenyl-3-yl]-9-hydroxy-3H-naphtho[1,2-d]imidazole-7-carboxylic acid;

2-[4-fluoro-3',4'-dimethylbiphenyl-3-yl]-9-hydroxy-3H-naphtho[1,2-d]imidazole-7-carboxylic acid;

2-[4'-trifluoromethylbiphenyl-3-yl]-9-hydroxy-3H-naphtho[1,2-d]imidazole-7-carboxylic acid;

9-Hydroxy-2-[5-(3-isopropylphenyl)-furan-2-yl]-3H-naphtho[1,2-d]imidazole-7-carboxylic acid;

9-Hydroxy-2-[4-(4-tert-butylphenyl)-furan-2-yl]-3H-naphtho[1,2-d]imidazole-7-carboxylic acid;

9-Hydroxy-2-[5-(4-tert-butylphenyl)-furan-2-yl]-3H-naphtho[1,2-d]imidazole-7-carboxylic acid;

2-[5-(3,4-dimethylphenyl)-thiophen-2-yl]-9-hydroxy-3H-naphtho[1,2-d]imidazole-7-carboxylic acid;

2-[4-(3,4-dimethylphenyl)-thiophen-2-yl]-9-hydroxy-3H-naphtho[1,2-d]imidazole-7-carboxylic acid;

2-[4-(4-tert-butylphenyl)-thiophen-2-yl]-9-hydroxy-3H-naphtho[1,2-d]imidazole-7-carboxylic acid;

2-[5-(4-tert-butylphenyl)-thiophen-2-yl]-9-hydroxy-3H-naphtho[1,2-d]imidazole-7-carboxylic acid;

2-[5-(3,4-dichlorophenyl)furan-2-yl]-9-hydroxy-3H-naphtho[1,2-d]imidazole-7-carboxylic acid;

2-[5-benzo[b]thiophen-2-yl-furan-2-yl]-9-hydroxy-3H-naphtho[1,2-d]imidazole-7-carboxylic acid;

2-[4'-tert-butyl-6-methoxybiphenyl-3-yl]-9-hydroxy-3H-naphtho[1,2-d]imidazole-7-carboxylic acid;

2-[6-fluoro-3',4'-dimethylbiphenyl-3-yl]-9-hydroxy-3H-naphtho[1,2-d]imidazole-7-carboxylic acid;

2-[4-fluoro-3',4'-dimethylbiphenyl-3-yl]-9-hydroxy-3H-naphtho[1,2-d]imidazole-7-carboxylic acid;

2-[4'-tert-butyl-4-fluorobiphenyl-3-yl]-9-hydroxy-3H-naphtho[1,2-d]imidazole-7-carboxylic acid;

2-[4'-trifluoromethylbiphenyl-3-yl]-9-hydroxy-3H-naphtho[1,2-d]imidazole-7-carboxylic acid;

2-[4'-tert-butyl-6-fluoro-biphenyl-3-yl]-9-hydroxy-3H-naphtho[1,2-d]imidazole-7-carboxylic acid;

2-[5-(4-tert-butylphenyl)-pyridin-3-yl]-9-hydroxy-1H-naphtho[1,2-d]imidazole-7-carboxylic acid;

2-[(2-fluoro-4-trifluoromethylbiphenyl)-3-yl]-9-hydroxy-1H-naphtho[1,2-d]imidazole-7-carboxylic acid;

2-[(2,5-difluoro-4-trifluoromethylbiphenyl)-3-yl]-9-hydroxy-1H-naphtho[1,2-d]imidazole-7-carboxylic acid;

2-[(4-fluoro-4'-trifluoromethylbiphenyl)-3-yl]-9-hydroxy-1H-naphtho[1,2-d]imidazole-7-carboxylic acid;

2-[5-(4-trifluoromethylphenyl)-furan-2-yl]-9-hydroxy-3H-naphtho[1,2-d]imidazole-7-carboxylic acid;

2-[4-(4-trifluoromethylphenyl)-thiophen-2-yl]-9-hydroxy-3H-naphtho[1,2-d]imidazole-7-carboxylic acid;

2-(4'-ethylbiphenyl-3-yl)-9-hydroxy-3H-naphtho[1,2-d]imidazole-7-carboxylic acid;

2-(4'-propylbiphenyl-3-yl)-9-hydroxy-3H-naphtho[1,2-d]imidazole-7-carboxylic acid;

2-(4'-butylbiphenyl-3-yl)-9-hydroxy-3H-naphtho[1,2-d]imidazole-7-carboxylic acid;

2-(4'-carboxy-3'-methylbiphenyl-3-yl)-9-hydroxy-3H-naphtho[1,2-d]imidazole-7-carboxylic acid;

2-(4'-cyano-3'-methylbiphenyl-3-yl)-9-hydroxy-3H-naphtho[1,2-d]imidazole-7-carboxylic acid;

2-(4'-fluoro-3'-methylbiphenyl-3-yl)-9-hydroxy-3H-naphtho[1,2-d]imidazole-7-carboxylic acid;

2-[1-(4-tert-butylphenyl)-1H-pyrazol-4-yl]-9-hydroxy-3H-naphtho[1,2-d]imidazole-7-carboxylic acid;

2-(3',4'-difluorobiphenyl-3-yl)-9-hydroxy-3H-naphtho[1,2-d]imidazole-7-carboxylic acid; and 2-[3-(9H-fluoren-2-yl)-phenyl]-9-hydroxy-3H-naphtho[1,2-d]imidazole-7-carboxylic acid, and pharmaceutically acceptable salts, hydrates, solvates and esters thereof.

* * * * *